United States Patent
Morgan et al.

(10) Patent No.: US 11,754,573 B2
(45) Date of Patent: *Sep. 12, 2023

(54) METHODS FOR THE QUANTITATION OF POLYPEPTIDES

(71) Applicant: Genzyme Corporation, Cambridge, MA (US)

(72) Inventors: Christopher Morgan, Southborough, MA (US); Xiaokui Zhang, Northborough, MA (US)

(73) Assignee: Genzyme Corporation, Cambridge, MA (US)

( * ) Notice: Subject to any disclaimer, the term of this patent is extended or adjusted under 35 U.S.C. 154(b) by 142 days.

This patent is subject to a terminal disclaimer.

(21) Appl. No.: 17/349,840

(22) Filed: Jun. 16, 2021

(65) Prior Publication Data

US 2022/0003780 A1    Jan. 6, 2022

Related U.S. Application Data

(63) Continuation of application No. 16/246,376, filed on Jan. 11, 2019, now Pat. No. 11,067,584.

(60) Provisional application No. 62/617,080, filed on Jan. 12, 2018.

(51) Int. Cl.
*G01N 7/00* (2006.01)
*G01N 33/68* (2006.01)

(52) U.S. Cl.
CPC ..... *G01N 33/6857* (2013.01); *G01N 33/6848* (2013.01); *G01N 33/6854* (2013.01)

(58) Field of Classification Search
CPC .......... G01N 33/6857; G01N 33/6848; G01N 33/6854
See application file for complete search history.

(56) References Cited

U.S. PATENT DOCUMENTS

| | | | |
|---|---|---|---|
| 5,731,168 | A | 3/1998 | Carter et al. |
| 5,807,706 | A | 9/1998 | Carter et al. |
| 5,821,333 | A | 10/1998 | Carter et al. |
| 7,632,686 | B2 | 12/2009 | Anderson |
| 7,642,228 | B2 | 1/2010 | Carter |
| 7,695,936 | B2 | 4/2010 | Carter |
| 8,216,805 | B2 | 7/2012 | Carter |
| 8,388,965 | B2 | 3/2013 | Rao |
| 8,679,785 | B2 | 3/2014 | Carter |
| 8,871,912 | B2 | 10/2014 | Davis |
| 9,029,508 | B2 | 5/2015 | Ghayur |
| 9,035,027 | B2 | 5/2015 | Ghayur |
| 9,046,513 | B2 | 6/2015 | Ghayur |
| 9,109,026 | B2 | 8/2015 | Ghayur |
| 9,164,089 | B2 | 10/2015 | Anderson |
| 9,181,349 | B2 | 11/2015 | Baurin |
| 9,221,917 | B2 | 12/2015 | Baurin |
| 9,732,162 | B2 | 8/2017 | Rao |
| 9,738,728 | B2 | 8/2017 | Rao |
| 11,067,584 | B2 | 7/2021 | Morgan |
| 2009/0232811 | A1 | 9/2009 | Klein et al. |
| 2017/0320967 | A1 | 11/2017 | Yang et al. |
| 2020/0182883 | A1 | 6/2020 | Sajadi et al. |

FOREIGN PATENT DOCUMENTS

| | | | |
|---|---|---|---|
| EP | 2573121 | B1 | 8/2017 |
| RU | 2545783 | C2 | 4/2015 |
| WO | WO-2007/147901 | A1 | 12/2007 |
| WO | WO-2009/080251 | A1 | 7/2009 |
| WO | WO-2009/080252 | A1 | 7/2009 |
| WO | WO-2009/080253 | A1 | 7/2009 |
| WO | WO-2009/080254 | A1 | 7/2009 |
| WO | WO-2009/089004 | A1 | 7/2009 |
| WO | WO-2010124998 | A1 | 11/2010 |
| WO | WO-2011/131746 | A2 | 10/2011 |
| WO | WO-2011/131746 | A3 | 10/2011 |
| WO | WO-2012/135345 | A1 | 10/2012 |
| WO | WO-2012/155019 | A1 | 11/2012 |
| WO | WO-2016/116626 | A1 | 7/2016 |
| WO | WO-2017/074878 | A1 | 5/2017 |
| WO | WO-2017/074878 | A8 | 5/2017 |
| WO | WO-2017/180913 | A2 | 10/2017 |
| WO | WO-2017/180913 | A3 | 10/2017 |
| WO | WO-2017/180913 | A9 | 10/2017 |
| WO | WO-2017/205694 | A1 | 11/2017 |

OTHER PUBLICATIONS

Abou-Nader, M. et al. (Sep. 2010). "Rapid Generation Of Random Mutant Libraries," Bioengineered Bugs 1(5):337-340.
Anderson, N. L. et al. (2004) "Mass Spectrometric Quantitation Of Peptides And Proteins Using Stable Isotope Standards And Capture By Anti-Peptide Antibodies (SISCAPA)," J Proteome Res. 3(2):235-244.
Cirino, P.C. et al. (2003). "Generating Mutant Libraries Using Error-Prone PCR," Methods Mol Biol. 231:3-9.
Egan, T.J. et al. (Jan. 2, 2017). "Novel Multispecific Heterodimeric Antibody Format Allowing Modular Assembly Of Variable Domain Fragments," mAbs 9(1):68-84.
El-Khoury, J. et al. (2013). "Liquid Chromatography—Tandem Mass Spectrometry in the Clinical Laboratory" J. Chrom. & Separation Tech. 4(5):1000e115.
Firth, A.E. et al. (Jun. 2, 2005). "Statistics Of Protein Library Construction," Bioinformatics 21(15):3314-3315.
Giansanti, P. et al. (May 11, 2016). "Six Alternative Proteases For Mass Spectrometry-Based Proteomics Beyond Trypsin," Nature Protocols 11(5): 993-1006.
Grebe, S.K.G. et al. (Feb. 2011). "LC-MS/MS in the Clinical Laboratory—Where to From Here?" Clin. Biochem Review 32(1):5-31.
Gundry, R.L. et al. (Oct. 2009). "Preparation Of Proteins And Peptides For Mass Spectrometry Analysis In A Bottom-Up Proteomics Workflow," Curr Protoc Mol Biol. 90(1):10-25.

(Continued)

*Primary Examiner* — Jeanette M Lieb
(74) *Attorney, Agent, or Firm* — Morrison & Foerster LLP

(57) ABSTRACT

Provided are methods for quantitating an amount of a polypeptide that comprises a portion of an antibody present in a sample (e.g., a plasma or serum sample) wherein the antibody comprises a constant region (e.g., a heavy chain or light chain constant region) that comprises an engineered mutation.

21 Claims, 37 Drawing Sheets

Specification includes a Sequence Listing.

(56) References Cited

OTHER PUBLICATIONS

Hedrick, V.E. et al. (Sep. 2015). "Digestion, Purification, and Enrichment of Protein Samples for Mass Spectrometry," Curr Protoc Chem Biol. 7(3): 201-222.
International Immunogenetics Information System (IMGT). (May 17, 2001). "IMGT Scientic Chart," as retrieved on Jun. 10, 2020 at WorldWideWeb.imgt.org/IMGTScientificChart/Numbering/HulGHGnber.html, 5 pages.
International Search Report and Written Opinion dated Mar. 29, 2019 for PCT Application No. PCT/US2019/013373 filed Jan. 11, 2019, 12 pages.
Jannetto, P. (Jul. 1, 2015). "Liquid Chromatography Tandem Mass Spectrometry," AAC, Clinical Laboratory News, 5 pages, as retrieved on https://www.aacc.org/cln/articles/2015/july/liquid-chromatography-tandem-mass-spectrometry.
Kalim, M. et al. (2017). "Intracellular Trafficking Of New Anticancer Therapeutics: Antibody-Drug Conjugates," Drug Design, Development And Therapy 11:2265-2276.
Klein, C. et al. (Aug. 27, 2012). "Progress In Overcoming The Chain Association Issue In Bispecific Heterodimeric Igg Antibodies," MAbs. 4(6):653-663.
Lanshoeft, C. et al. (2016, e-pub. Jan. 12, 2016). "The Use Of Generic Surrogate Peptides For The Quantitative Analysis Of Human Immunoglobulin GI In Pre-Clinical Species With High-Resolution Mass Spectrometry," Anal. Bional. Chem. 408(6):1687-1699.
Liu, H. et al. (Jan. 26, 2017). "Fc Engineering For Developing Therapeutic Bispecific Antibodies And Novel Scaffolds," Frontiers in Immunology 8:38.
Muda, M. et al. (May 1, 2011). "Therapeutic Assessment Of SEED: A New Engineered Antibody Platform Designed To Generate Mono— And Bispecific Antibodies," Protein Engineering, Design & Selection 24(5):447-454.
Nordhoff, E. et al. (2003). "Sample Preparation Protocols For MALDI-MS Of Peptides And Oligonucleotides Using Prestructured Sample Supports," International Journal of Mass Spectrometry 226(1):163-180.
Ouyang, Z., et al. (Jan. 2012). "Pellet Digestion: A Simple And Efficient Sample Preparation Technique For LC-MS/MS Quantification Of Large Therapeutic Proteins In Plasma," Bioanalysis 4(1): 17-28.
Parslow, A.C. et al. (Sep. 2016). "Antibody-Drug Conjugates for Cancer Therapy," Biomedicines 4(3):14.
Pirakitikulr, N. et al. (Dec. 2010). "PCRless Library Mutagenesis Via Oligonucleotide Recombination In Yeast," Protein Sci. 19(12):2336-2346.
Razavi, N. et al. (Aug. 8, 2016) "Multiplexed Longitudinal Measurement Of Protein Biomarkers In DBS Using An Automated SISCAPA Workflow," Bioanalysis 8(15):1597-1609.
Schaefer, W. et al. (Jul. 5, 2011). "Immunoglobulin Domain Crossover As A Generic Approach For The Production Of Bispecific Igg Antibodies," PNAS USA 108(27):11187-11192.
Schaefer, W. et al. (Jan. 2016, e-pub. Dec. 9, 2015). "Heavy And Light Chain Pairing Of Bivalent Quadroma And Knobs-Into-Holes Antibodies Analyzed By UHR-ESI-QTOF Mass Spectrometry," MABS 8(1):49-55.
Shushan, B. et al. (Nov. 2010) "A Review Of Clinical Diagnostic Applications Of Liquid Chromatography—Tandem Mass Spectrometry," Mass Spec. Rev. 29(6):930-944.
Spiess, C. et al. (2015, e-pub. Jan. 27, 2015). "Alternative Molecular Formats and Therapeutic Applications For Bispecific Antibodies," Mol. Immunol. 67:95-106.
Steffens, D.L. et al. (Jul. 2007). "Efficient Site-Directed Saturation Mutagenesis Using Degenerate Oligonucleotides," J. Biomol Tech. 18(3):147-149.
Steinmetz, A. et al. (Jul. 3, 2016). "CODV-Ig, A Universal Bispecific Tetravalent And Multifunctional Immunoglobulin Format For Medical Applications," MAbs. 8(5):867-878.
Thermofisher Scientific (Jul. 25, 2017). "Sample Preparation for Mass Spectrometry," ThermoFisher Scientific, 6 pages, as retrieved on Wayback Machine from https://web.archive.org/web/20170725052804/https://www.thermofisher.com/us/en/home/life-science/protein-biology/protein-biology-learning-center/protein-biology-resource-library/pierce-protein-methods/sample-preparation-mass-spectrometry.html.
Weidle, U.H. et al. (Jan. 2013). "The Intriguing Options Of Multispecific Antibody Formats For Treatment Of Cancer," Cancer Genomics—Proteomics 10(1): 1-18.
Whiteaker, J.R. et al. (Apr. 2011). "Evaluation Of Large Scale Quantitative Proteomic Assay Development Using Peptide Affinity-Based Mass Spectrometry," Mol Cell Proteomics 10(4):10.1074/mcp.M110.005645-1-10.1074/mcp.M110.005645-10.
Wu, C. et al. (Nov. 2007; e-pub. Oct. 14, 2007). "Simultaneous Targeting of Multiple Disease Mediators by a Dual-Variable-Domain Immunoglobulin," Nat. Biotechnol. 25(11):1290-1297.
Yin, Y. et al. (Sep. 9, 2016, e-pub. Nov. 1, 2016). "Precise Quantification Of Mixtures Of Bi Specific Igg Produced In Single Host Cells By Liquid Chromatography—Orbitrap High-Resolution Mass Spectrometry," MABS 8(8):1467-1476.
Zhang, G. et al. (Oct. 1, 2014). "Overview Of Peptide And Protein Analysis By Mass Spectrometry," Curr Protoc Mol Biol. 108(10.21):1-30.
Furlong, M.T. (Jun. 2, 2017). "Generic Peptide Strategies for LC-MS/MS Bioanalysis of Human Monoclonal Antibody Drugs and Drug Candidates," Protein Analysis using Mass Spectrometry: Accelerating Protein Biotherapeutics from Lab to Patient, pp. 161-181.

|  | Hinge | | | | |
|---|---|---|---|---|---|
| SEQ ID NO: 1 | THTCPPCPAP | ELLGGPSVFL | FPPKPKDTLM | ISRTPEVTCV | VVDVSHEDPE | VKFNWYVDGV |
| SEQ ID NO: 2 | THTCPPCPAP | ELLGGPSVFL | FPPKPKDTLM | ISRTPEVTCV | VVDVSHEDPE | VKFNWYVDGV |
| SEQ ID NO: 3 | THTCPPCPAP | ELLGGPSVFL | FPPKPKDTLM | ISRTPEVTCV | VVDVSHEDPE | VKFNWYVDGV |
| SEQ ID NO: 4 | THTCPPCPAP | ELLGGPSVFL | FPPKPKDTLM | ISRTPEVTCV | VVDVSHEDPE | VKFNWYVDGV |
| SEQ ID NO: 5 | THTCPPCPAP | ELLGGPSVFL | FPPKPKDTLM | ISRTPEVTCV | VVDVSHEDPE | VKFNWYVDGV |

| SEQ ID NO: 1 | EVHNAKTKPR | EEQYNSTYRV | VSVLTVLHQD | WLNGKEYKCK | VSNKALPAPI | EKTISKAKGQ |
| SEQ ID NO: 2 | EVHNAKTKPR | EEQYNSTYRV | VSVLTVLHQD | WLNGKEYKCK | VSNKALPAPI | EKTISKAKGQ |
| SEQ ID NO: 3 | EVHNAKTKPR | EEQYNSTYRV | VSVLTVLHQD | WLNGKEYKCK | VSNKALPAPI | EKTISKAKGQ |
| SEQ ID NO: 4 | EVHNAKTKPR | EEQYNSTYRV | VSVLTVLHQD | WLNGKEYKCK | VSNKALPAPI | EKTISKAKGQ |
| SEQ ID NO: 5 | EVHNAKTKPR | EEQYNSTYRV | VSVLTVLHQD | WLNGKEYKCK | VSNKALPAPI | EKTISKAKGQ | engineered Cys-pair

| SEQ ID NO: 1 | PREPQVYTLP | PSRDELTKNQ | VSLTCLVKGF | YPSDIAVEWE | SNGQPENNYK | TTPPVLDSDG |
| SEQ ID NO: 2 | PREPQVYTLP | PCRDELTKNQ | VSLWCLVKGF | YPSDIAVEWE | SNGQPENNYK | TTPPVLDSDG |
| SEQ ID NO: 3 | PREPQVCTLP | PSRDELTKNQ | VSLSCAVKGF | YPSDIAVEWE | SNGQPENNYK | TTPPVLDSDG |
| SEQ ID NO: 4 | PREPQVCTLP | PSRDELTKNQ | VSLSCAVKGF | YPSDIAVEWE | SNGQPENNYK | TTPPVLDSDG |
| SEQ ID NO: 5 | PREPQVYTLP | PCRDELTKNQ | VSLWCLVKGF | YPSDIAVEWE | SNGQPENNYK | TTPPVLDSDG | increase half-life

| SEQ ID NO: 1 | SFFLYSKLTV | DKSRWQQGNV | FSCSVMHEAL | HNHYTQKSLS | LSPGK |
| SEQ ID NO: 2 | SFFLYSKLTV | DKSRWQQGNV | FSCSVLHEAL | HSHYTQKSLS | LSPG |
| SEQ ID NO: 3 | SFFLVSKLTV | DKSRWQQGNV | FSCSVLHEAL | HSHYTQKSLS | LSPG |
| SEQ ID NO: 4 | SFFLVSKLTV | DKSRWQQGNV | FSCSVMHEAL | HNHYTQKSLS | LSPGK |
| SEQ ID NO: 5 | SFFLYSKLTV | DKSRWQQGNV | FSCSVMHEAL | HNHYTQKSLS | LSPG |

FIG. 1

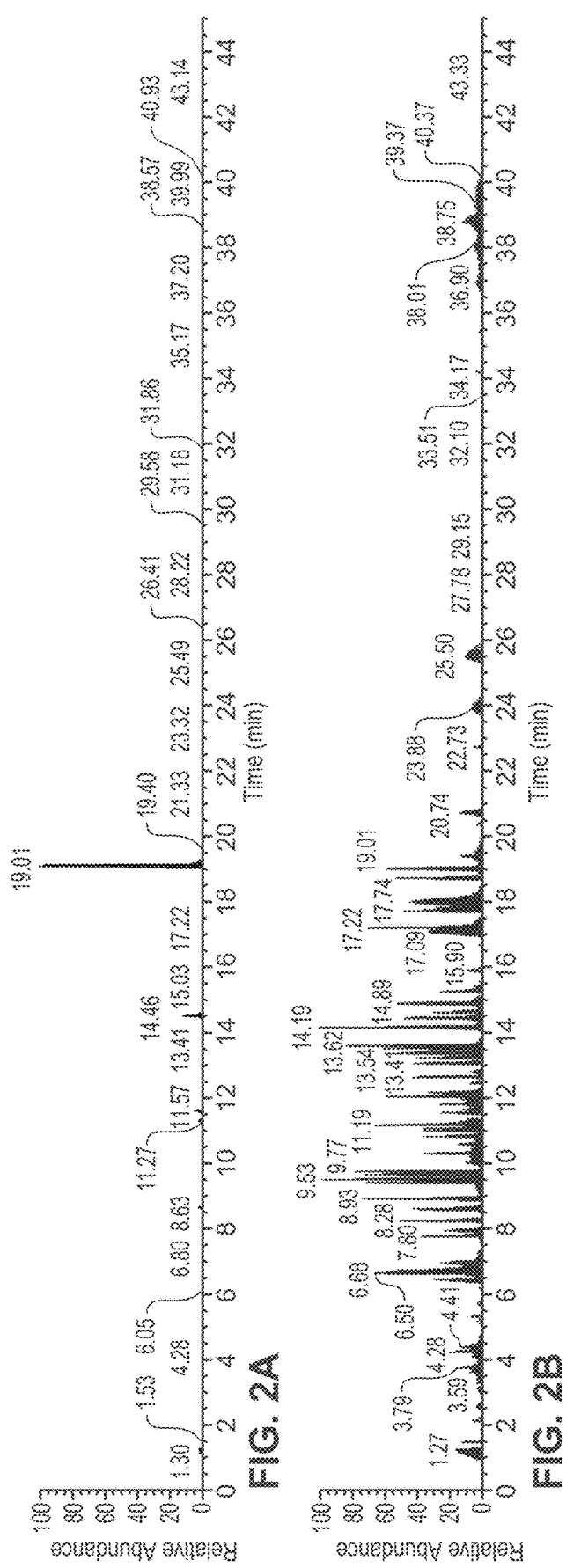
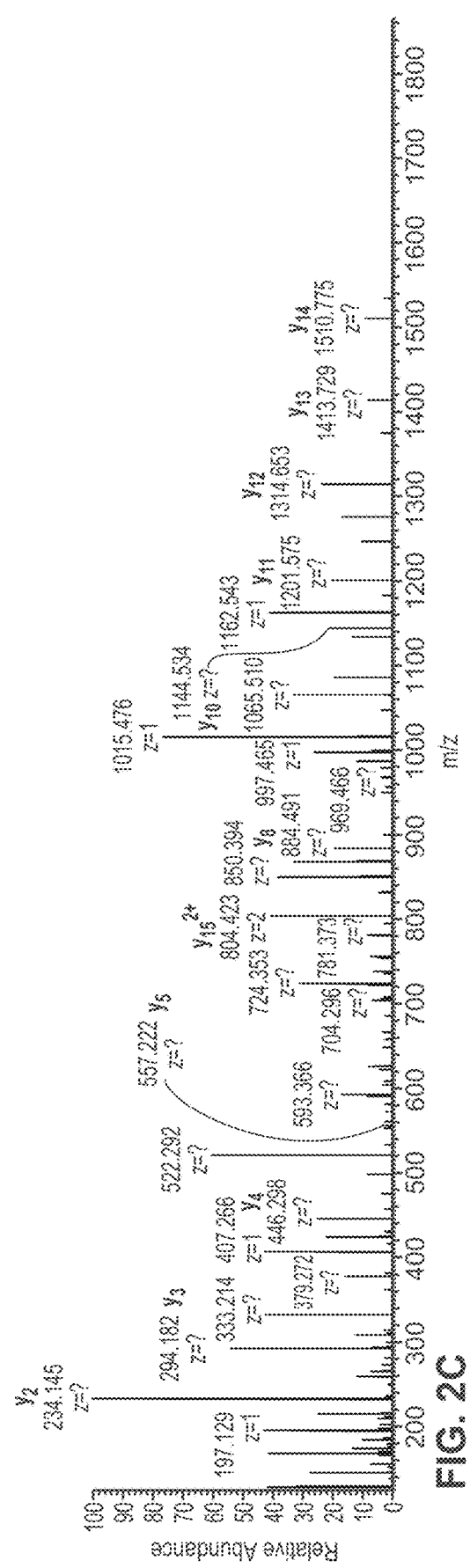
FIG. 2A
FIG. 2B
FIG. 2C

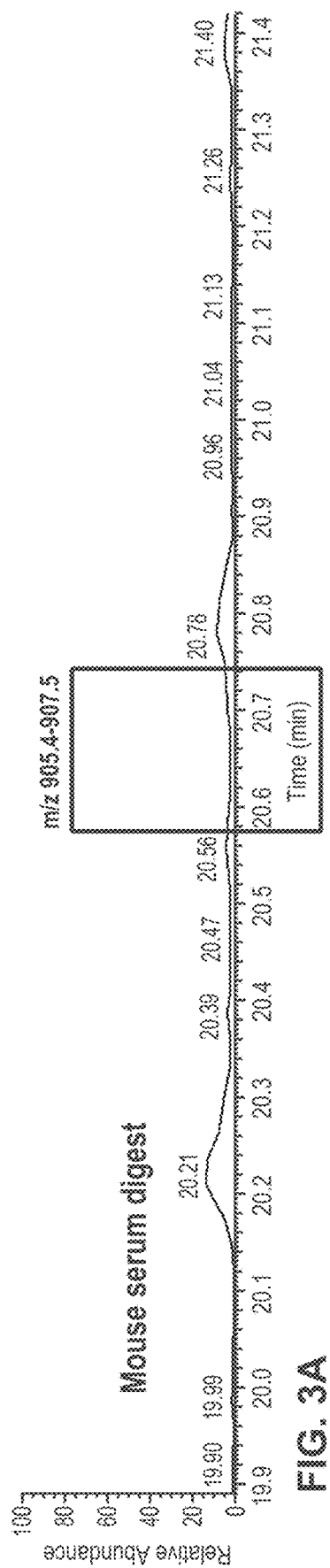
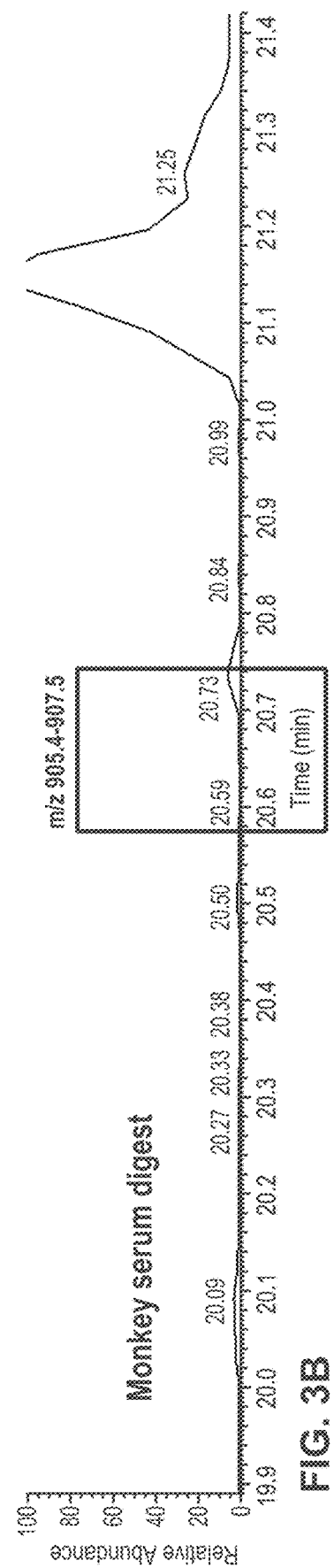
FIG. 3A
FIG. 3B

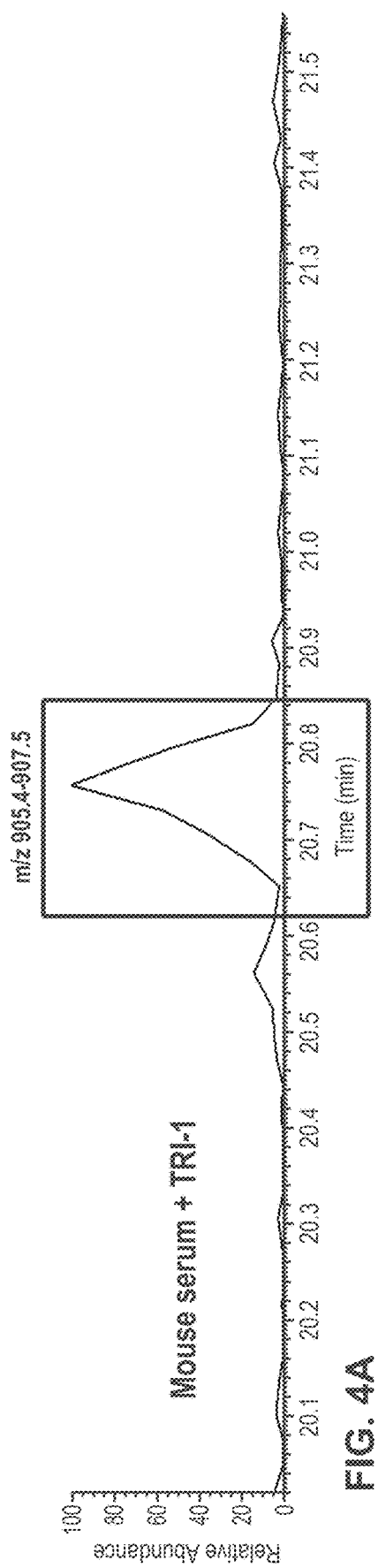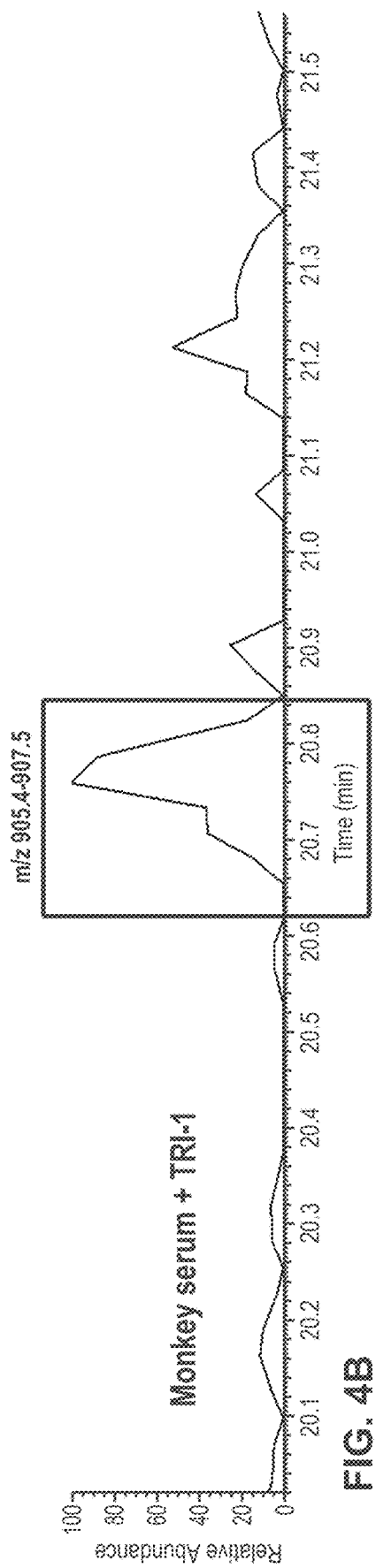
FIG. 4A
FIG. 4B

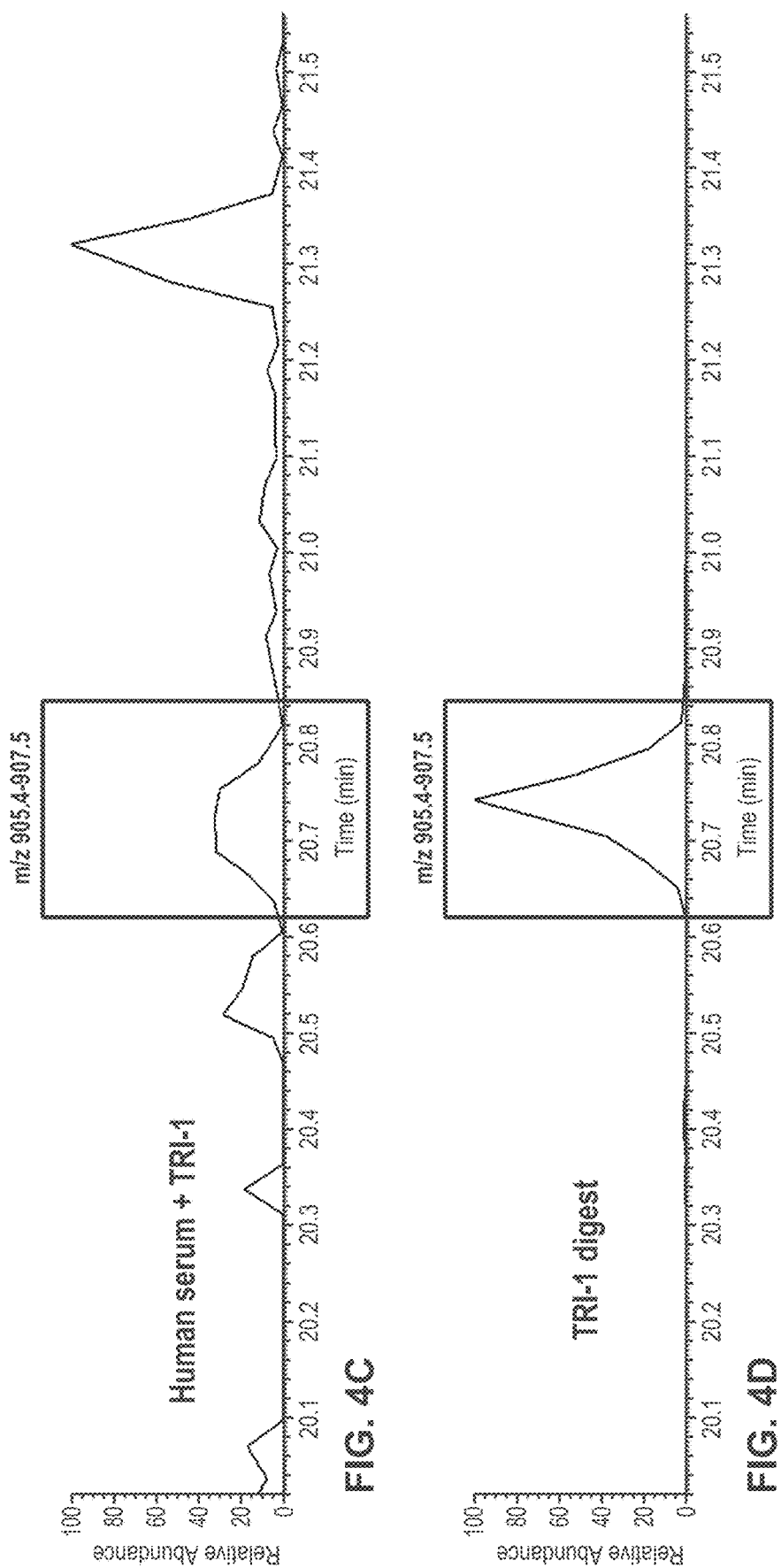

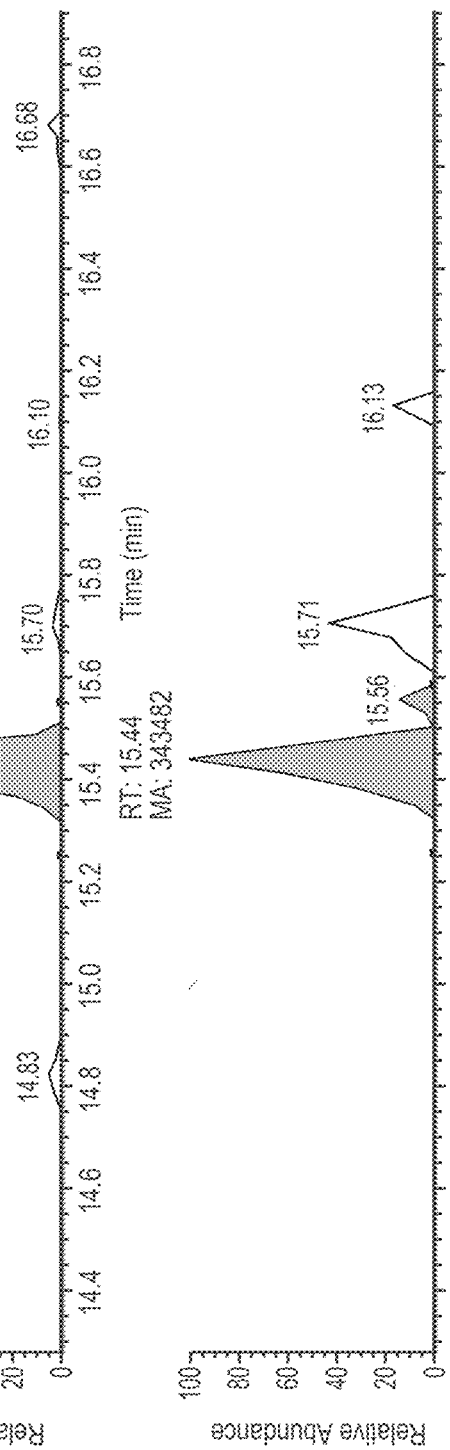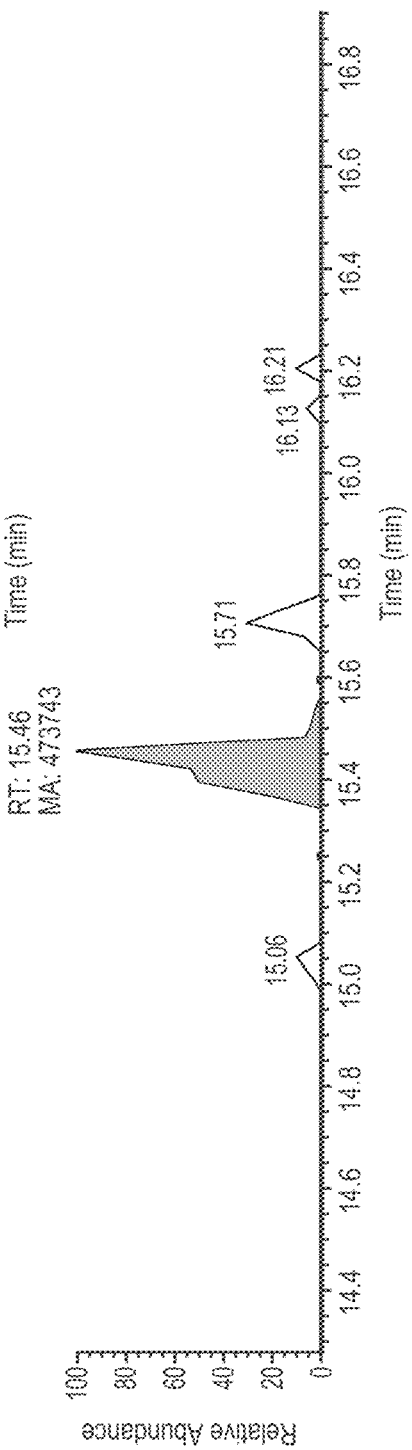
FIG. 7A
FIG. 7B
FIG. 7C

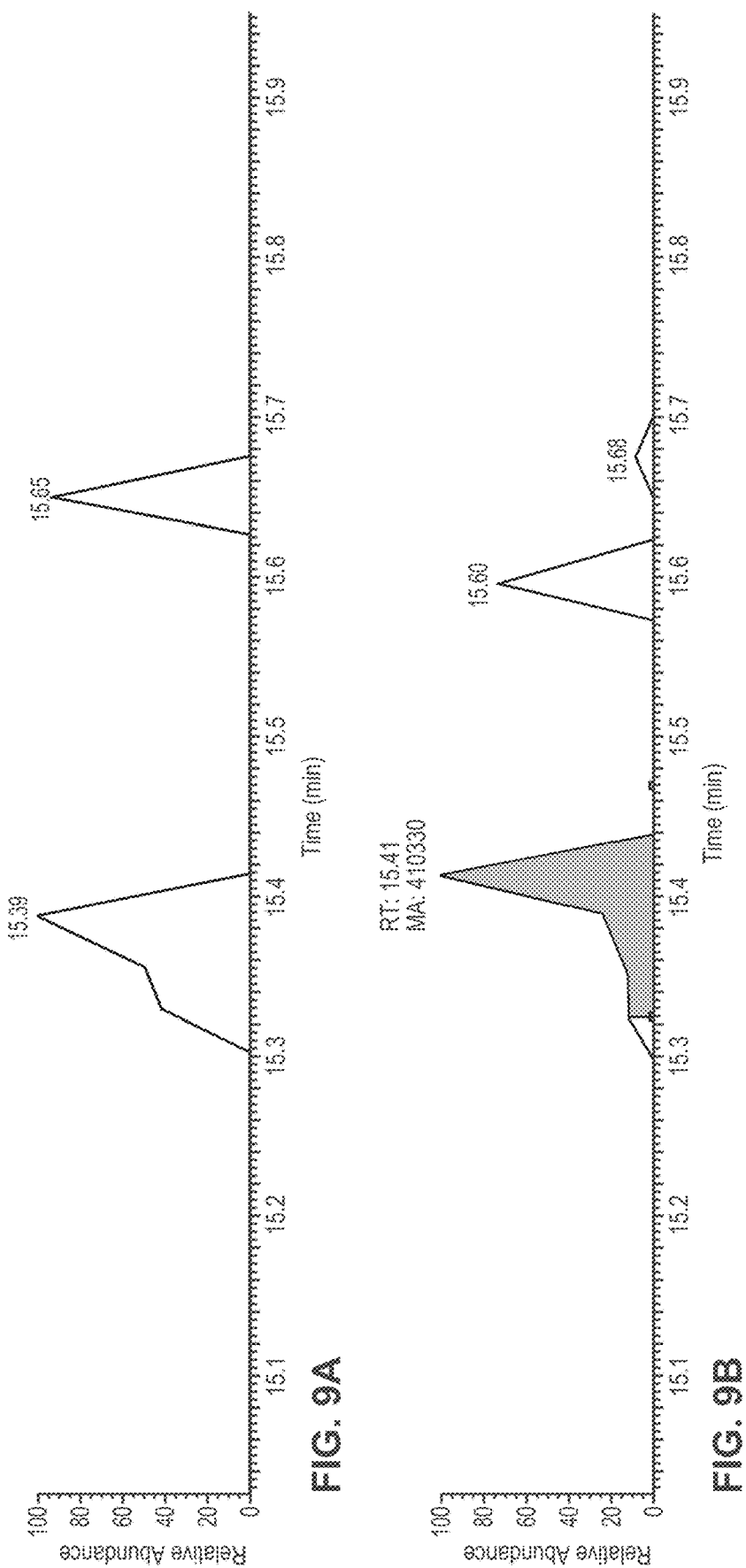

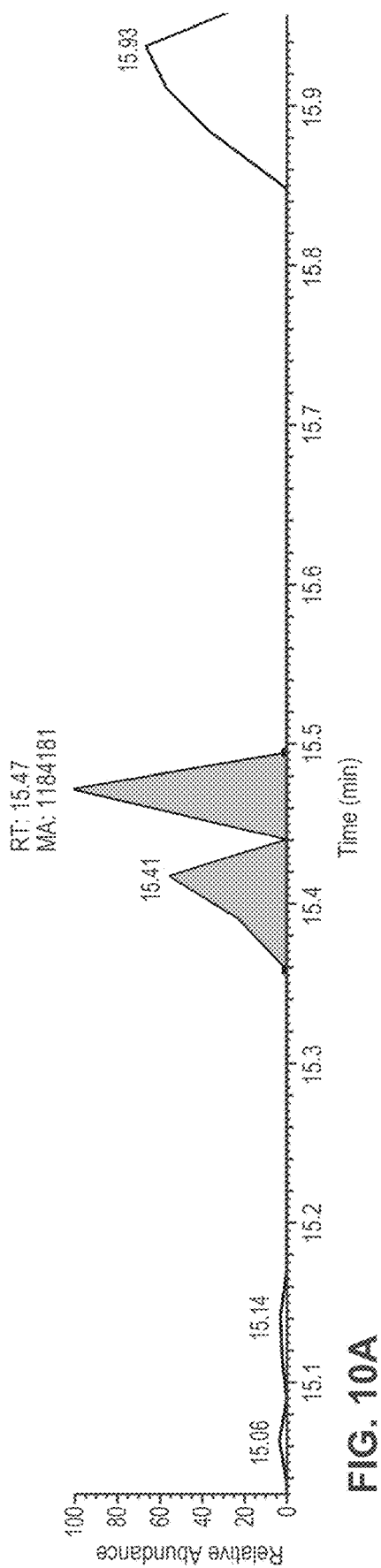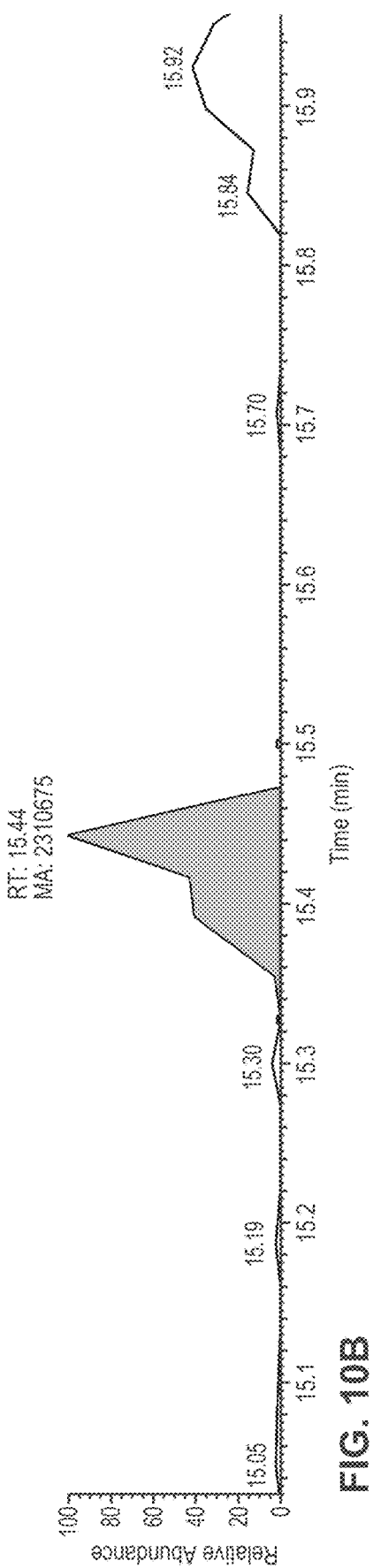
FIG. 10A
FIG. 10B

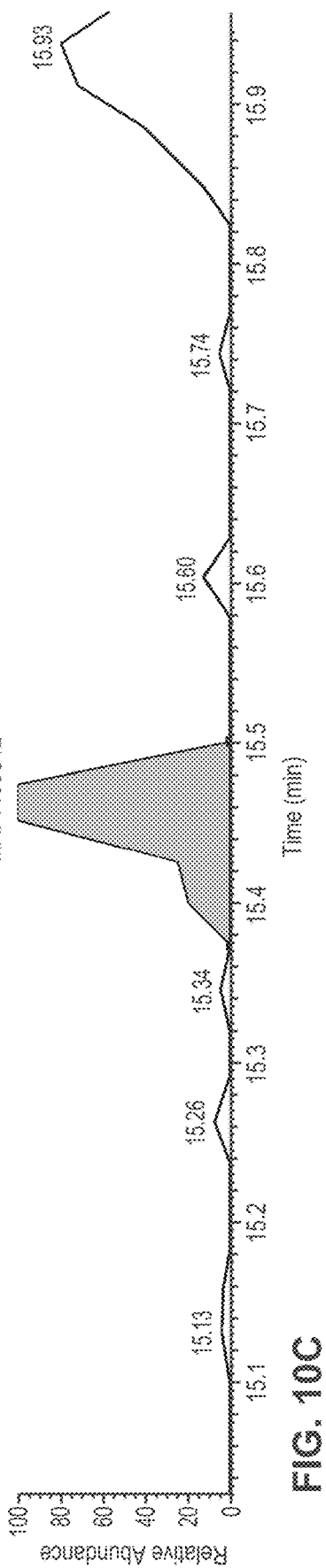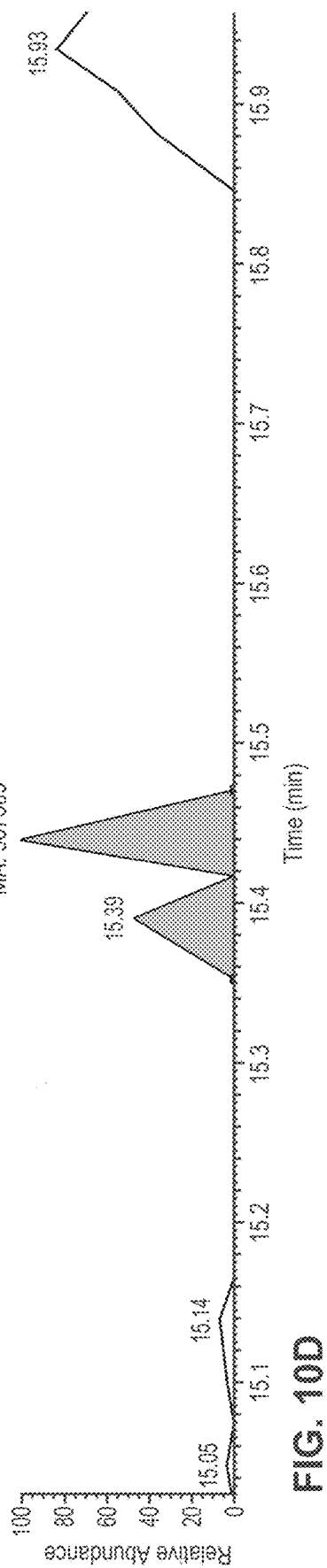

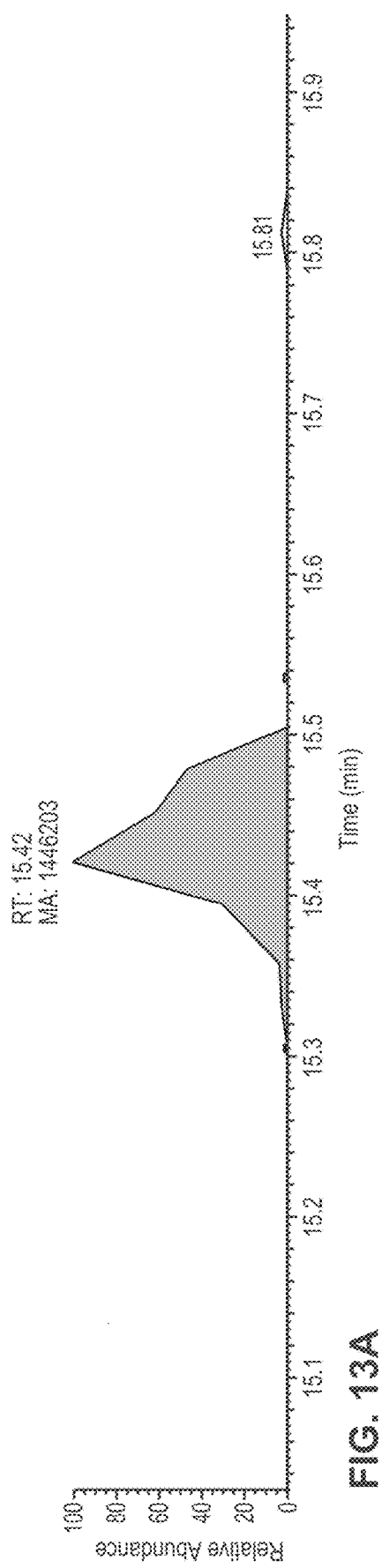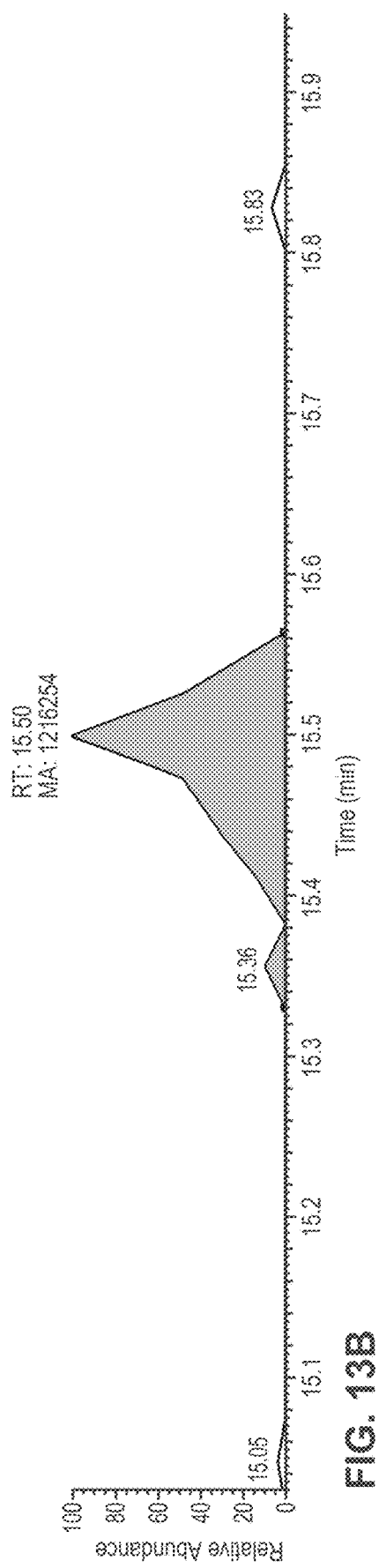
FIG. 13A
FIG. 13B

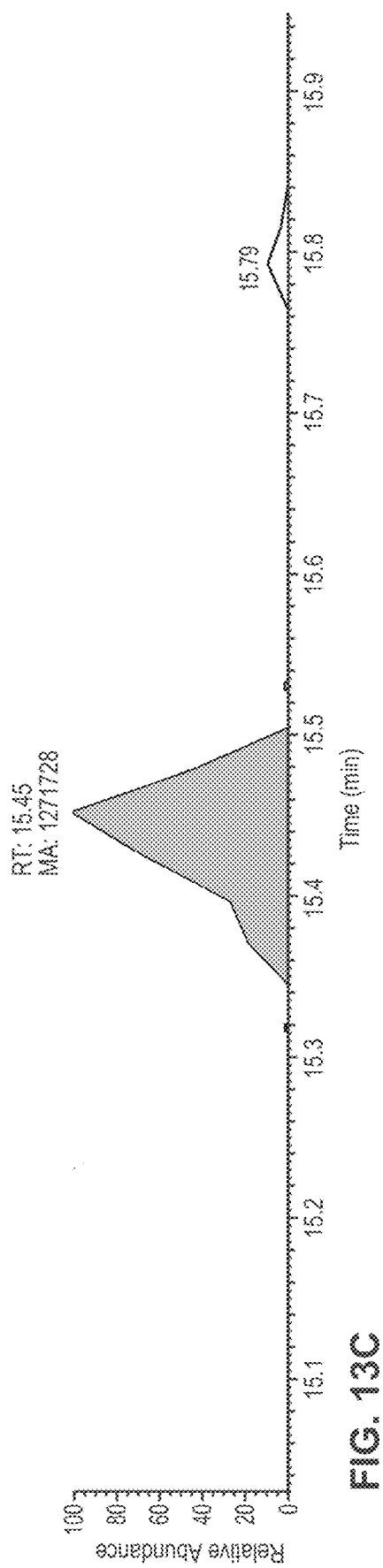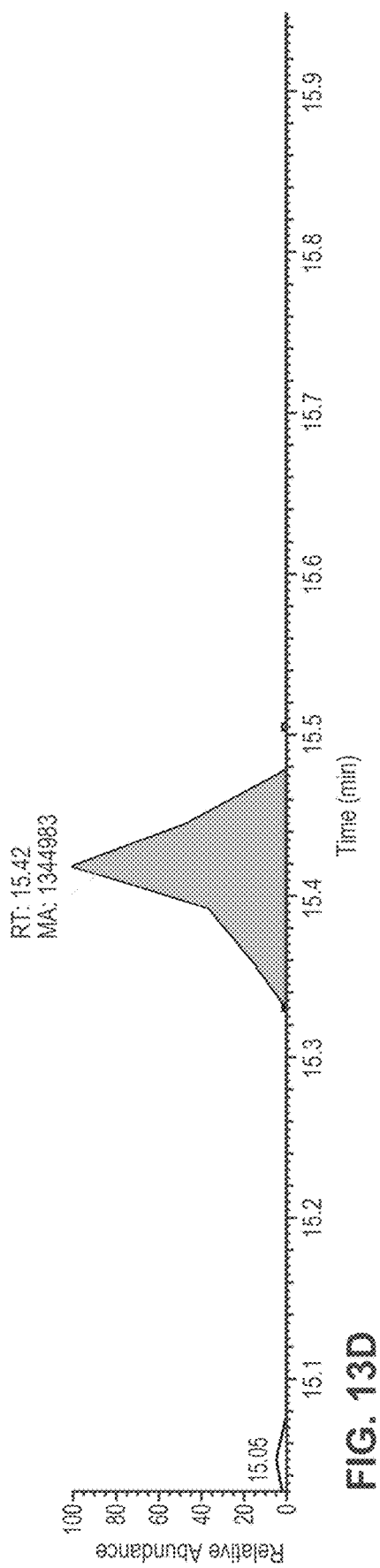

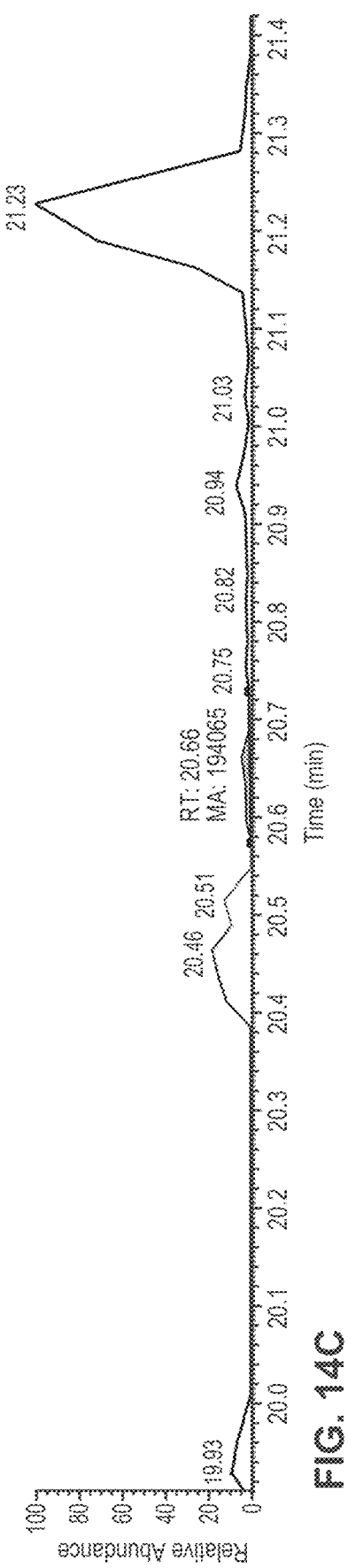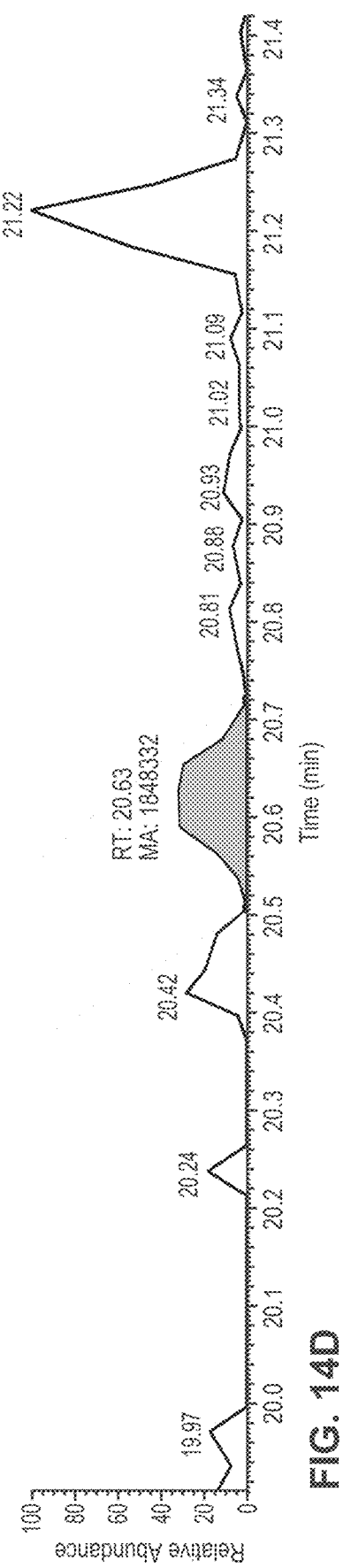
FIG. 14C
FIG. 14D

FIG. 16

Bispecific HC

EVRLVESGGGLVKPGGSLRLSCSASGFDFDNAWMTWVRQPPGKGLEWVGRITGPGEGWSVDYAESVKGRFTISRDNTKNTLYLEMNNVRTEDTGYYFCARTGK
YYDFWSGYFPGEEYFQDWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKP
DWDRSTNTAYLQLSGLTSGDTAVYYCAKGSKHRLRDYALYDDDGALNWAVDVDYLSNLEFWGQGTAVTVSSDKTHTASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYT
LPPCRDELTKNQVSLWCLVKGFYPSDIAVEWESNGQPENNYKTTPPVLDSDGSFFLYSKLTVDKSRWQQGNVFSCSVLHEALHSHYTQKSLSLSPG (SEQ
ID NO: 12)

Bispecific LC

DFVLTQSPHSLSVTPGESASISCKSSHSLIHGDRNNYLAWYQKPGRSPQLLIYLASSRASGVPDRFSGSGSDFTLKISRVETEDVGTYYCMQGRESPWTF
GQGTKVDINDKTHTASELTQDPAVSVALKQTVTITCRGDSLRSHYASWYQKKPGQAPVLLFYGKNNRPSGIPDRFSGSASGNRASLTITGAQAEDEADYYCSS
RDKSGSRLSVFGGGTKLTVLDKTHTRFTVAAPSVFIFPPSDEQLKSGTASVVCLLNNFYPREAKVQWKVDNALQSGNSQESVTEQDSKDSTYSLSSTLTLSKAD
YEKHKVYACEVTHQGLSSPVTKSFNRGEC (SEQ ID NO: 13)

Monospecific HC

QVQLVQSGGGQMKKPGESMRISCRASGYEFIDCTLNWIRLAPGKRFEWMGWLKPRGGAVNYARPLQGRVEMTRDVYSDTAFLELRSLTVDDTAVYFCTRGKNCD
YNWDFEHWGRGTPVIVSSASTKGPSVFPLAPSSKSTSGGTAALGCLVKDYFPEPVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVCTLPPSRDELTKNQVSLSCAVKGFYPSDIAVEWESNGQPENNYKTTPPVLDSDGSFFLVS
KLTVDKSRWQQGNVFSCSVLHEALHSHYTQKSLSLSPG (SEQ ID NO: 14)

Monospecific LC

EIVLTQSPGTLSLSPGETAIISCRTSQYGSLAWYQQRPGQAPRLVIYSGSTRAAGIPDRFSGSRWGPDYNLTISNLESGDFGVYYCQQYEFFGGGTKVQVDIK
RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFN
RGEC (SEQ ID NO: 15)

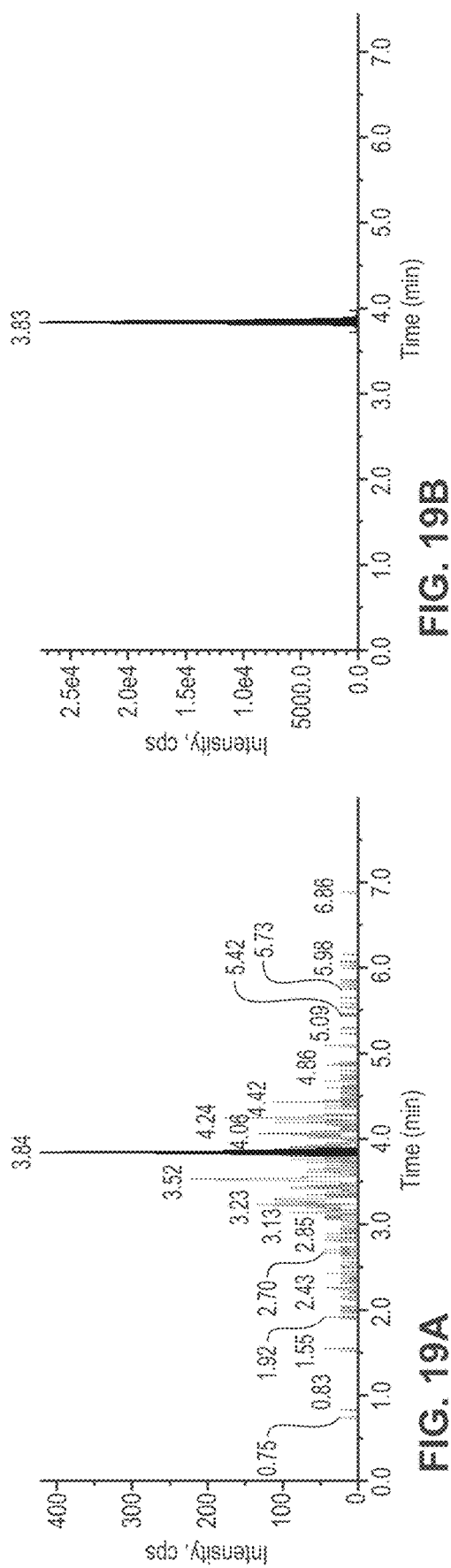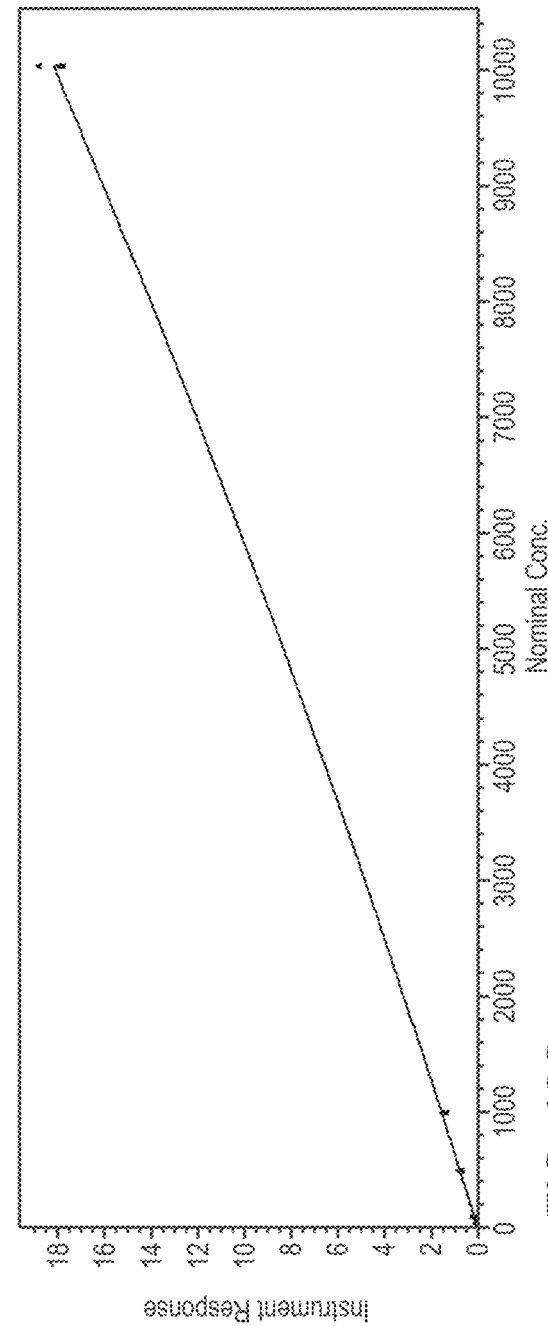
FIG. 19A  FIG. 19B  FIG. 19C

SEQUENCE LISTING

<160> NUMBER OF SEQ ID NOS: 39

<210> SEQ ID NO 1
<211> LENGTH: 225
<212> TYPE: PRT
<213> ORGANISM: Artificial Sequence
<220> FEATURE:
<223> OTHER INFORMATION: Synthetic Construct

<400> SEQUENCE: 1

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

<210> SEQ ID NO 2
<211> LENGTH: 224
<212> TYPE: PRT
<213> ORGANISM: Artificial Sequence
<220> FEATURE:
<223> OTHER INFORMATION: Synthetic Construct

<400> SEQUENCE: 2

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60
```

```
Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
            115                 120                 125

Leu Pro Pro Cys Arg Asp Glu Leu Thr Lys Asn Gln Val Ser Leu Trp
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Leu His Glu
        195                 200                 205

Ala Leu His Ser His Tyr Thr Gln Lys Ser Leu Ser Leu Ser Pro Gly
210                 215                 220
```

<210> SEQ ID NO 3
<211> LENGTH: 224
<212> TYPE: PRT
<213> ORGANISM: Artificial Sequence
<220> FEATURE:
<223> OTHER INFORMATION: Synthetic Construct

<400> SEQUENCE: 3

```
Thr His Thr Cys Pro Pro Cys Pro Ala Pro Glu Leu Leu Gly Gly Pro
1                5                  10                  15

Ser Val Phe Leu Phe Pro Pro Lys Pro Lys Asp Thr Leu Met Ile Ser
                 20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
            115                 120                 125

Leu Pro Pro Ser Arg Asp Glu Leu Thr Lys Asn Gln Val Ser Leu Ser
        130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Val Ser Lys Leu Thr Val Asp Lys
            180                 185                 190

Ser Arg Trp Gln Gln Gly Asn Val Phe Ser Cys Ser Val Leu His Glu
        195                 200                 205
```

```
Ala Leu His Ser His Tyr Thr Gln Lys Ser Leu Ser Leu Ser Pro Gly
    210                 215                 220
```

<210> SEQ ID NO 4
<211> LENGTH: 225
<212> TYPE: PRT
<213> ORGANISM: Artificial Sequence
<220> FEATURE:
<223> OTHER INFORMATION: Synthetic Construct

<400> SEQUENCE: 4

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
        115                 120                 125

Leu Pro Pro Ser Arg Asp Glu Leu Thr Lys Asn Gln Val Ser Leu Ser
    130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

<210> SEQ ID NO 5
<211> LENGTH: 224
<212> TYPE: PRT
<213> ORGANISM: Artificial Sequence
<220> FEATURE:
<223> OTHER INFORMATION: Synthetic Construct

<400> SEQUENCE: 5

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60
```

```
Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Cys Arg Asp Glu Leu Thr Lys Asn Gln Val Ser Leu Trp
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Asp Gly Ser Phe Phe Leu Val Ser
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic Construct

<400> SEQUENCE: 7

Thr Thr Pro Pro Val Leu Asp Ser Asp Gly Ser Phe Phe Leu Val Ser
1               5                   10                  15

Lys

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

Asp Gly Ser Phe Phe Leu Val Ser Lys Leu Thr Val
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 9

Gly Ser Phe Phe Leu Val Ser Lys Leu Thr Val Asp
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic Construct

<400> SEQUENCE: 10

Phe Asn Trp Tyr Val Asp Gly Val Glu Val His Asn Ala Lys
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Ala Leu His Ser His Tyr Thr Gln Lys
1               5

<210> SEQ ID NO 12
<211> LENGTH: 611
<212> TYPE: PRT
<213> ORGANISM: Artificial Sequence
<220> FEATURE:
<223> OTHER INFORMATION: Synthetic Construct

<400> SEQUENCE: 12

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Ser Ser Asp Lys Thr His Thr Gln Val His Leu Thr Gln Ser Gly
    130                 135                 140

Pro Glu Val Arg Lys Pro Gly Thr Ser Val Lys Val Ser Cys Lys Ala
145                 150                 155                 160

Pro Gly Asn Thr Leu Lys Thr Tyr Asp Leu His Trp Val Arg Ser Val
                165                 170                 175

Pro Gly Gln Gly Leu Gln Trp Met Gly Trp Ile Ser His Glu Gly Asp
            180                 185                 190

Lys Lys Val Ile Val Glu Arg Phe Lys Ala Lys Val Thr Ile Asp Trp
```

```
            195                 200                 205
Asp Arg Ser Thr Asn Thr Ala Tyr Leu Gln Leu Ser Gly Leu Thr Ser
210                 215                 220

Gly Asp Thr Ala Val Tyr Tyr Cys Ala Lys Gly Ser Lys His Arg Leu
225                 230                 235                 240

Arg Asp Tyr Ala Leu Tyr Asp Asp Gly Ala Leu Asn Trp Ala Val
                    245                 250                 255

Asp Val Asp Tyr Leu Ser Asn Leu Glu Phe Trp Gly Gln Gly Thr Ala
                260                 265                 270

Val Thr Val Ser Ser Asp Lys Thr His Thr Ala Ser Thr Lys Gly Pro
            275                 280                 285

Ser Val Phe Pro Leu Ala Pro Ser Ser Lys Ser Thr Ser Gly Gly Thr
290                 295                 300

Ala Ala Leu Gly Cys Leu Val Lys Asp Tyr Phe Pro Glu Pro Val Thr
305                 310                 315                 320

Val Ser Trp Asn Ser Gly Ala Leu Thr Ser Gly Val His Thr Phe Pro
                325                 330                 335

Ala Val Leu Gln Ser Ser Gly Leu Tyr Ser Leu Ser Ser Val Val Thr
                340                 345                 350

Val Pro Ser Ser Ser Leu Gly Thr Gln Thr Tyr Ile Cys Asn Val Asn
            355                 360                 365

His Lys Pro Ser Asn Thr Lys Val Asp Lys Val Glu Pro Lys Ser
370                 375                 380

Cys Asp Lys Thr His Thr Cys Pro Pro Cys Pro Ala Pro Glu Leu Leu
385                 390                 395                 400

Gly Gly Pro Ser Val Phe Leu Phe Pro Pro Lys Pro Lys Asp Thr Leu
                405                 410                 415

Met Ile Ser Arg Thr Pro Glu Val Thr Cys Val Val Val Asp Val Ser
                420                 425                 430

His Glu Asp Pro Glu Val Lys Phe Asn Trp Tyr Val Asp Gly Val Glu
            435                 440                 445

Val His Asn Ala Lys Thr Lys Pro Arg Glu Glu Gln Tyr Asn Ser Thr
450                 455                 460

Tyr Arg Val Val Ser Val Leu Thr Val Leu His Gln Asp Trp Leu Asn
465                 470                 475                 480

Gly Lys Glu Tyr Lys Cys Lys Val Ser Asn Lys Ala Leu Pro Ala Pro
                485                 490                 495

Ile Glu Lys Thr Ile Ser Lys Ala Lys Gly Gln Pro Arg Glu Pro Gln
                500                 505                 510

Val Tyr Thr Leu Pro Pro Cys Arg Asp Glu Leu Thr Lys Asn Gln Val
            515                 520                 525

Ser Leu Trp Cys Leu Val Lys Gly Phe Tyr Pro Ser Asp Ile Ala Val
530                 535                 540

Glu Trp Glu Ser Asn Gly Gln Pro Glu Asn Asn Tyr Lys Thr Thr Pro
545                 550                 555                 560

Pro Val Leu Asp Ser Asp Gly Ser Phe Phe Leu Tyr Ser Lys Leu Thr
                565                 570                 575

Val Asp Lys Ser Arg Trp Gln Gln Gly Asn Val Phe Ser Cys Ser Val
                580                 585                 590

Leu His Glu Ala Leu His Ser His Tyr Thr Gln Lys Ser Leu Ser Leu
            595                 600                 605

Ser Pro Gly
610
```

<210> SEQ ID NO 13
<211> LENGTH: 338
<212> TYPE: PRT
<213> ORGANISM: Artificial Sequence
<220> FEATURE:
<223> OTHER INFORMATION: Synthetic Construct

<400> SEQUENCE: 13

```
Asp Phe Val Leu Thr Gln Ser Pro His Ser Leu Ser Val Thr Pro Gly
1               5                   10                  15

Glu Ser Ala Ser Ile Ser Cys Lys Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Asp Lys Thr His Thr Ala Ser Glu Leu Thr Gln Asp Pro Ala Val Ser
        115                 120                 125

Val Ala Leu Lys Gln Thr Val Thr Ile Thr Cys Arg Gly Asp Ser Leu
    130                 135                 140

Arg Ser His Tyr Ala Ser Trp Tyr Gln Lys Lys Pro Gly Gln Ala Pro
145                 150                 155                 160

Val Leu Leu Phe Tyr Gly Lys Asn Asn Arg Pro Ser Gly Ile Pro Asp
                165                 170                 175

Arg Phe Ser Gly Ser Ala Ser Gly Asn Arg Ala Ser Leu Thr Ile Thr
            180                 185                 190

Gly Ala Gln Ala Glu Asp Glu Ala Asp Tyr Tyr Cys Ser Ser Arg Asp
        195                 200                 205

Lys Ser Gly Ser Arg Leu Ser Val Phe Gly Gly Thr Lys Leu Thr
    210                 215                 220

Val Leu Asp Lys Thr His Thr Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
        275                 280                 285

Glu Gln Asp Ser Lys Asp Ser Thr Tyr Ser Leu Ser Ser Thr Leu Thr
    290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335

Glu Cys
```

<210> SEQ ID NO 14
<211> LENGTH: 450

<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
            405                 410                 415

Asp Lys Ser Arg Trp Gln Gln Gly Asn Val Phe Ser Cys Ser Val Leu
        420                 425                 430

His Glu Ala Leu His Ser His Tyr Thr Gln Lys Ser Leu Ser Leu Ser
            435                 440                 445

Pro Gly
    450

<210> SEQ ID NO 15
<211> LENGTH: 210
<212> TYPE: PRT
<213> ORGANISM: Artificial Sequence
<220> FEATURE:
<223> OTHER INFORMATION: Synthetic Construct

<400> SEQUENCE: 15

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Leu Val Ile Tyr Ser Gly Ser Thr Arg
1               5
```

<210> SEQ ID NO 17
<211> LENGTH: 14
<212> TYPE: PRT
<213> ORGANISM: Artificial Sequence
<220> FEATURE:
<223> OTHER INFORMATION: Synthetic Construct

<400> SEQUENCE: 17

Asp Ser Thr Tyr Ser Leu Ser Ser Thr Leu Thr Leu Ser Lys
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Asp Thr Leu Met Ile Ser Arg
1               5

<210> SEQ ID NO 19
<211> LENGTH: 17
<212> TYPE: PRT
<213> ORGANISM: Artificial Sequence
<220> FEATURE:
<223> OTHER INFORMATION: Synthetic Construct

<400> SEQUENCE: 19

Thr Thr Pro Pro Val Leu Asp Ser Asp Gly Ser Phe Phe Leu Tyr Ser
1               5                   10                  15

Lys

<210> SEQ ID NO 20
<211> LENGTH: 18
<212> TYPE: PRT
<213> ORGANISM: Artificial Sequence
<220> FEATURE:
<223> OTHER INFORMATION: Synthetic Construct

<400> SEQUENCE: 20

Leu Thr Thr Pro Pro Val Leu Asp Ser Asp Gly Ser Phe Phe Leu Val
1               5                   10                  15

Ser Lys

<210> SEQ ID NO 21
<211> LENGTH: 4
<212> TYPE: PRT
<213> ORGANISM: Artificial Sequence
<220> FEATURE:
<223> OTHER INFORMATION: Synthetic Construct

<400> SEQUENCE: 21

Gly Gly Gly Gly
1

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

```
Gly Gly Gly Gly Gly
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

Gly Gly Gly Gly Gly Gly
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Gly Gly Gly Gly Gly Gly Gly
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Gly Gly Gly Gly Gly Gly Gly Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Gly Gly Gly Gly Ser
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic Construct

<400> SEQUENCE: 27

Gly Gly Gly Gly Ser Gly Gly Gly Gly Ser
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Synthetic Construct

<400> SEQUENCE: 28
```

Gly Gly Gly Gly Ser Gly Gly Gly Gly Ser Gly Gly Gly Gly Ser
1               5                   10                  15

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Thr Lys Gly Pro Ser
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Construct

<400> SEQUENCE: 30

Thr Val Ala Ala Pro
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct

<400> SEQUENCE: 31

Gln Arg Ile Glu Gly
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Arg Thr Val Ala Ala Pro Ser
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct

<400> SEQUENCE: 33

Gly Gln Pro Lys Ala Ala Pro
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

His Ile Asp Ser Pro Asn Lys

```
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35

Asp Lys Thr His Thr
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic Construct

<400> SEQUENCE: 36

Thr Lys Gly Pro Ser Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Ala Ser Thr Lys Gly Pro Ser
1               5

<210> SEQ ID NO 38
<211> LENGTH: 11
<212> TYPE: PRT
<213> ORGANISM: Artificial Sequence
<220> FEATURE:
<223> OTHER INFORMATION: Synthetic Construct

<400> SEQUENCE: 38

Glu Ser Pro Trp Thr Phe Gly Gln Gly Thr Lys
1               5                   10

<210> SEQ ID NO 39
<211> LENGTH: 5
<212> TYPE: PRT
<213> ORGANISM: Artificial Sequence
<220> FEATURE:
<223> OTHER INFORMATION: Synthetic Construct

<400> SEQUENCE: 39

Gln Pro Lys Ala Ala
1               5
```

METHODS FOR THE QUANTITATION OF POLYPEPTIDES

CROSS-REFERENCE TO RELATED APPLICATIONS

This application is a continuation of U.S. patent application Ser. No. 16/246,376, filed Jan. 11, 2019, which claims the priority benefit of U.S. Provisional Application No. 62/617,080, filed Jan. 12, 2018, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792016801SEQLIST.TXT, date recorded: Jun. 1, 2021, size: 29 KB).

FIELD OF THE INVENTION

The present invention provides methods for quantitating the amount of a polypeptide that comprises an antibody constant region (or portion thereof) with an engineered mutation in a sample.

BACKGROUND OF THE INVENTION

Proteins, such as antibodies, represent a growing class of therapeutics. During pre-clinical development, candidate therapeutic proteins undergo extensive analyses in animal models to assess their pharmacokinetic (PK), pharmacodynamics (PD), and toxicokinetic (TK) characteristics, to assess their safety profiles, and to determine a safe dose for first-in-man studies. During clinical development, the PK, PD, and TK characteristics of therapeutic proteins are analyzed further in human subjects. Data from studies in humans are used to evaluate the safety and efficacy of the therapeutic protein, to establish dosing schedules, and/or to adjust dosages in patient subpopulations. Accordingly, it is critical that methods for quantitating therapeutic proteins in both pre-clinical and clinical samples be reliable and sensitive.

Ligand binding assays (LBAs) have traditionally been employed for quantitation of therapeutic proteins, due to their high sensitivity, low cost, and high throughput. Despite these advantages, LBAs have limited linear dynamic range, carry a risk of cross reactivity across metabolites/analogs, and are difficult to multiplex. Moreover, developing new antibodies for use in LBAs for novel therapeutic proteins is both costly and labor-intensive.

Liquid chromatography tandem mass spectrometry (LC-MS/MS) has emerged as a promising assay platform for quantification of therapeutic proteins. LC-MS/MS assays used for bioanalysis of therapeutic proteins in pre-clinical animal studies frequently rely upon quantification of a "surrogate peptide" (i.e., a peptide whose sequence is unique to the therapeutic protein and absent in the proteomes of pre-clinical species) as a proxy measure of therapeutic protein. Because many therapeutic proteins are derived from human proteins, the sequence of a surrogate peptide will likely be present in the human proteome, thus impeding accurate quantitation of the therapeutic protein in a sample obtained from a human subject.

Accordingly, there remains a need in the art for universal methods for quantification of therapeutic proteins in both pre-clinical (non-human) and clinical (human) samples. The present disclosure is directed to this and other needs.

All references cited in this application are expressly incorporated by reference herein.

BRIEF SUMMARY OF THE INVENTION

Provided is a method for quantitating an amount of a polypeptide comprising a portion of an antibody heavy chain constant region in a sample, the method comprising: (a) digesting the sample comprising the polypeptide comprising the portion of the antibody heavy chain constant region, wherein the portion of the antibody heavy chain constant region comprises an engineered mutation, and wherein digestion produces a peptide fragment derived from the antibody heavy chain constant region that is between 5 and 26 amino acids long and comprises the engineered mutation; and (b) analyzing the digested sample by mass spectrometry to determine quantity of the peptide fragment, thereby determining the quantity of the polypeptide comprising the portion of the antibody heavy chain constant region in the sample. In certain embodiments according to (or as applied to) any of the embodiments above, the peptide fragment does not comprise a methionine (M) or cysteine (C). In certain embodiments according to (or as applied to) any of the embodiments above, the peptide fragment does not comprise an asparagine (N) followed by a glycine (G) or serine (S). In certain embodiments according to (or as applied to) any of the embodiments above, the method further comprises purifying and concentrating the digested sample prior to the mass spectrometry analysis. In certain embodiments according to (or as applied to) any of the embodiments above, the digested sample is purified and concentrated via solid phase extraction (SPE). In certain embodiments according to (or as applied to) any of the embodiments above, the digested sample is purified and concentrated via SISCAPA (Stable Isotope Standards and Capture by Anti-Peptide Antibodies).

In certain embodiments according to (or as applied to) any of the embodiments above, the sample is a whole blood sample, a serum sample, a plasma sample, or a tissue sample. In certain embodiments according to (or as applied to) any of the embodiments above, the sample is from a mouse, a non-human primate, or a human. In certain embodiments according to (or as applied to) any of the embodiments above, the non-human primate is a cynomolgus monkey or a rhesus monkey. In certain embodiments according to (or as applied to) any of the embodiments above, the sample is digested with at least one enzyme. In certain embodiments according to (or as applied to) any of the embodiments above, the at least one enzyme is trypsin, chymotrypsin, glutamyl endopeptidase, lysyl endopeptidase, Asp-N, Arg-C, Glu-C, cyanogen bromide (CnBr), or combinations thereof. In certain embodiments according to (or as applied to) any of the embodiments above, the mass spectrometry used to determine the quantity of the polypeptide in the sample is liquid chromatography-tandem mass spectrometry analysis (LC-MS/MS).

In certain embodiments according to (or as applied to) any of the embodiments above, the polypeptide comprises a CH1 domain, and wherein the CH1 domain comprises the engineered mutation. In certain embodiments according to (or as applied to) any of the embodiments above, the polypeptide comprises a CH2 domain, and wherein the CH2 domain comprises the engineered mutation. In certain embodiments according to (or as applied to) any of the embodiments above, the polypeptide comprises a CH3 domain, and wherein the CH3 domain comprises the engineered mutation. In certain embodiments according to (or as applied to) any of the embodiments above, the engineered mutation in the CH3 domain of the antibody heavy chain constant region is T366Y, T366W, T366S, L368A, T394W, T394S, F405A, F405W, Y407T, Y407V, or Y407A. In certain embodiments according to (or as applied to) any of the embodiments above, the engineered mutation in the CH3 domain of the antibody heavy chain constant region is Y407V, and wherein the CH3 domain comprises an amino acid sequence set forth in SEQ ID NO: 6 (DGSFFLVS). In certain embodiments according to (or as applied to) any of the embodiments above, the digestion produces a peptide fragment comprising (such as consisting of) the amino acid sequence TTPPVLDSDGSFFLVSK (SEQ ID NO: 7), DGSFFLVSKLTV (SEQ ID NO: 8), or GSFFLVSKLTVD (SEQ ID NO: 9). In certain embodiments according to (or as applied to) any of the embodiments above, the sample is digested with trypsin, and wherein the digestion produces a peptide fragment consisting of the amino acid sequence TTPPVLDSDGSFFLVSK (SEQ ID NO: 7). In certain embodiments according to (or as applied to) any of the embodiments above, the sample is digested with Asp-N, and wherein the digestion produces a peptide fragment consisting of the amino acid sequence DGSFFLVSKLTV (SEQ ID NO: 8). In certain embodiments according to (or as applied to) any of the embodiments above, the sample is digested with Glu-C, and wherein the digestion produces a peptide fragment consisting of the amino acid sequence GSFFLVSKLTVD (SEQ ID NO: 9). In certain embodiments according to (or as applied to) any of the embodiments above, the polypeptide comprises the amino acid sequence set forth in SEQ ID NO: 3 or SEQ ID NO: 4. In certain embodiments according to (or as applied to) any of the embodiments above, the engineered mutation in the CH3 domain of the antibody heavy chain constant region is N434S. In certain embodiments according to (or as applied to) any of the embodiments above, the sample is digested with Glu-C and trypsin, and wherein the digestion produces a peptide fragment consisting of the amino acid sequence ALHSHYTQK (SEQ ID NO: 11). In certain embodiments according to (or as applied to) any of the embodiments above, the polypeptide comprises the amino acid sequence set forth in SEQ ID NO: 2 or SEQ ID NO: 3.

In certain embodiments according to (or as applied to) any of the embodiments above, the polypeptide comprising the portion of the antibody heavy chain constant region is an antibody, an Fc-fusion protein, or an immunoadhesin. In certain embodiments according to (or as applied to) any of the embodiments above, the polypeptide comprising the portion of the antibody heavy chain constant region is an antibody. In certain embodiments according to (or as applied to) any of the embodiments above, the antibody is a therapeutic antibody. In certain embodiments according to (or as applied to) any of the embodiments above, the antibody is a chimeric antibody, a humanized antibody, or a human antibody. In certain embodiments according to (or as applied to) any of the embodiments above, the antibody is a monospecific antibody, a bispecific antibody, a trispecific antibody, or a multispecific antibody. In certain embodiments according to (or as applied to) any of the embodiments above, the antibody is a trispecific antibody. In certain embodiments according to (or as applied to) any of the embodiments above, the trispecific antibody comprises four polypeptide chains that form three antigen binding sites that specifically bind one or more antigen targets or target proteins, wherein a first polypeptide comprises a structure represented by the formula: VL2-L1-VL1-L2-CL; the second polypeptide chain comprises a structure represented by the formula: VH1-L3-VH2-L4-CH1-hinge-CH2-CH3; the third polypeptide chain comprises a structure represented by the formula: VH3-CH1-hinge-CH2-CH3; the fourth polypeptide chain comprises a structure represented by the formula: VL3-CL, wherein VL1 is a first immunoglobulin light chain variable domain; VL2 is a second immunoglobulin light chain variable domain; VL3 is a third immunoglobulin light chain variable domain; VH1 is a first immunoglobulin heavy chain variable domain; VH2 is a second immunoglobulin heavy chain variable domain; VH3 is a third immunoglobulin heavy chain variable domain; CL is an immunoglobulin light chain constant domain; CH1 is an immunoglobulin CH1 heavy chain constant domain; and L1, L2, L3 and L4 are amino acid linkers; wherein the first and second polypeptides form a cross-over light chain-heavy chain pair; and wherein the second polypeptide chain or the third polypeptide chain comprises the amino acid sequence TTPPVLDSDGSFFLVSK (SEQ ID NO: 7), DGSFFLVSKLTV (SEQ ID NO: 8), or GSFFLVSKLTVD (SEQ ID NO: 9). In certain embodiments according to (or as applied to) any of the embodiments above, the first polypeptide comprises the amino acid sequence set forth in SEQ ID NO: 12; the second polypeptide comprises the amino acid sequence set forth in SEQ ID NO: 13; the third polypeptide comprises the amino acid sequence set forth in SEQ ID NO: 14, and the fourth polypeptide comprises the amino acid sequence set forth in SEQ ID NO: 15.

In certain embodiments according to (or as applied to) any of the embodiments above, the antibody is conjugated to a drug or a label. In certain embodiments according to (or as applied to) any of the embodiments above, the drug is selected from a chemotherapeutic agent, a cytotoxic agent, or a growth-inhibitory agent. In certain embodiments according to (or as applied to) any of the embodiments above, the label is a radioisotope, a fluorescent dye, or an enzyme. In certain embodiments according to (or as applied to) any of the embodiments above, the antibody is a human IgG antibody. In certain embodiments according to (or as applied to) any of the embodiments above, the IgG antibody is a human IgG1 antibody or a human IgG4 antibody. In certain embodiments according to (or as applied to) any of the embodiments above, the antibody binds A2AR, APRIL, ATPDase, BAFF, BAFFR, BCMA, BlyS, BTK, BTLA, B7DC, B7H1, B7H4/VTCN1, B7H5, B7H6, B7H7, B7RP1, B7-4, C3, C5, CCL2/MCP-1, CCL3/MIP-1a, CCL4/MIP-1b, CCL5/RANTES, CCL7/MCP-3, CCL8/mcp-2, CCL11/eotaxin, CCL15/MIP-1d, CCL17/TARC, CCL19/MIP-3b, CCL20/MIP-3a, CCL21/MIP-2, CCL24/MPIF-2/eotaxin-2, CCL25/TECK, CCL26/eotaxin-3, CCR3, CCR4, CD3, CD19, CD20, CD23/FCER2, CD24, CD27, CD28, CD38, CD39, CD40, CD70, CD80/B7-1, CD86/B7-2, CD122, CD137/41BB, CD137L, CD152/CTLA4, CD154/CD40L, CD160, CD272, CD273/PDL2, CD274/PDL1, CD275/B7H2, CD276/B7H3, CD278/ICOS, CD279/PD-1, CDH1/E-cadherin, chitinase, CLEC9, CLEC91, CRTH2, CSF-1/M-CSF, CSF-2/GM-CSF, CSF-3/GCSF, CX3CL1/SCYD1, CXCL12/SDF1, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb/IL25, IL18, IL22, IL23, IL25, IL27, IL33, IL35, ITGB4/b4 integrin, ITK, KIR, LAGS, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2/receptor for IL33, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP/IL7Ra, TSLPR, TWEAK, VEGF, VISTA, Vstm3, WUCAM, or XCR/GPR5/CCXCR1. In certain embodiments according to (or as applied to) any of the embodiments above, the method is for use in pharmacokinetic study of the polypeptide comprising an antibody heavy chain constant region in a mouse, a non-human primate, and a human.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary. These and other aspects of the invention will become apparent to one of skill in the art. These and other embodiments of the invention are further described by the detailed description that follows.

BRIEF DESCRIPTION OF THE DRAWINGS

FIG. 1 shows sequence alignments of the Fc regions of several exemplary therapeutic antibodies. Predicted tryptic peptides that comprise at least one amino acid substitution are underlined. The cysteines present within tryptic peptides are denoted with thick arrows. SEQ ID NOs: 2 and 5 include the knob mutation T366W. SEQ ID NOs: 3 and 4 comprise the hole mutations T366S, L368A, and Y407V.

FIGS. 2A-2C show the results of LC-MS/MS analysis of a tryptically-digested trispecific construct (TRI-1) that comprises heavy chains with the amino acid sequences set forth in SEQ ID NOs: 2 and 3. SEQ ID NO: 2 comprises the engineered "knob" mutation T366W, and SEQ ID NO: 3 comprises engineered "hole" mutations T366S, L368A, and Y407V. Tryptic digestion of SEQ ID NO: 3 predicted to produce a peptide having the amino acid sequence TTPPVLDSDGSFFLVSK (SEQ ID NO: 7), i.e., the "engineered TTPP peptide". FIG. 2A shows the extracted ion chromatogram for m/z 905.40-907.60. FIG. 2B shows the total ion chromatogram. FIG. 2C shows the MS/MS spectrum of the engineered TTPP peptide.

FIGS. 3A-3D show extracted ion chromatograms of tryptically-digested mouse serum (FIG. 3A), monkey serum (FIG. 3B), human serum (FIG. 3C), and TRI-1 in PBST (FIG. 3D). The runtime for engineered TTPP is denoted by a box.

FIGS. 4A-4D show extracted ion chromatograms of tryptically-digested TRI-1 in mouse serum (FIG. 4A), monkey serum (FIG. 4B), human serum (FIG. 4C), and PBST (FIG. 4D). The runtime for engineered TTPP is denoted by a box.

FIGS. 7A-7C show extracted ion chromatograms of isotopically labeled FNWY (FNWY(Heavy)) from tryptically-digested SILUMAB used as an internal standard for TRI-1 digestion in PBST, m/z=562.58-562.63. TRI-1 concentrations were 20 µg/mL (FIG. 7A), 2 µg/mL (FIG. 7B), and 0.2 µg/mL (FIG. 7C). The peak areas for the FNWY peptide were 1369078 (FIG. 7A), 343482 (FIG. 7B), and 473743 (FIG. 7C).

FIGS. 9A-9D show extracted ion chromatograms of unlabeled FNWY from tryptically-digested TRI-1 in mouse serum, m/z=559.90-559.98. TRI-1 concentrations were 0 µg/mL (control) (FIG. 9A), 0.2 µg/mL (FIG. 9B), 2 µg/mL (FIG. 9C), and 20 µg/mL (FIG. 9D). The peak areas for the FNWY peptide were ND (not detected) (FIG. 9A), 410330 (FIG. 9B), 2500109 (FIG. 9C), and 22039621 (FIG. 9D).

FIGS. 10A-10D show extracted ion chromatograms of FNWY(Heavy) from tryptically-digested SILUMAB used as an internal standard for TRI-1 digestion in mouse serum, m/z=562.58-562.63. TRI-1 concentrations were 0 µg/mL (control) (FIG. 10A), 0.2 µg/mL (FIG. 10B), 2 µg/mL (FIG. 10C), and 20 µg/mL (FIG. 10D). The peak areas for the FNWY peptide were 1184181 (FIG. 10A), 2310675 (FIG. 10B), 1199642 (FIG. 10C), and 967309 (FIG. 10D).

FIGS. 13A-13D show extracted ion chromatograms of FNWY (Heavy) from tryptically-digested SILUMAB used as an internal standard for TRI-1 digestion in monkey serum, m/z=562.58-562.63. TRI-1 concentrations were 0 µg/mL (control) (FIG. 13A), 0.2 µg/mL (FIG. 13B), 2 µg/mL (FIG. 13C), and 20 µg/mL (FIG. 13D). The peak areas for the FNWY peptide were 1446203 (FIG. 13A), 1216254 (FIG. 13B), 1271728 (FIG. 13C), and 1344983 (FIG. 13D).

FIGS. 14A-14D show extracted ion chromatograms of engineered TTPP from tryptically-digested TRI-1 in human serum, m/z=905.39-905.55. TRI-1 concentrations were 0 µg/mL (control) (FIG. 14A), 0.2 µg/mL (FIG. 14B), 2 µg/mL (FIG. 14C), and 20 µg/mL (FIG. 14D). The peak areas for the TTPP peptide were ND (not detected) (FIG. 14A), ND (not detected) (FIG. 14B), 194065 (FIG. 14C), and 1848332 (FIG. 14D).

FIG. 15A shows a comparison of the area ratio of engineered TTPP:FNWY(Heavy) versus antibody concentration of TRI-1 in PBST. FIG. 15B shows a comparison of the area ratio of unlabeled FNWY:FNWY (Heavy) versus antibody concentration of TRI-1 in PBST. FIG. 15C shows a comparison of the area ratio of engineered TTPP:FNWY(Heavy) versus antibody concentration of TRI-1 in mouse serum. FIG. 15D shows a comparison of the area ratio of engineered TTPP:FNWY(Heavy) versus antibody concentration of TRI-1 in monkey serum.

FIG. 16 shows the sequences of the heavy chains and light chains of the exemplary trispecific antibody quantified in Example 2. The sequences of the surrogate peptides quantified in the LC-MS/MS assay are underlined.

FIG. 19A shows an exemplary chromatogram of the TTPP peptide at LLOQ (lowest limit of quantification, 2.5 µg/ml). FIG. 19B shows an exemplary chromatogram of a stable isotope-labeled TTPP peptide (standard [$^{13}$C11-$^{15}$N2]-LTTPPVLDSDGSFFLVSK (SEQ ID NO: 20), which was used as an internal standard in Example 3. FIG. 19C shows a calibration curve of TTPP peptide over the range of 2.5 µg/mL-10,000 µg/mL.

DETAILED DESCRIPTION OF THE INVENTION

Definitions

Figure 3C:
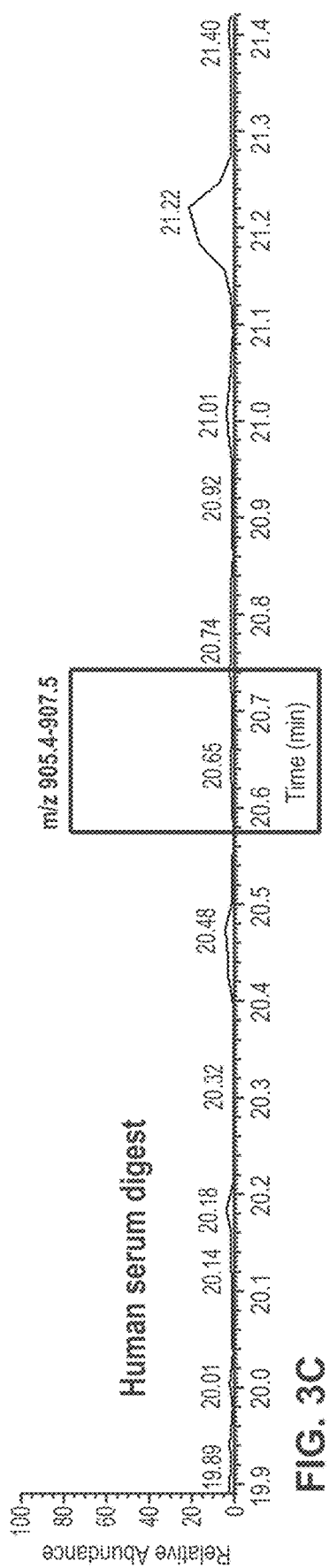

As used herein, an "antibody constant region" refers to the more conserved region of the antibody, e.g., outside the variable domains. The term may include the light chain constant region, i.e., the CL domain, the hinge region, as well as heavy chain constant domains CH1, CH2, CH3 and, optionally, CH4.

As used herein, the term "engineered mutation" refers to refers to a mutation created by human design (i.e., the mutation did not spontaneously occur by natural causes and/or was the result of intentional human manipulation).

As used herein, the term "antibody" may refer to intact antibodies, antibody fragments comprising at least a portion of a heavy chain constant region (including, without limitation, Fab, F(ab')2, Fab'-SH, Fv, scFv, or single heavy chain antibodies), provided that they exhibit the desired biological activity; monoclonal antibodies; polyclonal antibodies; monospecific antibodies; multispecific antibodies (e.g., bispecific antibodies and trispecific antibodies); and antibody-like proteins.

The term "antibody" typically refers to heterotetrameric complexes including two light (L) chains and two heavy (H) chains. Variable numbers of disulfide bonds connect the two heavy chains, and one connects each light chain to a heavy chain, in addition to intrachain disulfide bridges. The heavy chains include a variable domain (VH) followed (N-terminus to C-terminus) by three or four constant domains. The light chains include a variable domain (VL) followed by a constant domain (CL). Typically, mammalian light chains fall into one of two categories based on amino acid sequence: kappa and lambda.

As used herein, the term "multispecific" when used in reference to an antibody or antibody fragment includes an antibody or antibody fragment that possesses two or more different binding specificities (e.g., bispecific and trispecific antibodies). For example, each binding specificity may recognize a different antigen, or each binding specificity may recognize the same antigen with different affinity and/or precise epitope. In some embodiments, each different binding specificity comprises one or more different antibody antigen binding domains (e.g., variable domains), such that the multispecific antibody or antibody fragment comprises, e.g., a first antigen binding domain with a first binding specificity, a second antigen binding domain with a second binding specificity, etc. A variety of exemplary multispecific antibody formats (e.g., bispecific and trispecific antibody formats) are known in the art and described in further detail elsewhere herein.

Before describing the disclosed embodiments in detail, it is to be understood that the present disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

As used herein, the term "about" refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising," "consisting," and "consisting essentially of" aspects and embodiments.

Methods for Quantitating a Polypeptide in a Sample

Mass spectrometry (MS) is a feasible alternative to ligand-binding assays (LBAs) for the quantitative analysis of therapeutic proteins in samples obtained from, e.g., pre-clinical animal studies. The typical procedure for MS-based quantification entails digesting each sample to generate peptide fragments and quantifying the amount of a specific peptide derived from the therapeutic protein as a surrogate for the therapeutic protein itself. Currently, "universal" surrogate peptides derived from the constant region of a human antibody are being used in generic methods for the quantification of human, humanized, or chimeric antibodies in nonhuman animal models. Such generic methods are based on the principle that the sequence of the "universal" surrogate peptide is conserved throughout all human Fc domains, but is absent from species in which preclinical efficacy and safety studies are performed (e.g., mice, rats, dogs, monkeys, etc.). However, it is not possible to use "universal" surrogate peptides to accurately quantitate, e.g., a therapeutic protein comprising a constant region of human antibody, in samples from human patients, as the sequence of the "universal" surrogate peptide is also present in endogenous human antibodies.

Many therapeutic proteins (e.g., antibodies) that comprise a constant region of human antibody also comprise engineered mutations that have been introduced into the constant region in order to, e.g., modulate effector function, modulate serum half-life, promote heterodimerization, etc. Applicants found that peptides derived from the portion of the constant region that contains an engineered mutation are unique in both non-human and human proteome backgrounds. Accordingly, the methods described herein may be used to quantitate therapeutic proteins in both preclinical samples (i.e., obtained from animal species) and clinical samples (i.e., obtained from human patients).

Provided are methods for quantitating an amount of a polypeptide in a sample, wherein the polypeptide comprises a portion of an antibody heavy chain constant region, and wherein the portion of the antibody heavy chain constant region comprises with an engineered mutation. In some embodiments, the method comprises the steps of: (a) digesting a sample that is suspected of comprising the polypeptide to produce a digested sample comprising a peptide fragment that comprises the engineered mutation; and (b) analyzing the digested sample via mass spectrometry to determine a quantity of the peptide fragment that comprises the engineered mutation, thereby determining the quantity of the polypeptide. Polypeptides that may be quantified using the methods described herein (e.g., fusion proteins, immunoadhesins, and antibodies) are described in further detail elsewhere herein.

In some embodiments, the methods provided herein are used in pharmacokinetic studies (such as in preclinical research or in a clinical trial). In some embodiments, the methods comprise the step of administering the polypeptide that comprises a portion of antibody heavy chain constant region with an engineered mutation to an animal, e.g., during pre-clinical research, prior to quantification. Exemplary non-human animals to which the polypeptide that comprises a portion of antibody heavy chain constant region with an engineered mutation may be administered are described in detail below. In some embodiments, the methods comprise administering the polypeptide that comprises a portion of antibody heavy chain constant region with an engineered mutation to a human, e.g., a human patient during a clinical trial, prior to quantification.

In some embodiments, the sample comprising the polypeptide that comprises a portion of antibody heavy chain constant region with an engineered mutation is a biological sample that is derived, obtained, or separated from an animal. In some embodiments, the animal from which the sample is derived, obtained, or separated is an animal to which the polypeptide that comprises a portion of antibody heavy chain constant region with an engineered mutation was administered. In some embodiments, the animal is a mammal. In some embodiments, the mammal is a human (e.g., a human patient), a non-human primate (NHP) (e.g., a cynomolgus monkey, a rhesus monkey, a marmoset, a tamarin, a spider monkey, an owl monkey, a squirrel monkey, a vervet money, a baboon, or others), or a rodent (e.g., a mouse or rat).

In some embodiments, the sample to be analyzed according to a method provided herein is any sample that is suspected to contain the polypeptide that comprises a portion of an antibody heavy chain constant region with an engineered mutation. In some embodiments, the sample is or is derived from a bodily fluid, including, but not limited to, e.g., blood, plasma, serum, milk, bronchial lavage, amniotic fluid, saliva, bile, or tears. In some embodiments, the sample comprises tissue or cells. In some embodiments, the sample comprises serum and a known quantity of the peptide (i.e., "spiked" serum). In some embodiments, the spiked serum further comprises a buffer. In some embodiments, the spiked serum serves as a reference for quantifying the amount of the polypeptide comprising a portion of an antibody heavy chain constant region with an engineered mutation present in a sample derived, obtained, or separated from an animal.

In some embodiments, the method further comprises treating the sample prior to digestion in order to, e.g., enrich the polypeptide that comprises a portion of an antibody heavy chain constant region with an engineered mutation in the sample, or to, e.g., deplete abundant proteins from a sample (such as albumin from a blood, serum, or plasma sample). In some embodiments, treating the sample comprises performing an antibody pull-down assay. Alternatively or additionally, in some embodiments, treating the sample comprises performing gel electrophoresis, extraction, precipitation, centrifugation, chromatography (e.g., affinity capture chromatography, size exclusion chromatography, etc.), ultrafiltration, and/or one or more additional separation steps known to those of ordinary skill in the art.

In some embodiments, the sample is digested via chemical cleavage. Exemplary chemical reagents that cleave at specific sites in polypeptides include, but are not limited to, e.g., formic acid, hydroxylamine, iodosobenzoic acid, and NTCB (2-nitro-5-thiocyanobenzoic acid). In some embodiments, the sample is digested with an enzyme, e.g., an endopeptidase. In some embodiments, the enzyme is a site-specific endopeptidase. Exemplary site-specific proteases include, but are not limited to, trypsin, chymotrypsin (high specificity, cleaves c-terminal to FYW, not before P), chymotrypsin (low specificity, cleaves c-terminal to FYWML, not before P), glutamyl endopeptidase, lysyl endopeptidase, Asp-N protease, Arg-C protease, Lys-C protease, Lys-N protease, *Staphylococcus aureus* V8 (also known as glutamyl endopeptidase or Glu-C protease), cyanogen bromide (CnBr), elastase, pepsin (pH=1.3), pepsin (pH>2), neprilysin, BNPS-skatole, caspase 1, caspase 2, caspase 3, caspase 4, caspase 5, caspase 6, caspase 7, caspase 8, caspase 9, caspase 10, clostripain, enteroinase, Factor Xa, Granzyme B, thermolysin, proline-endopeptidase, *Staphylococcus* peptidase I, thrombin, and Tobacco etch virus protease. In some embodiments, the sample is digested with a non-specific endopeptidase, e.g., papain or proteinase K. In some embodiments, the sample is digested with a mixture comprising two (or more) endopeptidases (including site-specific and/or non-site-specific). In some embodiments, the two or more endopeptidases are used simultaneously to digest the sample. In some embodiments, the two or more endopeptidases are used sequentially to digest the sample. Methods for digesting polypeptides in preparation for analysis via mass spectrometry are well known in the art. Exemplary methods are provided in, e.g., Gundry et al. (2009) *Curr Protoc Mol Biol*. doi: 10.1002/0471142727.mb1025s88; Hedrick et al. (2015) *Curr Protoc Chem Biol*. 7(3): 201-222; Giansanti et al. (2016) *Nature Protocols*. 11: 993-1006; Nordhoff et al. (*Int J Mass Spect*. 226(1): 163-180; and Zhang et al. (2014) *Curr Protoc Mol Biol*. doi: 10.1002/0471142727.mb1021s108.

Digestion of the sample produces a peptide fragment that comprises the engineered mutation. In some embodiments the peptide fragment produced by the digestion is between 5 and 40 amino acids in length, e.g. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids in length. In some embodiments, the peptide fragment does not comprise cysteine (Cys) and/or methionine (M) residues. Alternatively or additionally, in some embodiments, the peptide does not comprise an asparagine residue (N) followed by a glycine residue (G) or a serine residue (S) (i.e., NG or NS). In some embodiments, the peptide fragment does not comprise adjacent endopeptidase cleavage sites, e.g., two or more site-specific endopeptidase cleavage sites separated by 6, 5, 4, 3, 2, or 1 amino acids. A variety of in silico tools have been developed to predict the peptide populations that can be produced via digestion (e.g., digestion with a single enzyme or chemical cleavage reagent or a digestion with a combination of enzymes and/or chemical cleavage reagents). Such tools, which include (without limitation) PChopper, PeptideCutter, MAPPP, IPEP, MS-Digest, and Protein Digestion Simulator, are well known in the art and are publicly available, such as on the World Wide Web.

In some embodiments, the method further comprises purifying and/or concentrating the digested sample prior to analysis via mass spectrometry. In some embodiments, purifying and/or concentrating the digested sample comprises performing an affinity capture chromatography or a solid-phase extraction (SPE), and eluting a purified and concentrated sample. (See, e.g., Gudry et al. (2009) "Preparation of Proteins and Peptides for Mass Spectrometry Analysis in a Bottom-Up Proteomics Workflow." Curr Protoc Mol Biol. CHAPTER: Unit10.25. doi:10.1002/0471142727.mb1025s88.) In some embodiments, purifying and/or concentrating the digested sample comprises performing a Stable Isotope Standards and Capture by Anti-Peptide Antibodies (SISCAPA). In some embodiments, the sample is subjected to an antibody pull-down assay, digested (e.g., using one or more endopeptidases known in the art), and purified and/or concentrated via SISCAPA. Details regarding SISCAPA are provided in, e.g., Anderson et al. (2004) "Mass spectrometric quantitation of peptides and proteins using Stable Isotope Standards and Capture by Anti-Peptide Antibodies (SISCAPA). *J Proteome Res*. 3(2): 235-44; U.S. Pat. Nos. 7,632,686 and 9,164,089; Whiteaker et al. (2011) "Evaluation of large scale quantitative proteomic assay development using peptide affinity-based mass spectrometry." Mol Cell Proteomics. 10(4):M110.005645; and Rasavi et al. (2016) "Multiplexed longitudinal measurement of protein biomarkers in DBS using an automated SISCAPA workflow." *Bioanalysis*. 8(15):1597-1609.

In some embodiments the digested sample is analyzed via liquid chromatography-tandem mass spectrometry (LC-MS/MS). LC-MS/MS is a method where a sample mixture is first separated by liquid chromatography before being ionized (e.g., via electrospray ionization (ESI), atmospheric pressure chemical ionization (APCI), or atmospheric pressure photoionization (APPI)) and characterized by mass-to-charge ratio and relative abundance using two mass spectrometers in series. Details regarding LC-MS/MS are provided in, e.g., Grebe et al. (2011) "LC-MS/MS in the Clinical Laboratory—Where to From Here?" *Clin. Biochem Review*. 32(1): 5-31; El-Khoury et al. "Liquid Chromatography-Tandem Mass Spectrometry in the Clinical Laboratory." *J. Chrom. & Separation Tech*. 4:e115. doi: 10.4172/2157-7064.1000e115; Shushan et al. (2010) "A review of clinical diagnostic applications of liquid chromatography-tandem mass spectrometry." *Mass Spec. Rev*. 29:930-944, 2010.

In some embodiments, the methods provided herein can be used to detect the peptide in a sample, wherein the concentration of the peptide in the sample is any one of about 200, 150, 100, 50, 15, 10, 5, 1, 0.5, 0.25, 0.1, 0.075, 0.05, 0.025, or 0.01 ng/ml, including any range in between these values.

Engineered Mutations in an Antibody Heavy Chain Constant Region

In some embodiments, polypeptide quantitated according to a method provided herein comprises a CH1 domain (or a portion thereof, e.g., between 10 and 50 amino acids) that comprises an engineered mutation. In some embodiments, the CH1 domain extends from about residue 114 to about residue 223 of the antibody heavy chain, according to the Kabat numbering system. In some embodiments, the CH1 domain extends from about residue 118 to about residue 215 of the antibody heavy chain, according to the EU numbering system. See, e.g., International Immunogenetics Information System (IMGT) Web Resources at WorldWideWeb.imgt.org/IMGTScientificChart/Numbering/Hu_IGHGnber.html. These amino acid residue positions are based on human IgG; however, it is not intended that methods provided herein be limited to use with polypeptides comprising the CH1 domain (or portion thereof) of a human IgG. Corresponding CH1 domain sequences from other human Igs, and corresponding CH1 domain sequences of other mammals (e.g., macaque, cynomolgus monkey, mouse, rat, etc.) are publicly available.

In certain embodiments, the engineered mutation in the CH1 domain (or portion thereof) comprises (such as consists of) an amino acid substitution, insertion, or deletion that does not affect (or substantially affect) the desired activity of the polypeptide comprising the antibody heavy chain constant region. In some embodiments, a substitution or insertion comprises the substitution or insertion of an unnatural amino acid or a conjugated amino acid. The amino acid substitution, insertion, or deletion can be introduced into the CH1 domain (or portion thereof) by altering the nucleic acid encoding the polypeptide (e.g. by site-specific mutagenesis) or by peptide synthesis, as described in further detail elsewhere herein.

In certain embodiments, the polypeptide to be quantitated according to a method provided herein comprises a human IgG1 CH1 domain (or portion thereof). In some embodiments, the engineered mutation in the human IgG1CH1 domain (or portion thereof) drives Fc heterodimerization (e.g., for the production of bispecific antibodies, multispecific antibodies, or one-armed antibodies). In some embodiments, the engineered mutation in the human IgG1 CH1 domain (or portion thereof) is an amino acid substitution at K147 or K213 (according to the EU numbering system). In some embodiments, the engineered mutation in the human IgG1 CH1 domain comprises (such as consists of) the amino acid substitution K147D, K147E, K213D, or K213E (according to the EU numbering system).

In certain embodiments, the polypeptide to be quantitated according to a method provided herein comprises a CH2 domain (or a portion thereof, e.g., between 10 and 50 amino acids) that comprises an engineered mutation. In some embodiments, the CH2 domain of a human IgG extends from about residue 231 to about residue 340 of the antibody heavy chain, according to the EU numbering system. See, e.g., International Immunogenetics Information System (IMGT) Web Resources at WorldWideWeb.imgt.org/IMGT-ScientificChart/Numbering/Hu_IGHGnber.html. These amino acid positions are based on human IgG; however, is not intended that methods provided herein be limited to use with polypeptides comprising the CH2 domain (or portion thereof) of a human IgG. Corresponding CH2 domain sequences from other human Igs are publicly available, as are the corresponding CH2 domain sequences of other mammals (e.g., macaque, cynomolgus monkey, rat, mouse, etc.). In certain embodiments, the engineered mutation in the CH2 domain (or portion thereof) comprises an amino acid substitution, insertion, or deletion that does not affect (or substantially affect) the desired activity of the polypeptide comprising the antibody heavy chain constant region. In some embodiments, a substitution or insertion comprises the substitution or insertion of an unnatural amino acid or a conjugated amino acid.

In certain embodiments, the polypeptide to be quantitated according to a method provided herein comprises a human IgG1 CH2 domain (or portion thereof). In some embodiments, the engineered mutation in the human IgG1 CH2 domain (or portion thereof) modulates effector function. In some embodiments, the engineered mutation in the human IgG1 CH2 domain (or portion thereof) comprises an amino acid substitution at one (or more) the following residues: E233, L234, L235, G236, P238, S239, F243, T250, M252, S254, T256, P257, S267, R292, Q295, N297, S298, T299, Y300, Q311, K322, A327, L328, P329, A330, P331, I332, and E333 (according to the EU numbering system). In some embodiments, the engineered mutation in the human IgG1 CH2 domain (or portion thereof) comprises one (or more) of the following amino acid substitutions: E233P, L234V, L234A, L235V, L235A, G236A, P238D, S239D, F243L, T250Q, T250R, M252Y, S254T, T256E, P257I, S267E, R292P, Q295R, N297Q, N297D, N297A, S298G, S298N, S298C, S298A, S28T, T299A, Y300L, Q311I, K322A, A327G, L328E, L328F, L328W, P329G, P329N, A330S, A330L, A330V, P331S, P331V, I332E, I332Y, E333A, and E333S (according to the EU numbering system). Alternatively or additionally, the engineered mutation in the human IgG1 CH2 domain (or portion thereof) comprises (such as consists of) ΔG236 (according to the EU numbering system).

In certain embodiments, the polypeptide to be quantitated according to a method provided herein comprises a human IgG2 CH2 domain (or portion thereof). In some embodiments, the engineered mutation in the human IgG2 CH2 domain (or portion thereof) modulates effector function. In some embodiments, the engineered mutation in the human IgG2 CH2 domain (or portion thereof) comprises an amino acid substitution at one (or more) of the following residues: K326 and E333 (according to the EU numbering system). In some embodiments, the engineered mutation in the human IgG1 CH2 domain (or portion thereof) comprises one (or more) of the following amino acid substitutions: K326W and E333S (according to the EU numbering system).

In certain embodiments, the polypeptide to be quantitated according to a method provided herein comprises a human IgG3 CH2 domain. In some embodiments, the engineered mutation in the human IgG3 CH2 domain modulates effector function. In some embodiments, the engineered mutation in the human IgG3 CH2 domain comprises an amino acid substitution at E235 (according to the EU numbering system). In some embodiments, amino acid substitution comprises E235Y.

In certain embodiments, the polypeptide to be quantitated according to a method provided herein comprises a human IgG4 CH2 domain (or portion thereof). In some embodiments, the engineered mutation in the human IgG4 CH2 domain (or portion thereof) modulates effector function. In some embodiments, the engineered mutation in the human IgG4 CH2 domain (or portion thereof) comprises an amino acid substitution at one (or more) the following residues: S228, F234, L235, F296, G327, and P329 (according to the EU numbering system). In some embodiments, amino acid substitution comprises one (or more) of the following amino acid substitutions: S228P, F234A, F234L, L235A, F296Y, G327A, P329G, and P329N.

In some embodiments, polypeptide to be quantitated according to a method provided herein comprises a CH3 domain (or a portion thereof, e.g., between 10 and 50 amino acids) that comprises an engineered mutation. In some embodiments, the CH3 domain extends from about residue 341 to about residue 447, according to the EU numbering system. See, e.g., International Immunogenetics Information System (IMGT) Web Resources at WorldWideWeb.imgt.org/IMGTScientificChart/Numbering/Hu_IGHGnber-.html. These amino acid positions are based on human IgG; however, is not intended that methods provided herein be limited to use with polypeptides comprising the CH3 domain of a human IgG. Corresponding CH3 domain sequences from other human Igs are publicly available, as are the corresponding CH3 domain sequences from other Igs of other mammals (e.g., macaque, cynomolgus monkey, rat, mouse, etc.). In certain embodiments, the engineered mutation in the CH3 domain (or portion thereof) is an amino acid substitution, insertion, or deletion that does not affect (or substantially affect) the desired activity of the polypeptide comprising the antibody heavy chain constant region. In some embodiments, a substitution or insertion comprises the substitution or insertion of an unnatural amino acid or a conjugated amino acid.

In certain embodiments, the polypeptide to be quantitated according to a method provided herein comprises a human IgG4 CH3 domain (or portion thereof). In some embodiments, the engineered mutation in the human IgG1 CH4 domain (or portion thereof) modulates effector function. In some embodiments, the engineered mutation in the human IgG1 CH3 domain (or portion thereof) comprises (such as consists of) an amino acid substitution at residues R409 (according to the EU numbering system). In some embodiments, the engineered mutation in the human IgG1 CH3 domain (or portion thereof) comprises (such as consists of) the amino acid substitution R409K.

In certain embodiments, the polypeptide to be quantitated according to a method provided herein comprises a human IgG1 CH3 domain (or portion thereof). In some embodiments, the engineered mutation in the human IgG1 CH3 domain (or portion thereof) modulates effector function and/or improves serum half-life. In some embodiments, the engineered mutation in the human IgG1 CH3 domain (or portion thereof) comprises an amino acid substitution at one or more) of the following residues: N343, E380, E382, P396, M428, H433, N434, and Y436 (according to the EU numbering system). In some embodiments, the engineered mutation in the human IgG1 CH3 domain (or portion thereof) comprises one (or more) of following amino acid substitutions: N343A, E380A, E382V, P396L, M428I, M428L, H433K, N434S, N434F, and Y436H (according to the EU numbering system). In some embodiments, the engineered mutation in the human IgG1CH3 domain (or portion thereof) drives Fc heterodimerization (e.g., for the production of bispecific antibodies, multispecific antibodies, or one-armed antibodies). In some embodiments, the engineered mutation in the human IgG1 CH3 domain (or portion thereof) comprises an amino acid substitution one (or more) of the following residues: Y349, 5354, R355, D356, E357, K360, T366, L368, K370, K392, T394, D399, F405, Y407, K409, and K439 (according to the EU numbering system). In some embodiments, the engineered mutation in the human IgG1 CH3 domain (or portion thereof) comprises one (or more) of the following amino acid substitutions: Y349C, S354C, R355D, R355E, D356K, D356R, E357K, E357R, K360D, K360E, T366R, T366K, T366N, T366Q, T366Y, T366W, T366S, T366E, T366G, L368A, L368K, L368Q, L368D, L368E, L368G, L368H, L368I, L368N, L368R, L368S, L368T, L368V, L368W, K370W, K370D, K370E, K392D, K392E, T394W, T394S, D399A, D399G, D399I, D399L, D399M, D399N, D299S, D399T, D399F, D399H, D399K, D399R, D399Y, F405A, F405W, Y407T, Y407V, Y407A, K409R, K409A, K409H, K409D, K409E, K409G, K439D, and K439E (according to the EU numbering system).

In some embodiments, the engineered mutation in the human IgG1 CH3 domain (or portion thereof) comprises (such as consists of) Y407V In some embodiments, the polypeptide comprising an antibody heavy chain constant region with an engineered mutation comprises an amino acid sequence set forth in SEQ ID NO: 6 (DGSFFLVS). In some embodiments, digestion of a sample comprising (or suspected of comprising) a polypeptide comprising an antibody heavy chain constant region with an engineered Y407V mutation produces a peptide fragment comprising (such as consisting of) the amino acid sequence TTPPVLDSDGSF-FLVSK (SEQ ID NO: 7), DGSFFLVSKLTV (SEQ ID NO: 8), or GSFFLVSKLTVD (SEQ ID NO: 9). In some embodiments, the sample comprising (or suspected of comprising) a polypeptide comprising an antibody heavy chain constant region with an engineered Y407V mutation is digested with trypsin, and digestion produces a peptide fragment comprising (such as consisting of) the amino acid sequence TTPPVLDSDGSFFLVSK (SEQ ID NO: 7). In some embodiments, the sample comprising (or suspected of comprising) a polypeptide comprising an antibody heavy chain constant region with an engineered Y407V mutation is digested with Asp-N, and digestion produces a peptide fragment comprising (such as consisting of) the amino acid sequence DGSFFLVSKLTV (SEQ ID NO: 8). In some embodiments, the sample comprising (or suspected of comprising) a polypeptide comprising an antibody heavy chain constant region with an engineered Y407V mutation is digested with Glu-C, and digestion produces a peptide fragment comprising (such as consisting of) the amino acid sequence GSFFLVSKLTVD (SEQ ID NO: 9).

In some embodiments, the engineered mutation in the human IgG1 CH3 domain comprises (such as consists of) N434S. In some embodiments, the sample comprising (or suspected of comprising) a polypeptide comprising an antibody heavy chain constant region with an engineered N434S mutation is digested with Glu-C and trypsin, and digestion produces a peptide fragment comprising (such as consisting of) the amino acid sequence ALHSHYTQK (SEQ ID NO: 11).

In certain embodiments, the engineered mutation is introduced into the antibody heavy chain constant region (or portion thereof) via standard molecular biological techniques known in the art. A variety of methods for genetic engineering have been previously described. Such mutagenesis methods include, but are not limited to, e.g., error-prone PCR, loop shuffling, oligonucleotide-directed mutagenesis, random nucleotide insertion or other methods prior to recombination. Further details regarding these methods are described in, e.g., Abou-Nadler et al. (2010) *Bioengineered Bugs.* 1, 337-340; Firth et al. (2005) *Bioinformatics.* 21, 3314-3315; Cirino et al. (2003) *Methods Mol Biol.* 231, 3-9; Pirakitikulr (2010) *Protein Sci.* 19, 2336-2346; Steffens et al. (2007) *J. Biomol Tech.* 18, 147-149; and others.

Polypeptides Comprising a Portion of an Antibody Heavy Chain Constant Region

The methods provided herein can be performed using any polypeptide that comprises a portion of an antibody heavy chain constant region, wherein the portion of the antibody heavy chain constant region comprises an engineered mutation. In some embodiments, the polypeptide comprises all or a portion (e.g., 10 to 50 amino acids) of a CH1 domain, CH2 domain, and/or CH3 domain, provided that the domain(s) (or portion(s) thereof) comprise an engineered mutation (e.g., an engineered mutation described elsewhere herein). In some embodiments, the portion of the heavy chain constant domain comprising an engineered mutation is or is derived from a mammal (e.g., a human, a non-human primate, a mouse, a rat, etc.). In some embodiments, the portion of the heavy chain constant region that comprises an engineered mutation is or is derived from a human IgG (such as an IgG1, IgG2, IgG3, or IgG4), a human IgA (such as an IgA1 or IgA2), a human IgM, a human IgE, or a human IgD. In some embodiments, the portion of the heavy chain constant region that comprises an engineered mutation is or is derived from a mouse (such as a mouse IgA, IgD, IgE, IgG1, IgG2a, IgG2b, IgG2c, IgG3, or IgM antibody heavy chain constant region).

In certain embodiments, the polypeptide comprising a portion of antibody heavy chain constant region with an engineered mutation is an antibody. In some embodiments, the antibody is a human, humanized, or chimeric antibody. In some embodiments the antibody comprises a constant region of, e.g., a human IgG1, human IgG2, human IgG3, human IgG4, human IgA1, human IgA2, human IgM, human IgE, or human IgD, that comprises at least one engineered mutation.

In certain embodiments, the polypeptide comprising a portion of antibody heavy chain constant region with an engineered mutation is a fusion polypeptide. In some embodiments, the fusion polypeptide is an Fc-fusion polypeptide, which comprises the Fc domain (i.e., the CH2 and CH3 domains) of an antibody heavy chain constant region. In some embodiments, the fusion polypeptide is an immunoadhesin, i.e., a fusion polypeptide in which the functional domain of a binding protein (e.g., a receptor, ligand, or cell-adhesion polypeptide) is fused to a portion of an antibody heavy chain constant region (typically the hinge and Fc domain).

Antibodies

In some embodiments, the polypeptide comprising a portion of an antibody heavy chain constant region that comprises an engineered mutation is an antibody. In some embodiments, the antibody is a heterotetrameric complex that comprises two light (L) chains and two heavy (H) chains. In some embodiments, the two light chains and the two heavy chains are identical. In some embodiments, the two light chains comprise different amino acid sequences. In some embodiments, the two heavy chains comprise different amino acid sequences. In some embodiments, the antibody is a full length antibody (e.g., comprising two full-length light chains and two full-length heavy chains). In some embodiment, the antibody is an antibody fragment that comprises a portion of a heavy chain constant domain that comprises an engineered mutation, e.g., a Fab, a F(ab')2, a Fab'-SH, an Fv, an scFv, or a single heavy chain antibody. In certain embodiments, the antibody is mammalian antibody (such as a human antibody, a non-human primate antibody, a mouse antibody, a rat antibody, etc.). In some embodiments, the antibody is a monospecific antibody. In some embodiments, the antibody is a multispecific antibody.

Multispecific Antibodies

Multispecific antibodies possess binding specificities against more than one antigen (e.g., two, three, or more than three binding specificities). In some embodiments, the antibody quantified using a method provided herein is a bispecific antibody. In some embodiments, a bispecific antibody comprises two different binding specificities for the same antigen (e.g., having different binding affinity and/or specific epitope of the same antigen). In some embodiments, a bispecific antibody comprises binding specificities for two different antigens. In some embodiments, the bispecific antibody is a full-length or intact antibody. The methods provided herein are contemplated for use with bispecific or multispecific antibody formats known in the art. Exemplary bispecific and multispecific antibody formats include, but are not limited to, those described below.

For example, "knobs-into-holes" is a design strategy for engineering antibody heavy chain homodimers for heterodimerization (e.g., for the production of bispecific antibodies, multispecific antibodies, or one-armed antibodies). Generally, such technology involves introducing a protuberance ("knob") at the interface of a first polypeptide (such as a first CH3 domain in a first antibody heavy chain) and a corresponding cavity ("hole") in the interface of a second polypeptide (such as a second CH3 domain in a second antibody heavy chain), such that the protuberance can be positioned in the cavity so as to promote heterodimer formation and hinder homodimer formation. Protuberances are constructed by replacing small amino acid side chains from the interface of the first polypeptide (such as a first CH3 domain in a first antibody heavy chain) with larger side chains (e.g. arginine, phenylalanine, tyrosine or tryptophan). Compensatory cavities of identical or similar size to the protuberances are created in the interface of the second polypeptide (such as a second CH3 domain in a second antibody heavy chain) by replacing large amino acid side chains with smaller ones (e.g. alanine, serine, valine, or threonine). See, e.g., U.S. Pat. Nos. 5,731,168; 5,807,706; 5,821,333; 7,642,228; 7,695,936; 8,216,805; and 8,679,785, the contents of each of which are incorporated by reference herein in their entirety. Exemplary sets of knobs-into-holes mutations include, but not limited to, those shown in Table 1 below:

370, 399, 405, and 407 (according to EU numbering) in each CH3 domain. The mutations drive directional "Fab-arm" or "half-molecule" exchange between two monospecific IgG1, IgG4 or IgG4-like antibodies upon incubation under reducing conditions.

US 2009/0232811 and Schaefer et al. (2011) *PNAS USA.* 108(27): 11187-11192 describe Crossmab technology, i.e., a bispecific antibody format that involves exchanging one or more heavy chain and light chain domains within the antigen-binding fragment (Fab) of one half of the bispecific antibody. Correct association of the light chains and their cognate heavy chains is achieved by exchange of heavy-chain and light-chain domains within the antigen binding fragment (Fab) of one half of the bispecific antibody. This "crossover" retains the antigen-binding affinity but makes the two arms so different that light-chain mispairing can no longer occur. Exemplary Crossmab formats include Crossmab$^{Fab}$ (i.e., in which the CL and VL domains are exchanged with the CH1 and VH domains, respectively), Crossmab$^{VH-VL}$ (i.e., in which the VL and VH domains are exchanged), and Crossmab$^{CH1-VCL}$ (i.e., in which the CH1 and CL domains are exchanged). See also WO 2009/080251, WO 2009/080252, WO 2009/080253, and WO 2009/080254, the contents of each of which is incorporated herein by reference in their entirety.

WO 2007/147901 describes a strategy for engineering antibody heavy chains for heterodimerization (e.g., for the production of bispecific antibodies, multispecific antibodies, or one-armed antibodies) that entails introducing asymmetrical mutations in the Fc domains (i.e., K253E, D282K, K322D into a first Fc domain and D239K, E240K, and K292D into a second Fc domain) and in the CH/CL domains (i.e., K96E in the CH1 and E15K in the CL). Such asymmetrical mutations are reported to both disrupt ionic interactions that stabilize homodimerization of half-antibodies and promote heterodimerization of Fc domains.

WO 2009/089004 describes heteromultimeric proteins (e.g., bispecific, multispecific, or one-armed antibodies) comprising asymmetrical pairs of mutations in the CH3-CH3 interface that make Fc homodimerization electrostatically unfavorable but make Fc heterodimerization electrostatically favorable. See, e.g., Tables 2a and 2b in WO 2009/089004).

Several antibody-like-proteins with CODV (cross-over dual variable) are described in Steinmetz et al. (2016) *MABS.* 8(5): 867-878, WO 2012/135345, WO2016/116626 and U.S. Pat. Nos. 9,181,349 9,221,917, the contents of each of which is incorporated herein by reference in their entirety. CODV architecture results in a circular, self-contained structure functioning as a self-supporting truss that maintains the parental antibody affinities for both antigens. A CODV antibody-like protein may be (a) bivalent and/or bispecific; (b) trivalent and/or trispecific; (c) trivalent and/or bispecific;

TABLE 1

| Exemplary Sets of "Knobs-into-Holes" Mutations | | | | | | | | | | |
|---|---|---|---|---|---|---|---|---|---|---|
| Fc domain monomer 1 | Y407T | Y407A | F405A | T394S | T366S L368A Y407V | T394W Y407T | T394S Y407A | T366W T394S | S354C T366W | S354C T366W |
| Fc domain monomer 2 | T366Y | T366W | T394W | F405W | T366W | T366Y F405A | T366W F405W | F405W Y407A | Y349C T366S L368A Y407V | Y349C T366S L368A Y407A |

WO 2011/131746 describes a bispecific antibody comprising asymmetrical mutations at one of positions 366, 368, or (d) tetravalent and/or bispecific. In one exemplary format, the polypeptide comprises two polypeptide chains having a structure represented by the formula: $V_{L1}$-$L_1$-$V_{L2}$-$L_2$-$C_L$, and two polypeptide chains have a structure represented by the formula: $V_{H2}$-$L_3$-$V_{H1}$-$L_4$-$C_{H1}$-Fc, wherein $V_{L1}$ is a first immunoglobulin light chain variable domain; $V_{L2}$ is a second immunoglobulin light chain variable domain; $V_{H1}$ is a first immunoglobulin heavy chain variable domain; $V_{H2}$ is a second immunoglobulin heavy chain variable domain; $C_L$ is an immunoglobulin light chain constant domain; $C_{H1}$ is the immunoglobulin $C_{H1}$ heavy chain constant domain; Fc comprises an immunoglobulin hinge region and $C_{H2}$, $C_{H3}$ immunoglobulin heavy chain constant domains; $L_1$, $L_2$, $L_3$, and $L_4$ are amino acid linkers; and wherein the polypeptides of formula I and the polypeptides of formula II form a cross-over light chain-heavy chain pair. In another exemplary format, the polypeptide comprises two polypeptide chains that form two antigen binding sites, wherein the first polypeptide has a structure represented by the formula: $V_{L1}$-$L_1$-$V_{L2}$-$L_2$-$C_L$-Fc, and the second polypeptide chain has a structure represented by the formula: $V_{H2}$-$L_3$-$V_{H1}$-$L_4$-$C_{H1}$-Fc, wherein: $V_{L1}$ is a first immunoglobulin light chain variable domain; $V_{L2}$ is a second immunoglobulin light chain variable domain; $V_{H1}$ is a first immunoglobulin heavy chain variable domain; $V_{H2}$ is a second immunoglobulin heavy chain variable domain; CL is an immunoglobulin light chain constant domain; $C_{H1}$ is the immunoglobulin CH1 heavy chain constant domain; $C_{H2}$ is an immunoglobulin $C_{H2}$ heavy chain constant domain; $C_{H3}$ is an immunoglobulin $C_{H3}$ heavy chain constant domain; Fc comprises an immunoglobulin hinge region and $C_{H2}$, $C_{H3}$ immunoglobulin heavy chain constant domains; and $L_1$, $L_2$, $L_3$, and $L_4$ are amino acid linkers; wherein the first and second polypeptides form a cross-over light chain-heavy chain pair. In a third exemplary format, the polypeptide comprises three polypeptide chains that form two antigen binding sites, wherein the first polypeptide chain has a structure represented by the formula: $V_{L1}$-$L_1$-$V_{L2}$-$L_2$-$C_L$, the second polypeptide chain has a structure represented by the formula: $V_{H2}$-$L_3$-$V_{H1}$-$L_4$-$C_{H1}$-Fc, the third polypeptide chain comprises an antibody Fc region, wherein: $V_{L1}$ is a first immunoglobulin light chain variable domain; $V_{L2}$ is a second immunoglobulin light chain variable domain; $V_{H1}$ is a first immunoglobulin heavy chain variable domain; $V_{H2}$ is a second immunoglobulin heavy chain variable domain; CL is an immunoglobulin light chain constant domain; $C_{H1}$ is the immunoglobulin CH1 heavy chain constant domain; $C_{H2}$ is an immunoglobulin $C_{H2}$ heavy chain constant domain; $C_{H3}$ is an immunoglobulin $C_{H3}$ heavy chain constant domain; Fc comprises an immunoglobulin hinge region and $C_{H2}$, $C_{H3}$ immunoglobulin heavy chain constant domains; and $L_1$, $L_2$, $L_3$, and $L_4$ are amino acid linkers; wherein the first and second polypeptides form a cross-over light chain-heavy chain pair. In a fourth exemplary format, the polypeptide comprises a first polypeptide chain comprising a structure represented by the formula: $V_{L1}$-$L_1$-$V_{L2}$-$L_2$-$C_L$ and a second polypeptide chain comprising a structure represented by the formula: $V_{H2}$-$L_3$-$V_{H1}$-$L_4$-$C_{H1}$ wherein: $V_{L1}$ is a first immunoglobulin light chain variable domain; $V_{L2}$ is a second immunoglobulin light chain variable domain; $V_{H1}$ is a first immunoglobulin heavy chain variable domain; $V_{H2}$ is a second immunoglobulin heavy chain variable domain; $C_L$ is an immunoglobulin light chain constant domain; $C_{H1}$ is an immunoglobulin $C_{H1}$ heavy chain constant domain; and $L_1$, $L_2$, $L_3$ and $L_4$ are amino acid linkers; wherein the polypeptide of formula I and the polypeptide of formula II form a cross-over light chain-heavy chain pair.

A bispecific tetravalent immunoglobulin known as the tetravalent bispecific tandem immunoglobulin (TBTI) or dual variable domain immunoglobulin (DVD-Ig) was first described in Wu et al. (2007) *Nat Biotechnol.* 25:1290-7. Like a conventional IgG, a TBTI-DVD-Ig comprises two heavy chains and two light chains. However, both heavy and light chains of a TBTI-DVD-Ig comprise an additional variable domain connected via a flexible, naturally occurring linker sequence at the N-termini of the VH and VL of an existing monoclonal antibody. Accordingly, when the heavy and the light chains combine, the resulting TBTI-DVD-Ig comprises four antigen recognition sites. See also U.S. Pat. Nos. 9,029,508; 9,109,026; 9,035,027; 9,046,513, 8,388,965; 9,732,162; 9,738,728; European Patent No. 2573121 B1, as well as WO2012/135345, the contents of each of which is incorporated herein by reference in their entirety.

US 2017/00320967 and WO 2017/180913, the contents of which are expressly incorporated herein by reference in their entireties, describe a binding protein (such as a trivalent and/or trispecific antibody) comprising four polypeptide chains that form three antigen binding sites. In some embodiments, the binding protein is trivalent. In some embodiments, the binding protein is trispecific. In one exemplary format, the first polypeptide chain comprises a structure represented by the formula: $V_{L2}$-$L_1$-$V_{L1}$-$L_2$-CL; the second polypeptide chain comprises a structure represented by the formula: $V_{H1}$-$L_3$-$V_{H2}$-$L_4$-$C_{H1}$-hinge-$C_{H2}$-$C_{H3}$; the third polypeptide chain comprises a structure represented by the formula: $V_{H3}$-$C_{H1}$-hinge-$C_{H2}$-$C_{H3}$; the fourth polypeptide chain comprises a structure represented by the formula: $V_{L3}$-CL, wherein $V_{L1}$ is a first immunoglobulin light chain variable domain; $V_{L2}$ is a second immunoglobulin light chain variable domain; $V_{L3}$ is a third immunoglobulin light chain variable domain; $V_{H1}$ is a first immunoglobulin heavy chain variable domain; $V_{H2}$ is a second immunoglobulin heavy chain variable domain; $V_{H3}$ is a third immunoglobulin heavy chain variable domain; $C_L$ is an immunoglobulin light chain constant domain; $C_{H1}$ is an immunoglobulin $C_{H1}$ heavy chain constant domain; and $L_1$, $L_2$, $L_3$ and $L_4$ are amino acid linkers; wherein the first and second polypeptides form a cross-over light chain-heavy chain pair; and wherein the second polypeptide chain or the third polypeptide chain comprises the amino acid sequence TTPPVLDSDGSFFLVSK (SEQ ID NO: 7), DGSFFLVSK-LTV (SEQ ID NO: 8), or GSFFLVSKLTVD (SEQ ID NO: 9).

In some embodiments, the linkers $L_1$, $L_2$, $L_3$, and $L_4$ range from no amino acids (length=0) to about 100 amino acids long, or less than 100, 50, 40, 30, 20, or 15 amino acids or less. The linkers can also be 10, 9, 8, 7, 6, 5, 4, 3, 2, or 1 amino acids long. $L_1$, $L_2$, $L_3$, and $L_4$ in one binding protein may all have the same amino acid sequence or may all have different amino acid sequences.

Examples of suitable linkers include a single glycine (Gly) residue; a diglycine peptide (Gly-Gly); a tripeptide (Gly-Gly-Gly); a peptide with four glycine residues (Gly-Gly-Gly-Gly; SEQ ID NO: 21); a peptide with five glycine residues (Gly-Gly-Gly-Gly-Gly; SEQ ID NO: 22); a peptide with six glycine residues (Gly-Gly-Gly-Gly-Gly-Gly; SEQ ID NO: 23); a peptide with seven glycine residues (Gly-Gly-Gly-Gly-Gly-Gly-Gly; SEQ ID NO: 24); a peptide with eight glycine residues (Gly-Gly-Gly-Gly-Gly-Gly-Gly-Gly; SEQ ID NO: 25). Other combinations of amino acid residues may be used such as the peptide Gly-Gly-Gly-Gly-Ser (SEQ ID NO: 26), the peptide Gly-Gly-Gly-Gly-Ser-Gly-Gly-Gly-Gly-Ser (SEQ ID NO: 27) and the peptide Gly-Gly-Gly-Gly-Ser-Gly-Gly-Gly-Gly-Ser-Gly-Gly-Gly-Gly-Ser (SEQ ID NO: 28). Other suitable linkers include a single Ser, and Val residue; the dipeptide Arg-Thr, Gln-Pro, Ser-Ser, Thr- Lys, and Ser-Leu; Thr-Lys-Gly-Pro-Ser (SEQ ID NO: 29), Thr-Val-Ala-Ala-Pro (SEQ ID NO: 30), Gln-Pro-Lys-Ala-Ala (SEQ ID NO: 39), Gln-Arg-Ile-Glu-Gly (SEQ ID NO: 31); Ala-Ser-Thr-Lys-Gly-Pro-Ser (SEQ ID NO: 37), Arg-Thr-Val-Ala-Ala-Pro-Ser (SEQ ID NO: 32), Gly-Gln-Pro-Lys-Ala-Ala-Pro (SEQ ID NO: 33), and His-Ile-Asp-Ser-Pro-Asn-Lys (SEQ ID NO: 34). The examples listed above are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the binding proteins.

The identity and sequence of amino acid residues in the linker may vary depending on the type of secondary structural element necessary to achieve in the linker. For example, glycine, serine, and alanine are best for linkers having maximum flexibility. Some combination of glycine, praline, threonine, and serine are useful if a more rigid and extended linker is necessary. Any amino acid residue may be considered as a linker in combination with other amino acid residues to construct larger peptide linkers as necessary depending on the desired properties.

In some embodiments, the length of $L_1$ is at least twice the length of $L_3$. In some embodiments, the length of $L_2$ is at least twice the length of $L_4$. In some embodiments, the length of $L_1$ is at least twice the length of $L_3$, and the length of $L_2$ is at least twice the length of $L_4$. In some embodiments, $L_1$ is 3 to 12 amino acid residues in length, $L_2$ is 3 to 14 amino acid residues in length, $L_3$ is 1 to 8 amino acid residues in length, and $L_4$ is 1 to 3 amino acid residues in length. In some embodiments, $L_1$ is 5 to 10 amino acid residues in length, $L_2$ is 5 to 8 amino acid residues in length, $L_3$ is 1 to 5 amino acid residues in length, and $L_4$ is 1 to 2 amino acid residues in length. In some embodiments, $L_1$ is 7 amino acid residues in length, $L_2$ is 5 amino acid residues in length, $L_3$ is 1 amino acid residue in length, and $L_4$ is 2 amino acid residues in length.

In some embodiments, $L_1$, $L_2$, $L_3$, and/or $L_4$ comprise the sequence Asp-Lys-Thr-His-Thr (SEQ ID NO: 35). In some embodiments, $L_1$ comprises the sequence Asp-Lys-Thr-His-Thr (SEQ ID NO: 35). In some embodiments, $L_3$ comprises the sequence Asp-Lys-Thr-His-Thr (SEQ ID NO: 35).

In some embodiments, $L_1$, $L_2$, $L_3$, and/or $L_4$ comprise the sequence Gly-Gln-Pro-Lys-Ala-Ala-Pro (SEQ ID NO: 33). In some embodiments, $L_1$ comprises the sequence Gly-Gln-Pro-Lys-Ala-Ala-Pro (SEQ ID NO: 33). In some embodiments, $L_1$ comprises the sequence Gly-Gln-Pro-Lys-Ala-Ala-Pro (SEQ ID NO: 33), $L_2$ comprises the sequence Thr-Lys-Gly-Pro-Ser-Arg (SEQ ID NO: 36), $L_3$ comprises the sequence Ser, and $L_4$ comprises the sequence Arg-Thr. In some embodiments, $L_3$ comprises the sequence Gly-Gln-Pro-Lys-Ala-Ala-Pro (SEQ ID NO: 33). In some embodiments, $L_1$ comprises the sequence Ser, $L_2$ comprises the sequence Arg-Thr, $L_3$ comprises the sequence Gly-Gln-Pro-Lys-Ala-Ala-Pro (SEQ ID NO: 33) and $L_4$ comprises the sequence Thr-Lys-Gly-Pro-Ser-Arg (SEQ ID NO: 36).

In some embodiments, the first polypeptide comprises the amino acid sequence set forth in SEQ ID NO: 12; the second polypeptide comprises the amino acid sequence set forth in SEQ ID NO: 13; the third polypeptide comprises the amino acid sequence set forth in SEQ ID NO: 14, and the fourth polypeptide comprises the amino acid sequence set forth in SEQ ID NO: 15. (SEQ ID NOs: 12, 13, 14, and 15 correspond to SEQ ID NOs: 3, 4, 1, and 2 disclosed in WO 2017/074878, respectively.) The amino acid sequences of additional exemplary trispecific antibodies are described in WO 2017/074878, the contents of which are incorporated herein by reference in their entirety.

The strand-exchange engineered domain (SEED) platform, designed to generate asymmetric and bispecific antibody-like molecules, is based on exchanging structurally related sequences of immunoglobulin within the conserved CH3 domains. Alternating sequences from human IgA and IgG in the SEED CH3 domains generate two asymmetric but complementary domains, designated AG and GA. The SEED design allows efficient generation of AG/GA heterodimers and disfavors the formation of AG/AG and GA/GA homodimers. See, e.g., Muda et al. (2011) *Prot Engineering, Design & Selection.* 24(5): 447-454 and U.S. Pat. No. 8,871,912, the contents of which are incorporated herein by reference in their entirety.

Other bispecific and multispecific antibody formats are described Klein et al., (2012) *mAbs* 4:6, 653-663; Spiess et al. (2015) "Alternative molecular formats and therapeutic applications for bispecific antibodies." *Mol. Immunol.* 67(2 Pt A): 95-106; Egan et al. (2017) mAbs. 9(1):68-84; Liu et al. (2017) *Front Immunol.* 8: 38; and Weidle et al. (2013) *Cancer Genomics Proteomics.* 10(1): 1-18.

Target Antigens

In certain embodiments, a polypeptide to be quantified according to a method provided herein (i.e., a polypeptide comprising a portion of an antibody heavy chain constant region that comprises an engineered mutation) specifically binds to a target antigen. Exemplary target antigens include, without limitation, A2AR, APRIL, ATPDase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAGS, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1). In some embodiments, one or more of the above antigen targets are human antigen targets. In embodiments wherein the polypeptide comprising an antibody heavy chain constant region that comprises an engineered mutation is a bispecific or multispecific target binding protein, the target antigens may be any two (or more) of the exemplary antigens listed above.

Conjugates

In some embodiments, a polypeptide to be quantified according to a method provided herein (i.e., a polypeptide comprising an antibody heavy chain constant region that comprises an engineered mutation) is conjugated to a drug, e.g., a cytotoxic agent, a chemotherapeutic agent, a growth inhibitory agent, a toxin (e.g., an enzymatically active toxin of bacterial, fungal, plant, or animal origin, or fragments thereof). Exemplary drugs include, without limitation, daunomycin, doxorubicin, methotrexate, vindesine, BCNU, streptozoicin, vincristine, and 5-fluorouracil. Exemplary toxins include, without limitation, diphtheria A chain, non-binding active fragments of diphtheria toxin, exotoxin A chain (from *Pseudomonas aeruginosa*), ricin, geldanamycin, maytansine (or other maytansinoids), auristatins, dolastatin, calicheamicin, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, tricothecenes, and CC1065. Cytotoxic agents and linkers that conjugate the agents to an antibody are known in the art; see, e.g., Parslow, A. C. et al. (2016) *Biomedicines* 4:14 and Kalim, M. et al. (2017) *Drug Des. Devel. Ther.* 11:2265-2276.

In some embodiments, a polypeptide to be quantified according to a method provided herein (i.e., a polypeptide comprising an antibody heavy chain constant region that comprises an engineered mutation) is conjugated to detectable moiety that is capable of producing, either directly or indirectly, a detectable signal. In certain embodiments, the detectable label is a radionuclide. A variety of radionuclides are available for the production of radioconjugated polypeptides for use in clinical and research purposes. Examples include $^{13}C$, $^{15}N$, $^{17}O$, $^{19}F$, $^{32}P$, $^{90}Y$, $^{99m}Tc$, $^{111}In$, $^{123}I$, $^{125}I$, $^{131}I$, $^{131}In$, $^{153}Sm$, $^{186}Re$, $^{188}Re$, $^{211}At$, $^{212}Bi$, $^{212}Pb$, and radioactive isotopes of Lu, Mn, Fe, and Gd. In certain embodiments, the detectable label is a fluorescent or chemiluminescent compound, such as fluorescein isothiocyanate, rhodamine, or luciferin; or an enzyme, such as alkaline phosphatase, β-galactosidase, or horseradish peroxidase.

The foregoing written description is considered to be sufficient to enable one skilled in the art to practice the invention. The following Examples are offered for illustrative purposes only, and are not intended to limit the scope of the present invention in any way. Indeed, various modifications in addition to those shown and described herein will become apparent to those skilled in the art from the foregoing description and fall within the scope of the appended claims.

EXAMPLES

Example 1: Identifying a Surrogate Peptide for Use in a Generic Mass Spectrometry-Based Assay for Detecting a Polypeptide Comprising an Antibody Heavy Chain Constant Region in a Sample The following selection criteria were applied to identify a surrogate peptide for the detection of a therapeutic antibody in a biological sample via mass spectrometry:

A length between 6 and 26 amino acids;
No adjacent endopeptidase cleavage sites;
No methionine (M) or cysteine (C) in the peptide sequence;
No asparagine followed by glycine or serine (i.e., NG or NS) in peptide sequence;
Is derived from the constant region of an antibody heavy chain; and
Contains at least one engineered substitution mutation (i.e., excluding naturally occurring polymorphisms).

First, the Fc sequences of three exemplary therapeutic antibodies were aligned. See FIG. 1. SEQ ID NO: 1 is a portion of an anti-Target A antibody heavy chain. SEQ ID NO: 1 does not comprise an engineered mutation. SEQ ID NO: 2 is a portion of a first chain (i.e., "chain 1") of a trispecific construct (i.e., "TRI-1"). TRI-1-chain 1 comprises an antibody heavy chain that comprises S354C and T366W mutations (i.e., "knob" mutations) and M428L/N434S mutations (which extend the in vivo half-life of TRI-1). SEQ ID NO: 3 is a portion of a second chain (i.e., "chain 2) chain of TR1. TRI-1-chain 2 comprises an antibody heavy chain that comprises Y349C/T366S/368A/407 V "hole" mutations and M428L/N434S mutations. SEQ ID NO: 4 is a portion of a first chain (i.e., "chain 1") of a second trispecific construct (i.e., "TRI-2"). TRI-2-chain 1 comprises an antibody heavy chain that comprises Y349C/T366S/368A/407 V mutations (i.e., "hole" mutations) and M428L/N434S mutations. SEQ ID NO: 5 is a portion of a second chain (i.e., "chain 2) of TR2. TRI-2-chain 2 comprises a heavy chain that comprises S354C/T366W "knob" mutations and M428L/N434S mutations. All amino acid positions discussed above are numbered according to the EU numbering scheme.

Candidate peptides containing at least one engineered substitution mutation that were predicted to result from tryptic digestion of the sequences shown in FIG. 1 are underlined. The peptide TTPPVLDSDGSFFLVSK (SEQ ID NO: 7), met all the criteria listed above.

Next, BLAST searches were performed using TTPPVLDSDGSFFLVSK (SEQ ID NO: 7), i.e., the "engineered TTPP peptide," as a query sequence against mouse, cynomolgus monkey, and human protein databases to determine whether such sequence is found in any native proteins in these species. The only sequences exhibiting 100% amino acid identity to the engineered TTPP peptide were known knob-in-hole antibodies. Other sequences that exhibited 94% amino acid identity to the engineered TTPP peptide corresponded to human Fc domains containing Y407 substitution mutations other than Y407V and endogenous human Fc domains.

The experiments described below were performed to assess the feasibility with which trypsin digestion of the trispecific construct TRI-1 gave rise to the engineered TTPP peptide. Briefly, 10 μg of TRI-1 (which comprises SEQ ID NOs: 2 and 3 shown in FIG. 1) was digested using the SMART™ Digest Kit (ThermoFisher) according to manufacturer's instructions. The digestion reaction was incubated at 70° C. while being shaken at 1400 rpm for 75 minutes. The digested sample was then centrifuged at 1000×g for 2 min, and the supernatant was collected for purification and concentration.

The required number of wells in a SOLAμ HRP solid phase extraction (SPE) plate (ThermoFisher) were equilibrated with 200 μL of acetonitrile and then conditioned with 200 μL of 0.1% trifluoroacetic acid (TFA) in water. Then an additional 400 μL of 0.1% TFA in water was added to each well. The sample supernatants were added to the wells and allowed to pass through. The wells were then washed with 500 µL of 0.1% TFA in water and then washed 500 µL of 0.1% formic acid in water. The digested samples were eluted with 2×25 µL of 80% acetonitrile in water with 0.1% formic acid. The eluate was diluted with 50 µL of 0.1% formic acid in water and vortexed briefly at 400 rpm.

50 µL of each digested sample was analyzed via liquid chromatography-tandem mass spectrometry using a Waters H-Class Acquity UPLC coupled to a Thermo QExactive mass spectrometer run in typical peptide mapping conditions.

As shown in FIGS. 2A-2C, trypsin digestion of TRI-1 reproducibly gave rise to the engineered TTPP peptide, and the peptide was easily detected and fragmented. The extracted ion chromatogram for m/z of 905.40-907.60, a subset of the natural isotopic range of engineered TTPP is shown in FIG. 2A. Engineered TTPP eluted at about 19 minutes. Within the total ion chromatograph (shown in FIG. 2B), engineered TTPP was a prominent peak. Furthermore, engineered TTPP showed good fragmentation for MS/MS analysis (FIG. 2C).

Example 2: Detection of the TTPP Peptide in Serum

Next, a series of experiments was performed to determine whether the engineered TTPP peptide could be detected in human, monkey, and mouse sera via LC-MS/MS without significant background interference. Mouse and cynomolgus monkey sera were tested, as these animals are commonly used in pre-clinical therapeutic antibody studies.

Briefly, 100 µL of vortexed Protein G magnetic beads (Pierce) and 100 µL of PBST were added into wells in a 96-well microplate (Qiagen). The plate was gently shaken to ensure a homogenous mixture. The 96-well plate was placed on an Alpaqua 96S Super Magnet 96 well magnet for one minute, followed by a Qiagen Type A 96 well magnet for one minute, and then the solution was removed. This wash cycle was repeated three more times with 200 µL of PBST. After washing was complete, 140 µL of PBST were added into each well containing the beads. Then, 30 µL of (1) mouse serum, (2) monkey serum, (3) human serum or (4) 2 µg/mL TRI-1 was added to the wells. 30 µL of the calibrators, QC, and samples were added into separate wells containing the beads, PBST, and sera. The 96-well plate was then covered and shaken for 1 hour at 600 RPM and washed four times. The calibrators, QC, and samples were eluted by adding 90 µL of 0.1% TFA into each well and gently vortexing the plate to ensure a homogeneous mixture. The plate was placed on an Alpaqua 96S Super Magnet 96 well magnet for one minute, followed by a Qiagen Type A 96-well magnet for one minute. Then, the eluate was transferred into a 2.0 mL 96-well deep well Protein LoBind plate (Eppendorf). The elution procedure was then repeated. The pH of the eluate was neutralized with 20 µL of 1 M tris-HCl pH 8, bringing the total volume to 200 µL. Briefly, 200 µL of SMART digest buffer was added to each of the eluates. The samples were incubated at 70° C. with shaking at 400 rpm for 75 minutes and then were centrifuged at 1000×g for 2 min to pellet the SMART digest resin.

Wells in a SOLAµ HRP SPE plate were equilibrated with 200 µL of acetonitrile and then conditioned with 200 µL of 0.1% TFA in water. An additional 400 µL of 0.1% TFA in water was added to each well. Each sample supernatant was added to a separate well and allowed to pass through. The wells were washed with 500 µL of 0.1% TFA in water and then 500 µL of 0.1% formic acid in water. The digested samples were eluted with 2×25 µL of 80% acetonitrile in water with 0.1% formic acid. The eluate was diluted with 50 µL of 0.1% formic acid in water and vortexed briefly at 400 rpm.

SMART digests of sample were analyzed using a Waters H-Class Acquity UPLC and Thermo QExactive mass spectrometer under standard peptide mapping conditions.

Figure 3D:
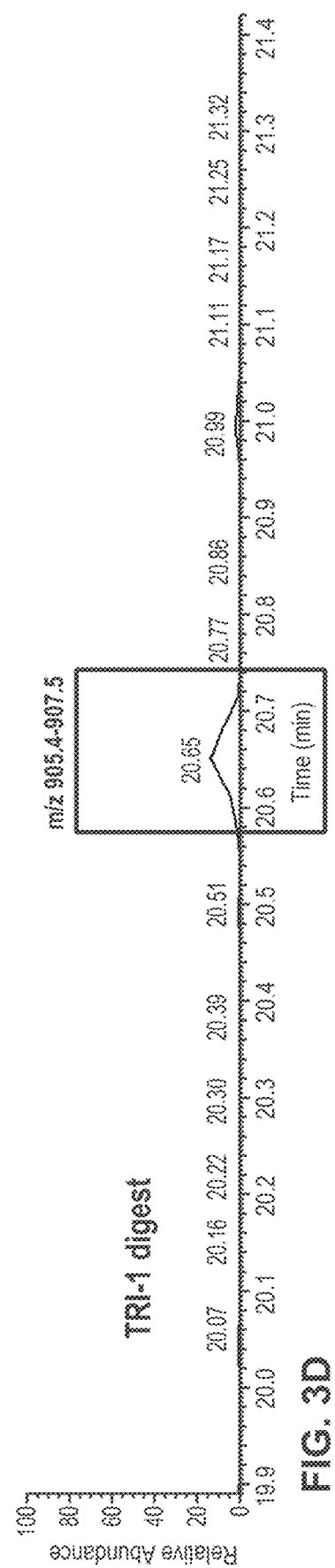
Figure 5A:
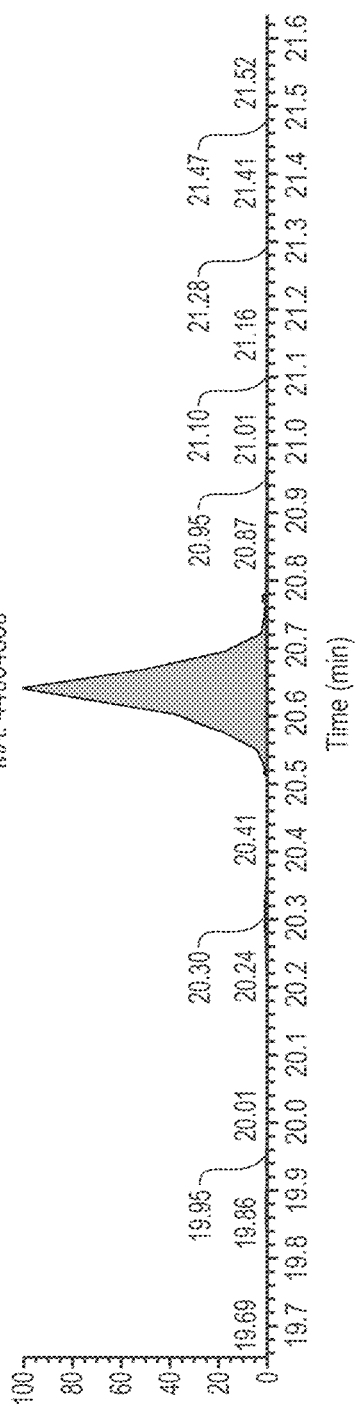
FIGS. 5A-5C show extracted ion chromatograms of engineered TTPP from tryptically-digested TRI-1 in PBST, m/z=905.36-905.55. TRI-1 concentrations were 20 µg/mL (FIG. 5A), 2 µg/mL (FIG. 5B), and 0.2 µg/mL (FIG. 5C). The peak areas for the TTPP peptide were 44064886 (FIG. 5A), 2633166 (FIG. 5B), and 368649 (FIG. 5C).
Figure 5B:
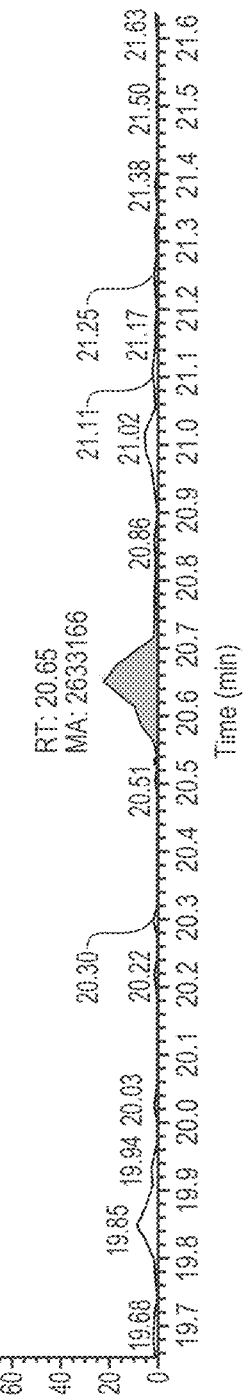
Figure 5C:
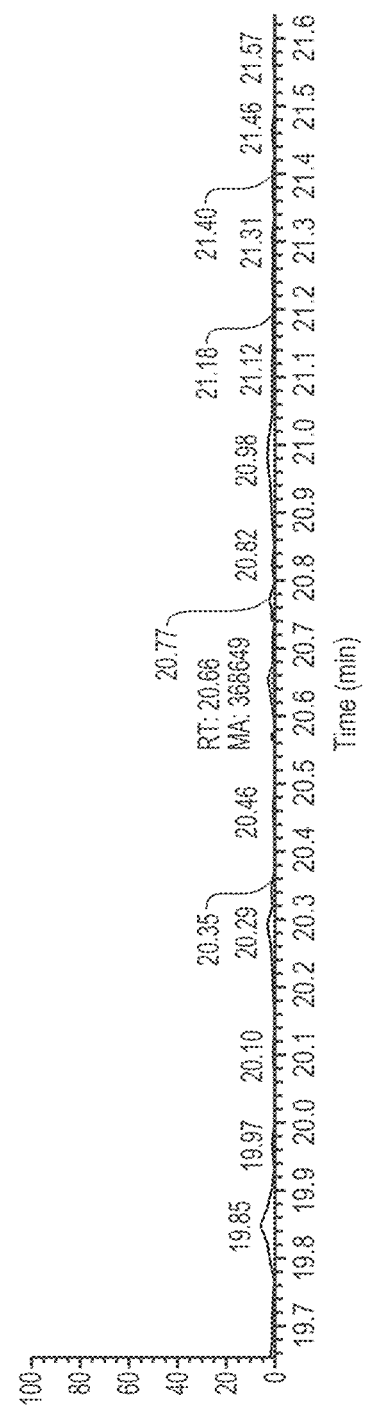
Figure 6A:
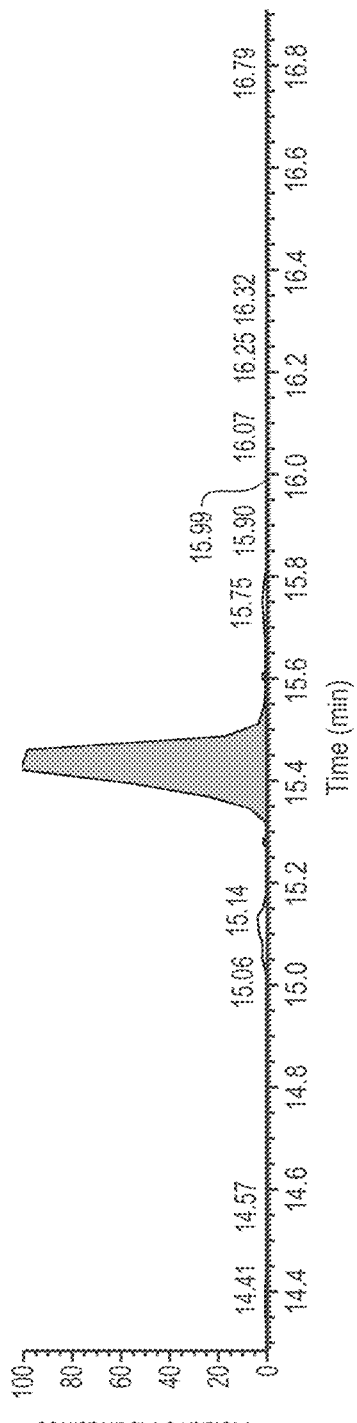
FIGS. 6A-6C show extracted ion chromatograms of unlabeled FNWYVDGVEVHNAK (SEQ ID NO: 10) (FNWY) from tryptically-digested TRI-1 in PBST, m/z=559.90-559.98. TRI-1 concentrations were 20 µg/mL (FIG. 6A), 2 µg/mL (FIG. 6B), and 0.2 µg/mL (FIG. 6C). The peak areas for the FNWY peptide were 70091279 (FIG. 6A), 1078300 (FIG. 6B), and 209110 (FIG. 6C).
Figure 6B:
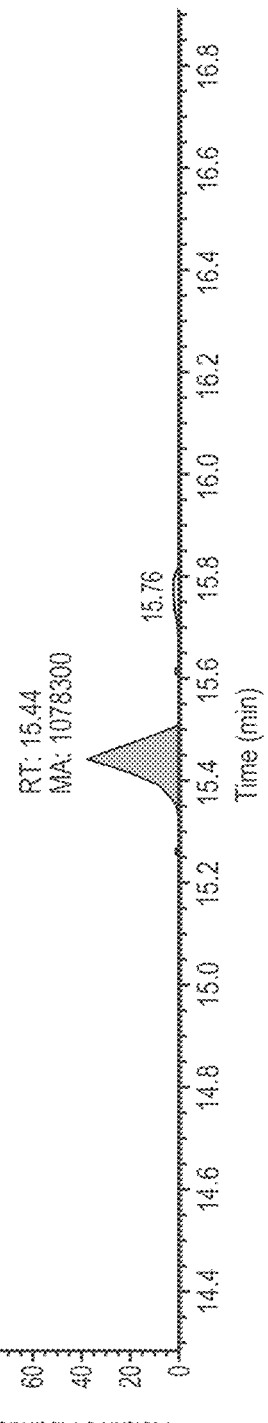
Figure 6C:
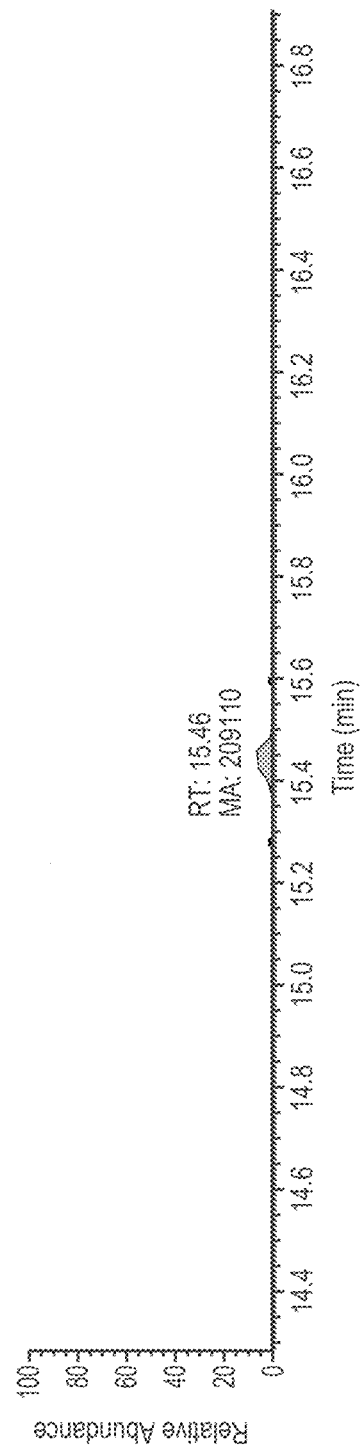
Figure 8A:
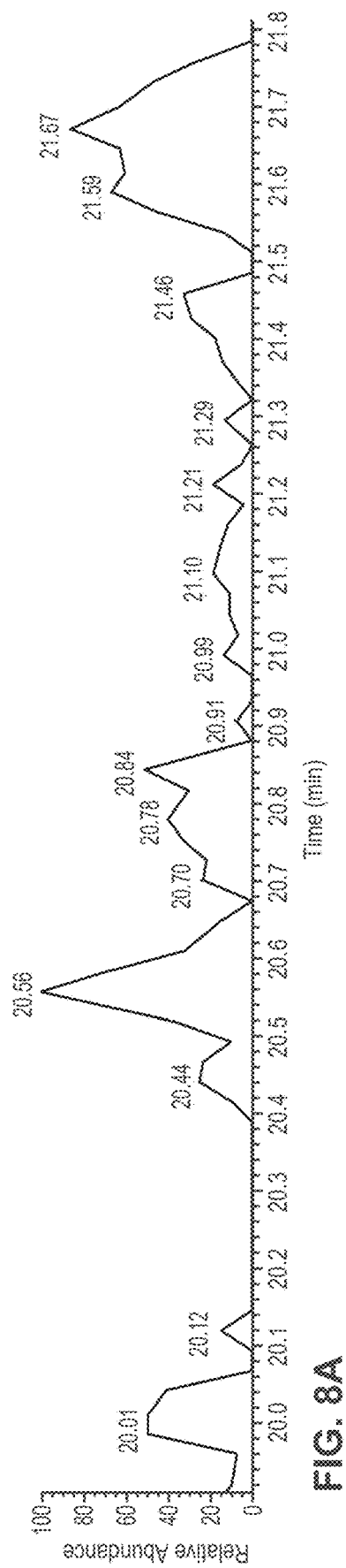
FIGS. 8A-8D show extracted ion chromatograms of engineered TTPP from tryptically-digested TRI-1 in mouse serum, m/z=905.39-905.55. TRI-1 concentrations were 0 µg/mL (control) (FIG. 8A), 0.2 µg/mL (FIG. 8B) 2 µg/mL (FIG. 8C), and 20 µg/mL (FIG. 8D). The peak areas for the TTPP peptide were ND (not detected) (FIG. 8A), ND (not detected) (FIG. 8B), 2168471 (FIG. 8C), and 11833127 (FIG. 8D).
Figure 8B:
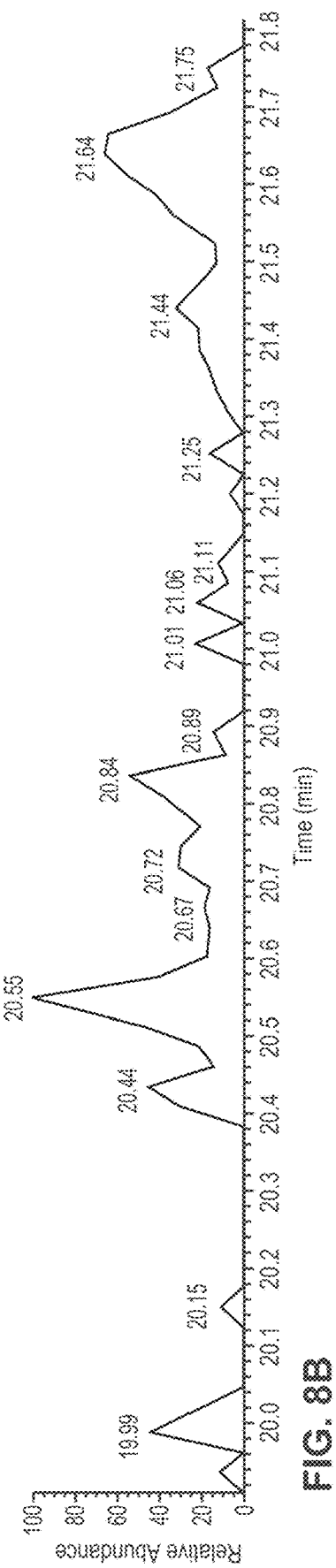
Figure 8C:
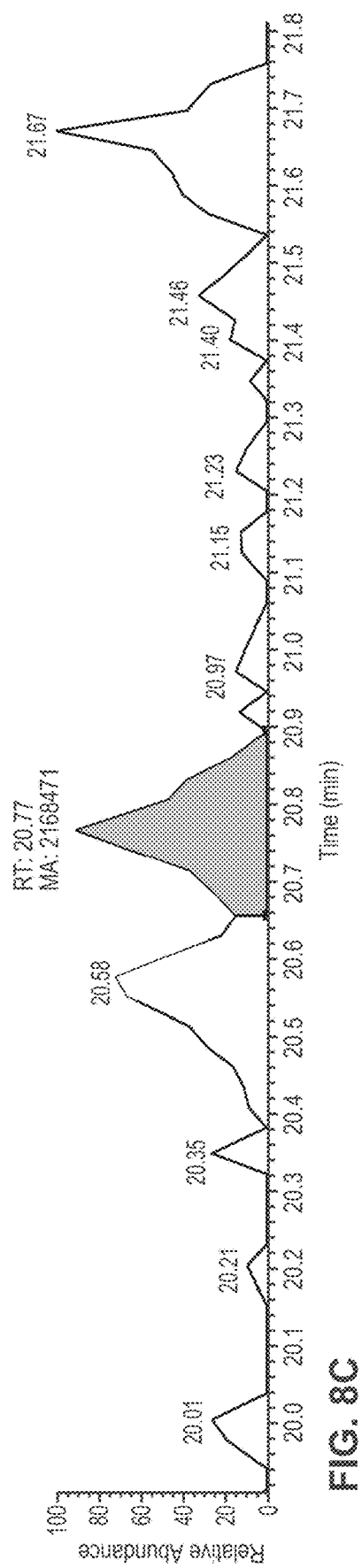
Figure 8D:
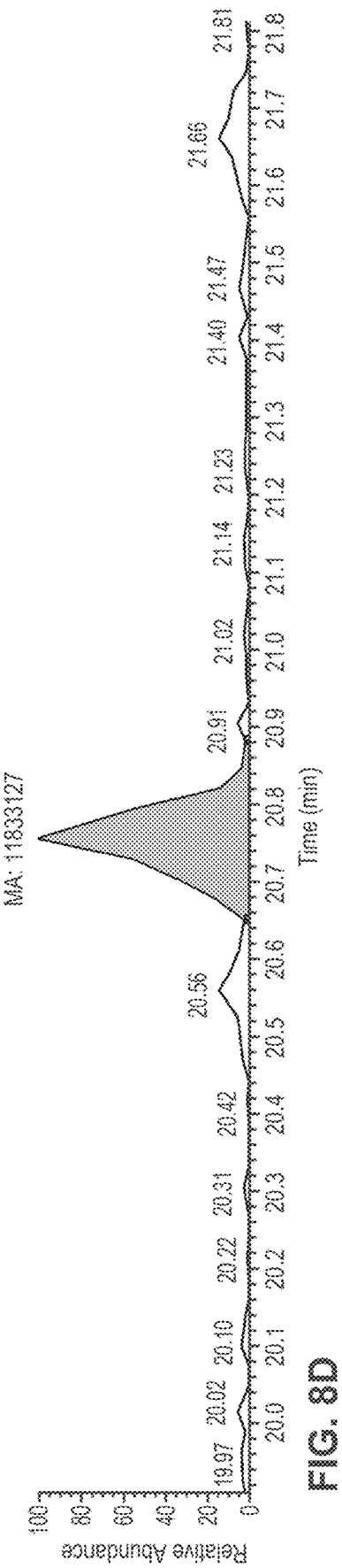
Figure 9C:
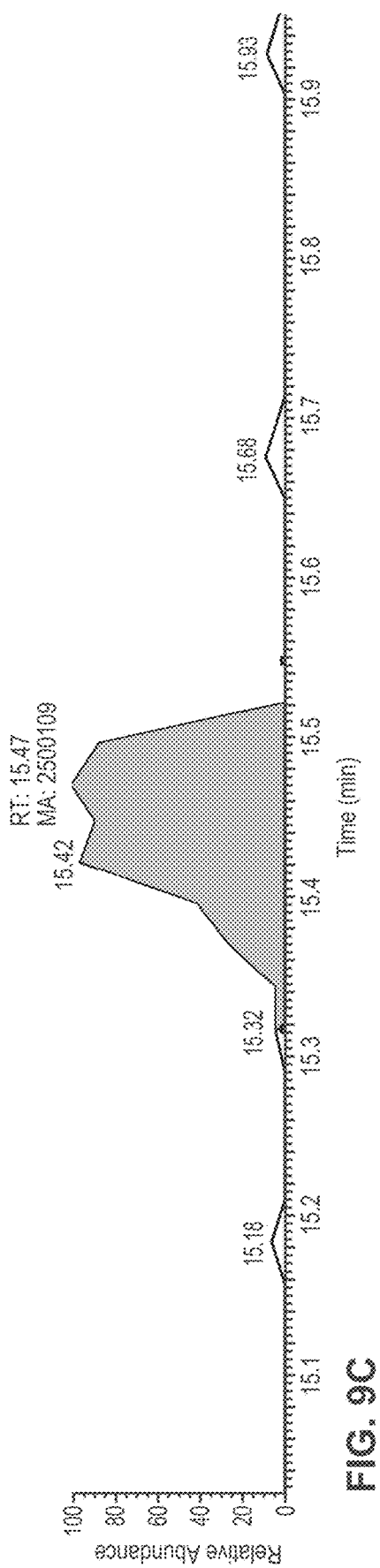
Figure 9D:
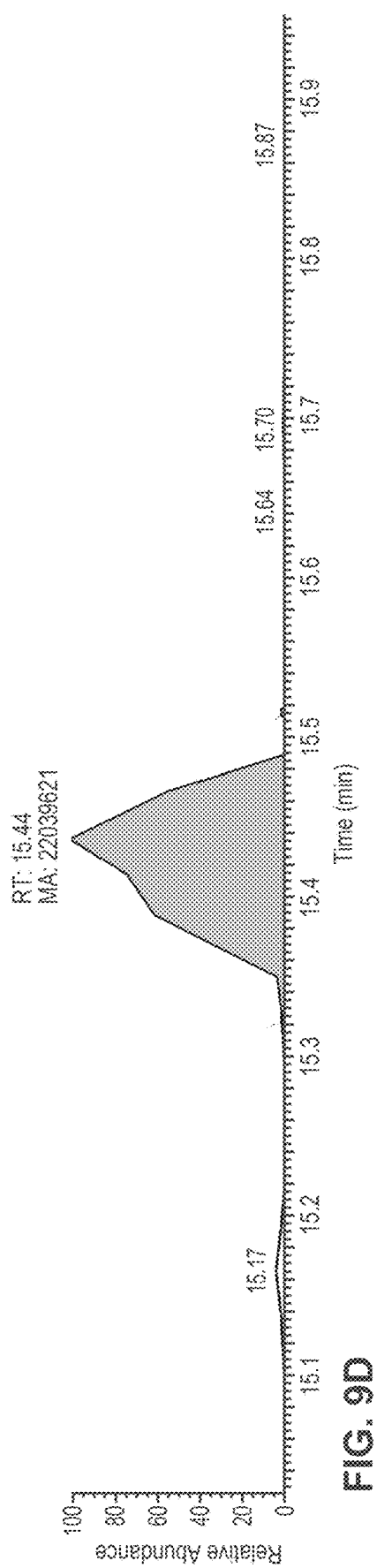
Figure 11A:
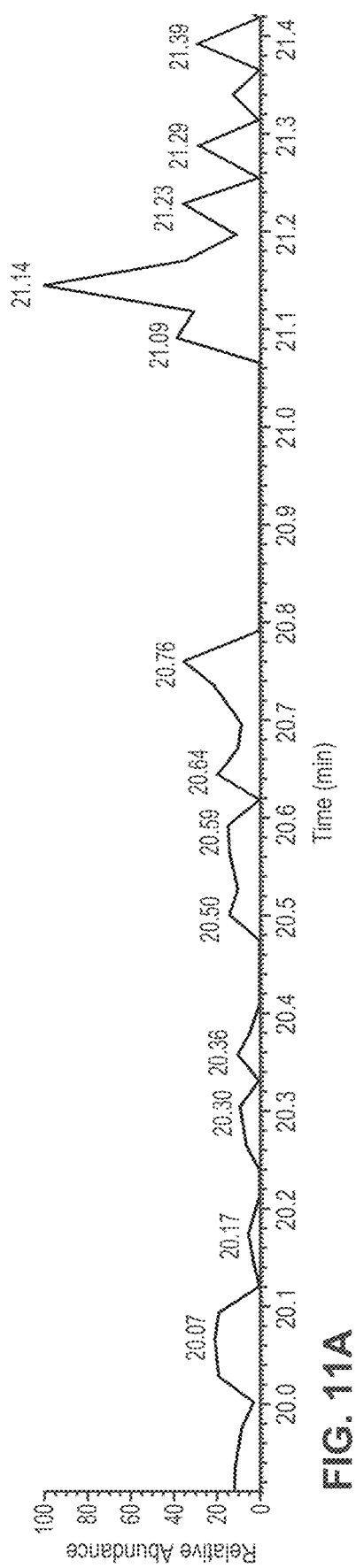
FIGS. 11A-11D show extracted ion chromatograms of engineered TTPP from tryptically-digested TRI-1 in monkey serum, m/z=905.39-905.55. TRI-1 concentrations were 0 µg/mL (control) (FIG. 11A), 0.2 µg/mL (FIG. 11B), 2 µg/mL (FIG. 11C), and 20 µg/mL (FIG. 11D). The peak areas for the TTPP peptide were ND (not detected) (FIG. 11A), ND (not detected) (FIG. 11B), 1013964 (FIG. 11C), and 3751017 (FIG. 11D).
Figure 11B:
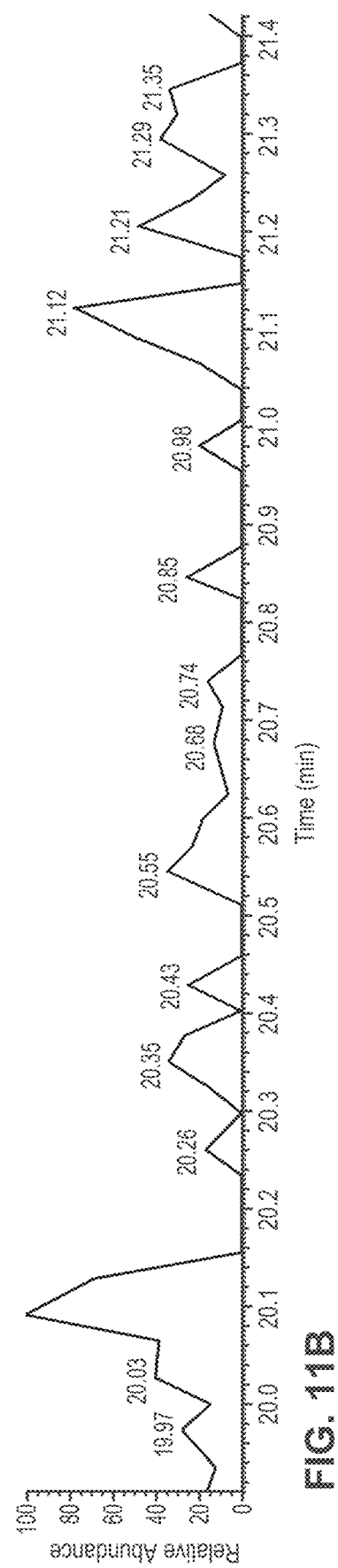
Figure 11C:
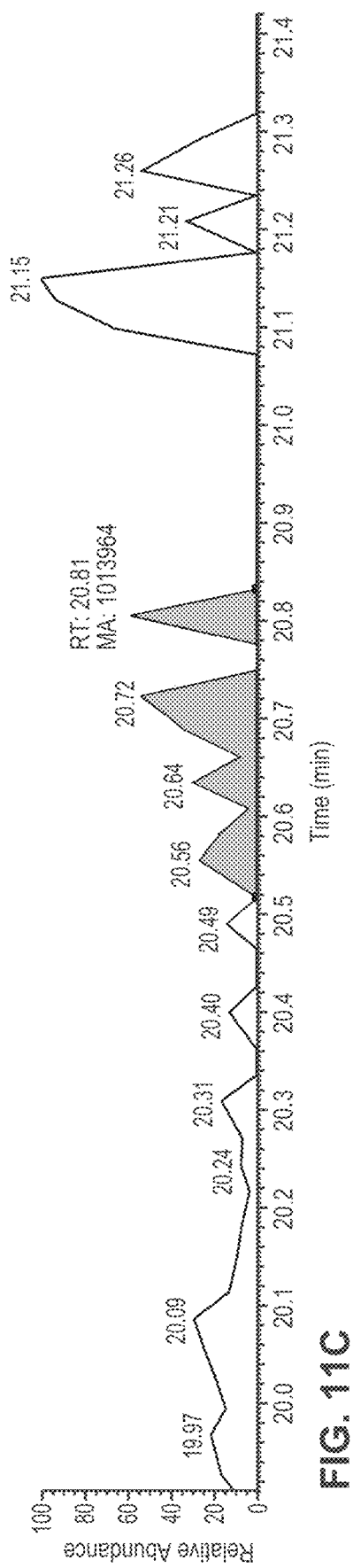
Figure 11D:
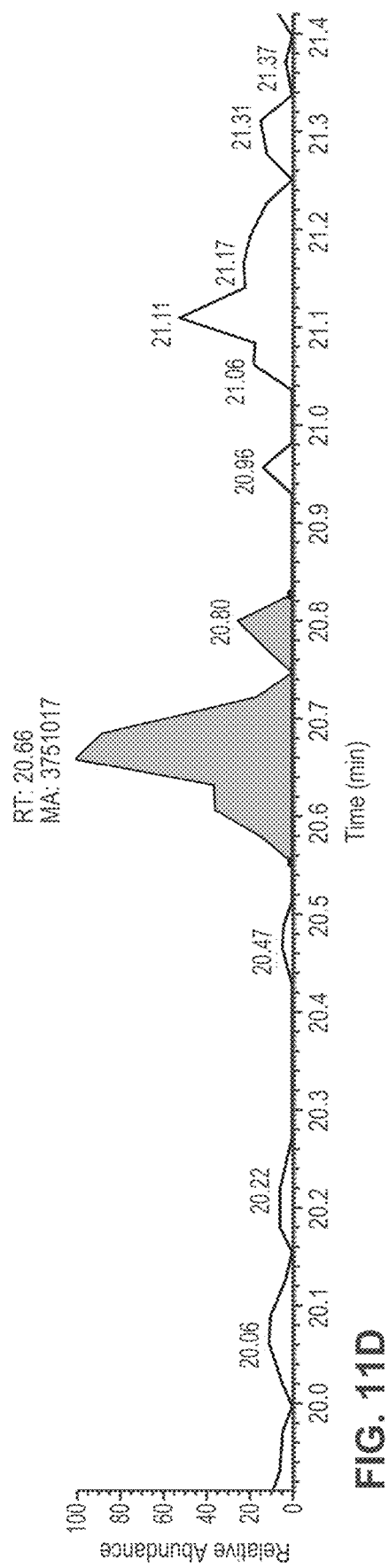
Figure 12A:
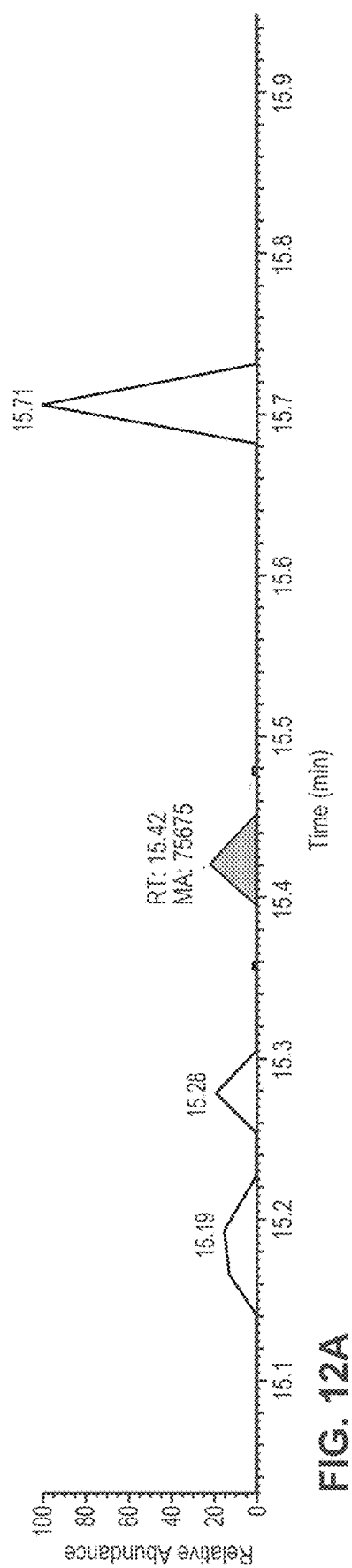
FIGS. 12A-12D show extracted ion chromatograms of unlabeled FNWY from tryptically-digested TRI-1 in monkey serum, m/z=559.92-559.95. TRI-1 concentrations were 0 µg/mL (control) (FIG. 12A), 0.2 µg/mL (FIG. 12B), 2 µg/mL (FIG. 12C), and 20 µg/mL (FIG. 12D). The peak areas for the FNWY peptide were 75675 (FIG. 12A), 97731 (FIG. 12B), 1298150 (FIG. 12C), and 13378187 (FIG. 12D).
Figure 12B:
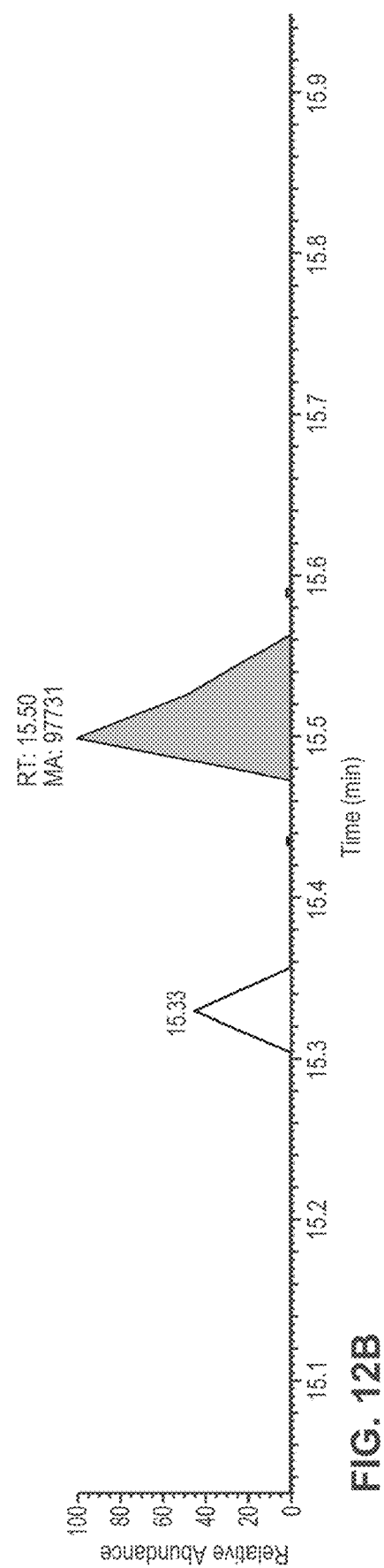
Figure 12C:
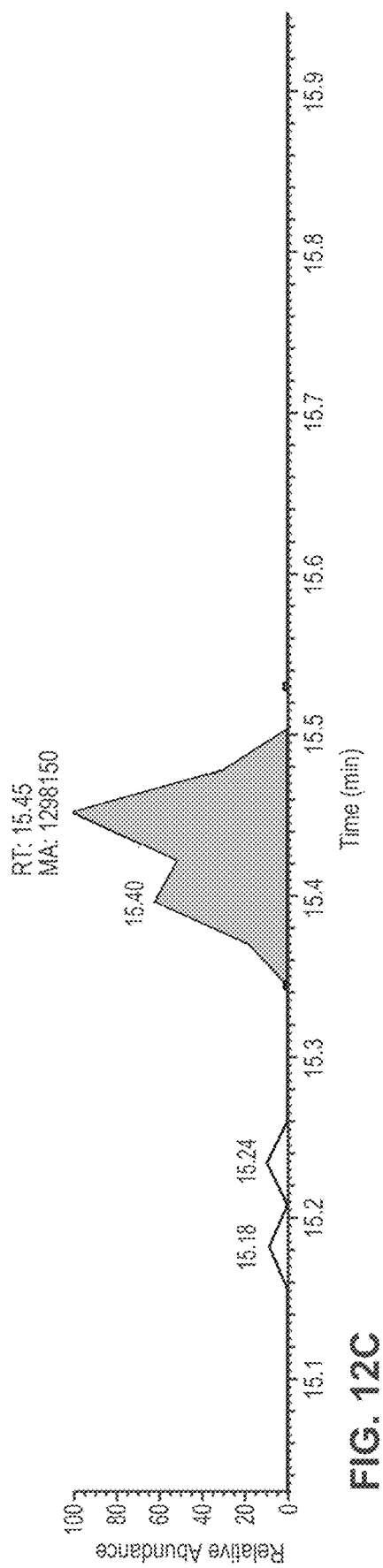
Figure 12D:
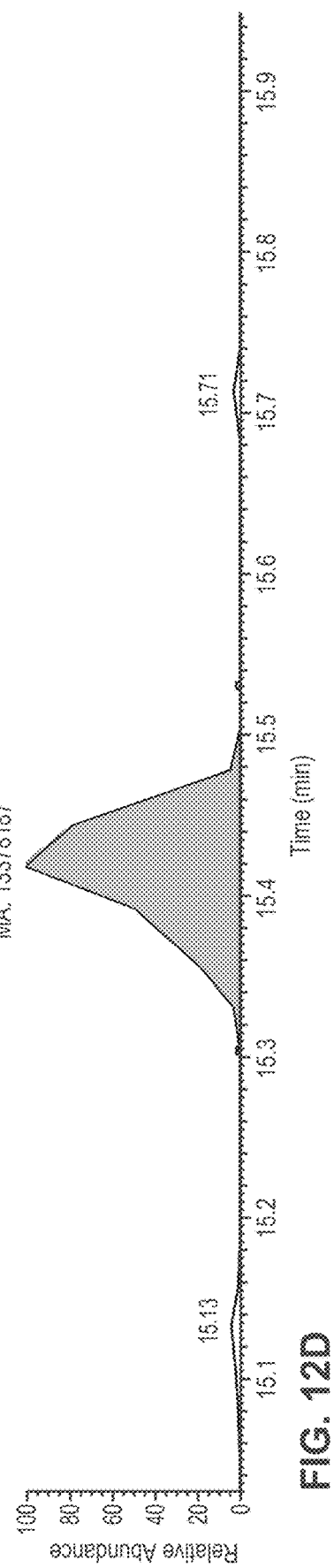

Extracted ion chromatograms for the engineered TTPP peptide (m/z 905.47$^{2+}$) in blank serum are shown in FIGS. 3A-3C, and the extracted ion chromatogram for the engineered TTPP peptide in the TRI-1 digest (2 µg/mL in PBST) is shown in FIG. 3D. The peak at 20.65 min in the TRI-1 digest is not present in any of the serum backgrounds tested.

To confirm that engineered TTPP peptide could be detected in serum backgrounds, mouse, monkey, and human serum samples were spiked with 20 µg/mL TRI-1 and subject to antibody pulldown, digestion, and mass spectrometry analysis as described above.

Extracted ion chromatograms for the engineered TTPP peptide (m/z 905.47$^{2+}$) are shown in FIGS. 4A-4C and TRI-1 digest in PBST is shown in FIG. 4D. Upon spiking TRI-1 into each of the serum backgrounds, engineered TTPP peptide can clearly be seen in all backgrounds.

Serial dilutions of TRI-1 into the appropriate serum background to final concentrations of 0.2, 2, and 20 µg/mL were prepared to determine whether signal increased proportionally to the amounts of analyte in the sample. Aliquots of serum with no antibody spike in were used as background controls. Pull down, digestion, SPE cleanup, and LC-MS/MS were performed as described above.

Figure 14A:
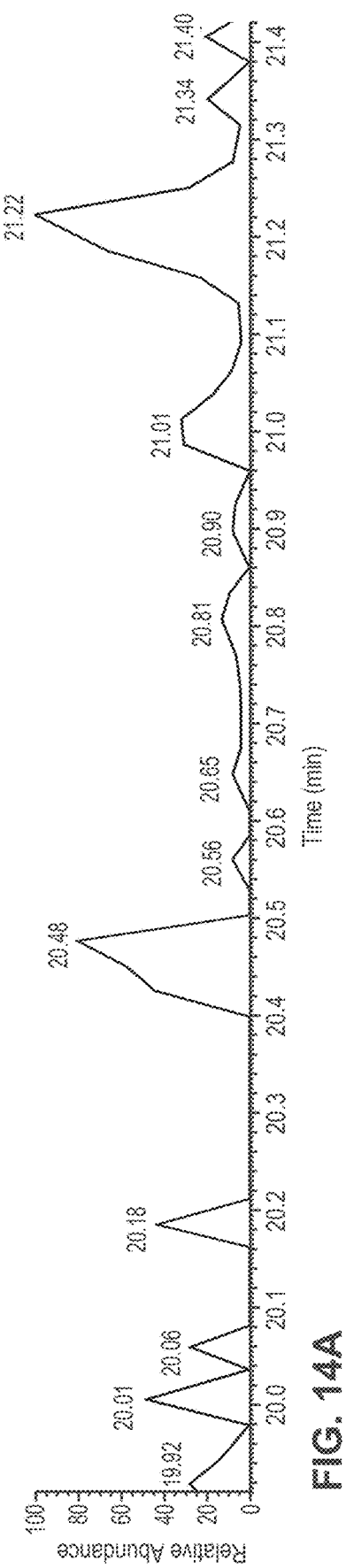
Figure 14B:
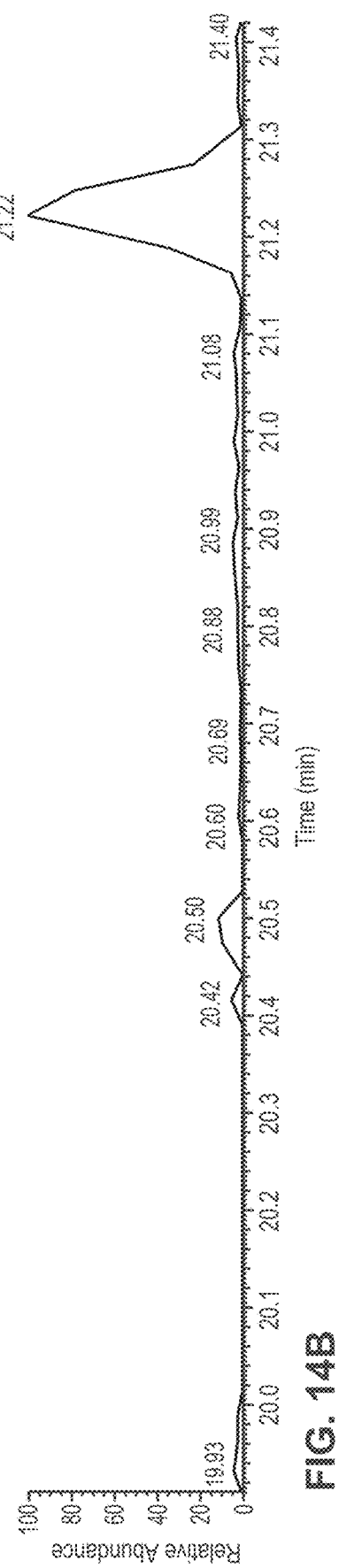
Figure 15A:
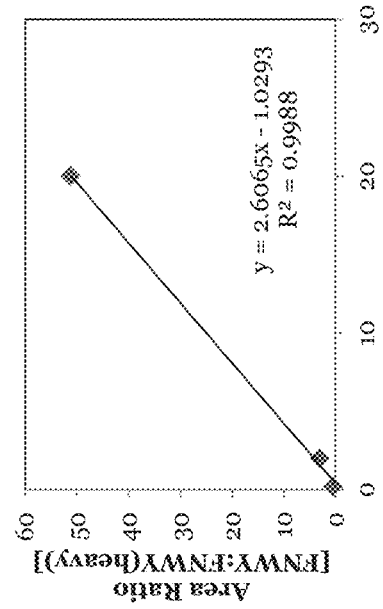
FIGS. 15A-15D show comparisons of area ratio to antibody concentration.
Figure 15B:
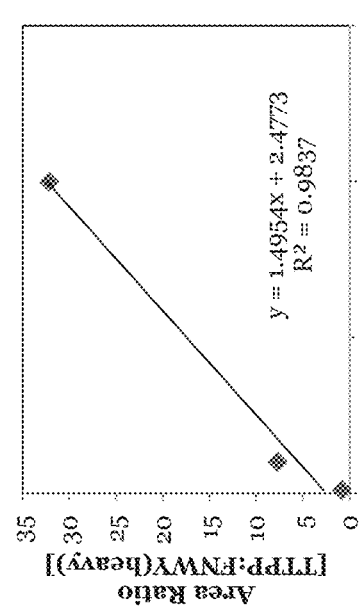
Figure 15C:
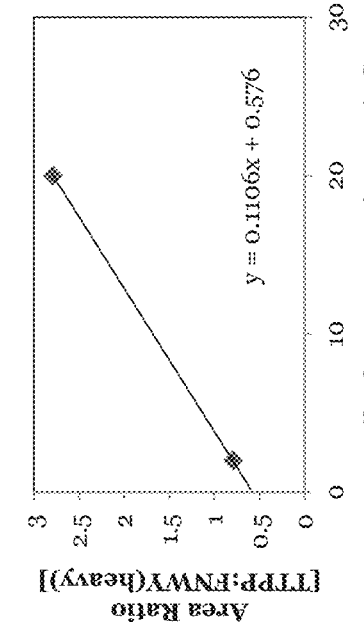
Figure 15D:
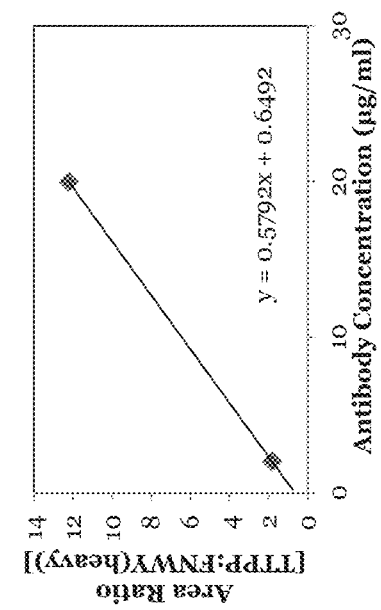

Extracted ion chromatograms of engineered TTPP, unlabeled FNWY, and FNWY (Heavy) derived from analysis of the three tested concentrations of TRI-1 (20, 2, and 0.2 µg/mL) in PBST are shown in FIGS. 5A-5C, 6A-6C, and 7A-7C, respectively. Extracted ion chromatograms of engineered TTPP, unlabeled FNWY, and FNWY (Heavy) derived from analysis of the four tested concentrations of TRI-1 (20, 2, 0.2, and 0 µg/mL) in mouse serum are shown in FIGS. 8A-8C, 9A-9C, and 10A-10C, respectively. Extracted ion chromatograms of engineered TTPP, unlabeled FNWY, and FNWY (Heavy) derived from analysis of the four tested concentrations of TRI-1 (20, 2, 0.2, and 0 µg/mL) in monkey serum are shown in FIGS. 11A-11C, 12A-12C, and 13A-13C, respectively. Extracted ion chromatograms of engineered TTPP derived from analysis of the four tested concentrations of TRI-1 (20, 2, 0.2, and 0 µg/mL) in human serum are shown in FIGS. 14A-14C.

The peak areas for the engineered TTPP peptide and the heavy isotope peptide FNWYVDGVEVHNAK (SEQ ID NO: 10) were determined. See Table 2 below. FNWY (Heavy) is an internal standard derived from the digestion of a stable isotope-labeled universal monoclonal antibody (SILU™ MAB).

TABLE 2

Summary of Results of Quantification Assay

| Background | TRI-1 Concentration (μg/mL) | Engineered TTPP Peak Area | FNWY (heavy) Peak Area | FNWY (light-unlabeled) Peak Area | Area Ratio (Engineered TTPP:FNWY (heavy)) | Area Ratio (FNWY:FNWY (heavy)) |
|---|---|---|---|---|---|---|
| PBST | 20 | 44064886 | 1369078 | 70091279 | 32.2 | 51.2 |
|  | 2 | 2633166 | 343482 | 1078300 | 7.7 | 3.1 |
|  | 0.2 | 368649 | 473743 | 209110 | 0.8 | 0.4 |
| Mouse Serum | 20 | 11833127 | 967309 | 22039621 | 12.2 | 22.8 |
|  | 2 | 2168471 | 1199642 | 2500109 | 1.8 | 2.1 |
|  | 0.2 | ND | 2310675 | 410330 | ND | 0.2 |
| Monkey Serum | 20 | 3751017 | 1344983 | 13378187 | 2.8 | 9.9 |
|  | 2 | 1013964 | 1271728 | 1298150 | 0.8 | 1.0 |
|  | 0.2 | ND | 1216254 | 97731 | ND | 0.1 |
| Human Serum | 20 | 1848332 |  | NA |  | NA |
|  | 2 | 194065 |  | NA |  | NA |
|  | 0.2 | ND |  | NA |  | NA |

The area ratios of engineered TTPP to FNWY(Heavy) for PBST, mouse serum, and monkey serum backgrounds are also shown in Table 2 and plotted versus input TRI-1 concentration in FIGS. 15A-D. The area ratio of engineered FNWY to FNWY(Heavy) for PBST is shown in Table 2 and plotted versus input antibody concentration in FIGS. 15A, 15C, and 15D.

The data above demonstrate that there is little to no background interference for the TTPP peptide in mouse serum, monkey serum, or human serum, and that signal generated by the TTPP peptide correlates with the amount of peptide in a sample.

TABLE 3

Amino Acid Sequences in Examples 1 and 2

| SEQ ID NO. | SEQUENCE |
|---|---|
| 1 | THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLKGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 2 | THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLKGKEYKCK VSNKALPAPI EKTISKAKGQ PREPQVYTLP PCRDELTKNQ VSLWCLVKGF YPSDIAVFWE SNGQPENNYK TTPPVLDSDG SFFLYSKLTV DKSRWQQGNV FSCSVLHEAL HSHYTQKSLS LSPG |
| 3 | THTCPPCPAP ELLGGPSVFL FPPKPKDTLM ISPTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVCTLP PSRDELTKNQ VSLSCAVKGF YPSDIAVEWE SNGQPENNYK TTPPVLDSDG SFFLVSKLTV DKSRWQQGNV FSCSVLHEAL HSHYTQKSLS LSPG |
| 4 | THTCPPCPAP ELLGGPSVL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVCTLP PSRDELTKNQ VSLSCAVKGF YPSDIAVEWE SNGQPENNYK TTPPVLDSDG SFFLYSKLTV DKSRWQQGNV FSCSVMHEAL HNHYTQKSLS LSPGK |
| 5 | THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PCRDELTKNQ VSLWELVKGF YPSDIAVEWE SNGQPENNYK TTPPVLDSDG SFFLYSKLTV DKSRWQQGNV FSCSVMHEAL HNHYTQKSLS LSPG |
| 6 | DGSFFLVS |
| 7 | TTPPVLDSDG SFFLVSK |
| 8 | DGSFFLVSKL TV |

TABLE 3-continued

Amino Acid Sequences in Examples 1 and 2

| SEQ ID NO. | SEQUENCE |
|---|---|
| 9 | GSFFLVSKLT VD |
| 10 | FNWYVDGVEV HNAK |
| 11 | ALHSHYTQK |

Example 3: Use of the TTPP Surrogate Peptide in a Generic Mass Spectrometry-Based Assay for Detecting and Quantifying an Exemplary Trispecific Antibody Overview Therapeutic antibodies are attractive tools for targeting diseases and their market is growing at fast pace. Ligand-binding assays have been standard methods for measuring therapeutic antibodies. However, in order to provide support for their development, new bioanalytical strategies are necessary. LC-MS/MS represents a complementary method, providing specificity and higher reproducibility requested for Good Laboratory Practice (GLP) studies. Moreover, LC-MS/MS overcomes some limitations associated with ligand-binding assays (LBAs), such as matrix interference (e.g., components in sample that may impede accurate quantification of the therapeutic antibody) and the development of reagents, which can be costly and time-consuming.

IgGs represent the majority of therapeutic proteins currently in the clinics. In order to reduce immunogenicity, therapeutic antibodies are engineered to comprise human antibody constant region, such as human IgG constant regions. Developing a bioanalytical LC-MS assay to quantitate such therapeutic antibodies has been challenging, as it is difficult to select suitable surrogate peptides that can be used to discriminate between endogenous human IgGs in a sample (e.g., a plasma, serum or blood sample) and the therapeutic IgG antibody without the help of an immune-affinity step. To overcome this issue, the constant region of an exemplary therapeutic antibody was engineered to comprise a substitution mutation, e.g., a substitution mutation that is not naturally found in human antibody constant regions, or the antibody constant regions of non-human primates or pre-clinical animals (e.g., mice). This stratagem allows an accurate quantification of the therapeutic antibody in both non-human and human samples without matrix interference.

Described below is an affinity extraction-free LC-MS/MS assay for a fast and accurate quantitation of a trivalent trispecific antibody against a soluble target in plasma. By avoiding an immuno-affinity step, this method will allow accurate quantification of total drug (sum of target-bound drug plus free drug). Moreover, because the substitution mutation is in the antibody constant region, this method can be used to quantify any therapeutic protein that comprises an antibody constant region.

Analytical Procedure

Figure 17:
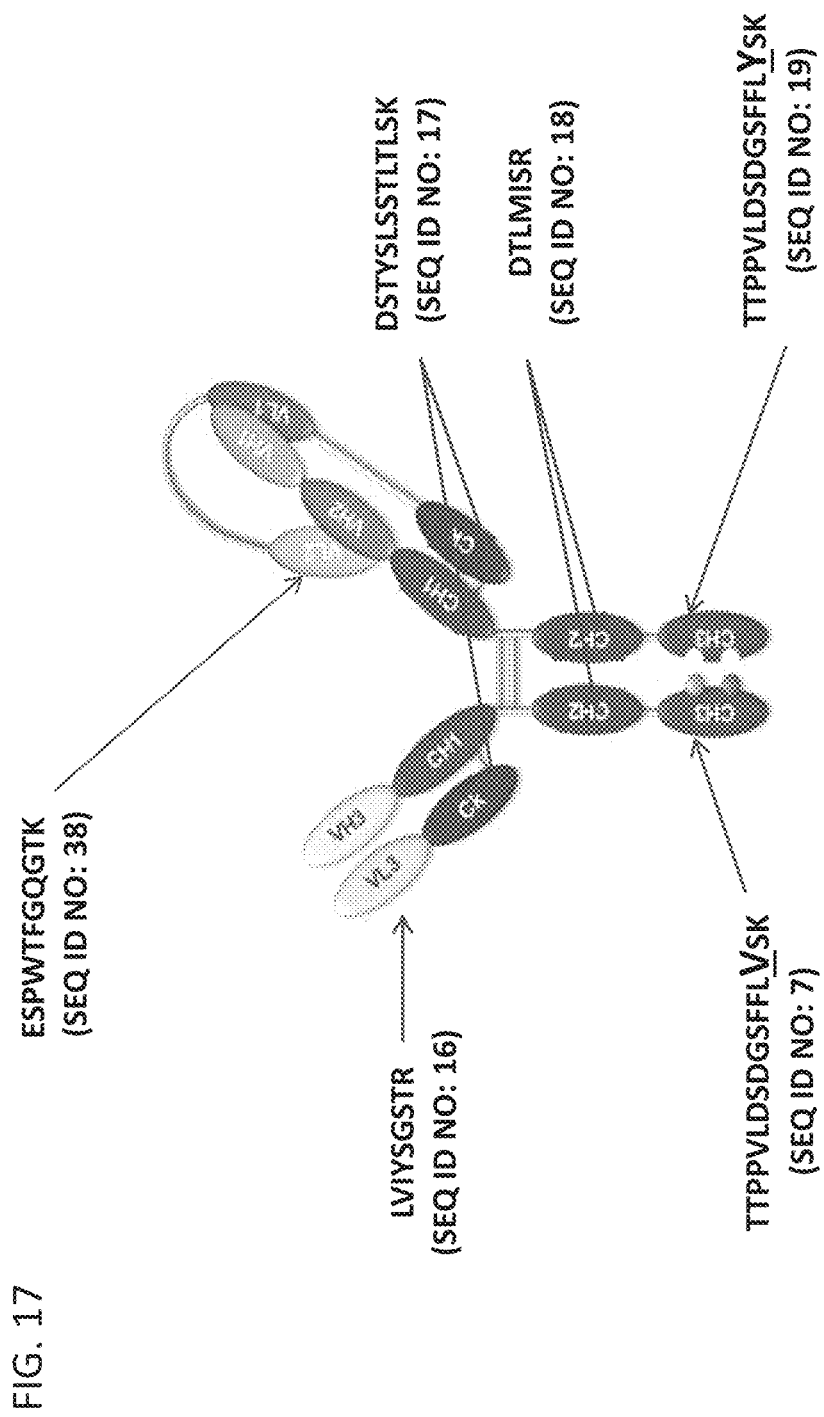
FIG. 17 shows a schematic of the exemplary trispecific antibody and where the sequences of the surrogate peptides underlined in FIG. 16 are located in the trispecific antibody.

The surrogate peptides that were selected for quantification of an exemplary trispecific antibody via LC-MS/MS are shown in FIGS. 16 and 17 and in Table 4 below. These surrogate peptides were selected based on their linear response. Peptides whose sequences are not found in human proteins or in the proteins of non-human primates (i.e., SEQ ID NO: 7, 16, and 38) were used. For absolute quantification, the engineered peptide TTPPVLDSDGSFFLVSK (SEQ ID NO: 7) was used (See FIGS. 16 and 17 and Table 4 below). In order to assure integrity of the analyte, the ratios between the areas under the peaks of TTPPVLDSDGSFFLVSK (SEQ ID NO: 7) and the other peptides listed in Table 4 were monitored in the samples that were quantified via LC-MS/MS. The ratios stayed constant at all time points (results not shown).

TABLE 4

List of Surrogate Peptides and the MS Parameters for their detection

| Peptide | Mass Transitions | Collision Energy (V) |
|---|---|---|
| TTPPVLDSDGSFFLVSK (SEQ ID NO: 7) | Precursor Ion m/z 905.8 → Product Ion m/z 804.5 | 37 |
| DTLMISR (SEQ ID NO 18) | Precursor Ion m/z 418.2 → Product Ion m/z 506.3 | 14 |
| LVIYSGSTR (SEQ ID NO: 16) | Precursor Ion m/z 751.9 → Product Ion m/z 1036.6 | 21 |
| DSTYSLSSTLTLSK (SEQ ID NO: 17) | Precursor Ion m/z 912.2 → Product Ion m/z 811.0 | 30 |
| ESPWTFGQGTK (SEQ ID NO: 38) | Precursor Ion m/z 619.3 → Product Ion m/z 738.4 | 34 |

The stable-isotope-labeled version of TTPPVLDSDGSFFLVSK (SEQ ID NO: 7) was used as internal standard (FIG. 19B).

Figure 18:
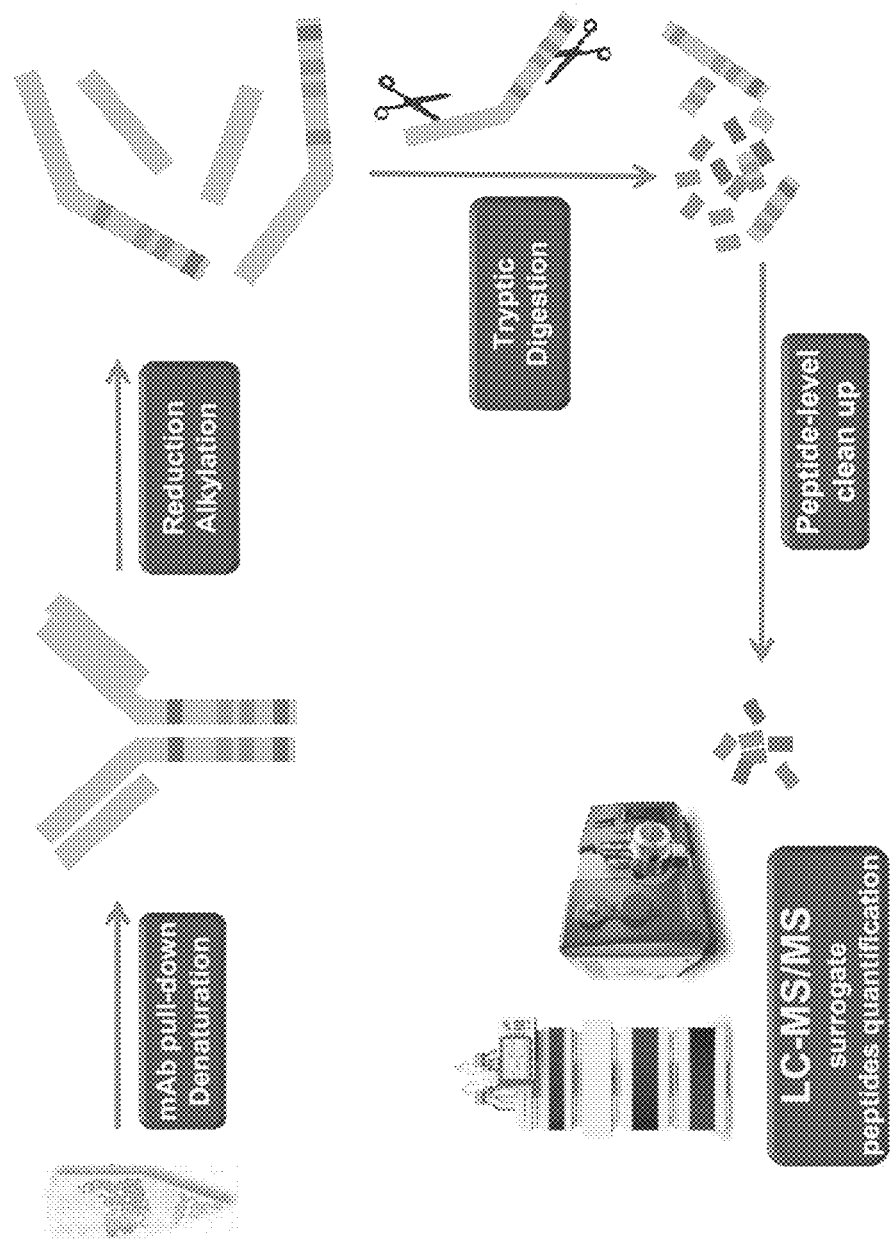
FIG. 18 provides an exemplary workflow diagram of a method of quantifying the trispecific antibody using the TTPP peptide.

A fast and robust workflow was developed for supporting pre-clinical studies (see FIG. 18). The method is based on the pellet digestion protocol described in Ouyang et al. (2012) *Bioanalysis*. 4(1), 17-28. Each step in the digestion protocol was optimized to maximize the recovery of the trispecific antibody from the sample and detection of the surrogate peptides. (The workflow for a sample from a human subject included a Protein A immunopurification step prior to the denaturation step.)

The method used only 10 μL of a plasma sample. As a small sample volume was sufficient, the surrogate peptide quantification method is suitable for measuring preclinical samples from, e.g., rodents. Standard digestion time was also optimized. The best signal intensity was observed when the sample was digested for two hours at 37° C. To further increase the sensitivity of the quantification method, samples were subjected to solid phase extraction (SPE). The best recovery was obtained using OASIS MCX cartridges.

Validation for Rat Plasma

Method validation was performing in rat plasma for supporting a GLP toxicological study. A quadratic regression model was chosen with mean regression coefficient at 0.979 over three independent calibration curve with three replicates for run and 8 nominal concentrations (FIG. 19A). Assay variability was assessed by measuring accuracy and precision of quality control (QC) samples at LLOQ (lowest limit of quantification), LOW, MID, and HIGH of three independent preparations. Intra/inter-run accuracy and precision are summarized in Table 5. Matrix effect was carried out by using six different plasma batches (see Table 6 below). Stability of the antibody in plasma was evaluated in spiked human plasma stored for 1-3 and 6 months at −80° C. and at 37° C. for 24 h. No degradation was observed during these intervals.

TABLE 5

Inter- and Intra-Run Accuracy and Precision of three independent samples at LLOQ, LOW, MID, and HIGH

| Nominal Concentration (μg/ml) | Mean Calculated Concentration (μg/ml) | Accuracy % Difference Estimate | Intra-Run Percent Precision | Inter-Run Percent Precision |
| --- | --- | --- | --- | --- |
| LLOQ 2.5 (n = 18) | 2.60 | 4.00 | 16.2 | 14.8 |
| QC LOW 7.5 (n = 18) | 8.10 | 7.99 | 5.57 | 5.01 |
| QC MID 750 (n = 18) | 827 | 10.2 | 4.17 | 9.31 |
| QC HIGH 7,500 (n = 18) | 8220 | 9.53 | 2.61 | 8.63 |

TABLE 6

Matrix Effect on Six Independent Batches of Rat Plasma

| Rat 1 (Male) | Rat 2 (Male) | Rat 3 (Male) | Rat 4 (Female) | Rat 5 (Female) | Rat 6 (Female) |
| --- | --- | --- | --- | --- | --- |
| Peak Areas of TTPP Peptide (SEQ ID NO: 7) in Blank Plasma Samples | | | | | |
| 22 | 34 | 48 | 84 | 67 | 50 |
| 31 | 14 | 25 | 61 | 661 | 11 |
| 11 | 28 | 17 | 148 | 14 | 56 |
| Area LLOQ (2.5 μg/mL) | | | | | |
| 121217 | 155613 | 130475 | 175238 | 160757 | 157595 |
| 132624 | 142140 | 148339 | 163371 | 171581 | 156564 |
| 125229 | 128498 | 142467 | 173085 | 165758 | 117524 |
| 0.637% | 4.58% | 5.54% | 19.9% | 1.74% | 2.28% |
| 1.30% | 14.2% | 1.68% | 11.2% | 10.4% | 1.95% |
| 1.42% | 3.44% | 0.822% | 4.67% | 2.90% | 9.21% |

Figure 22A:
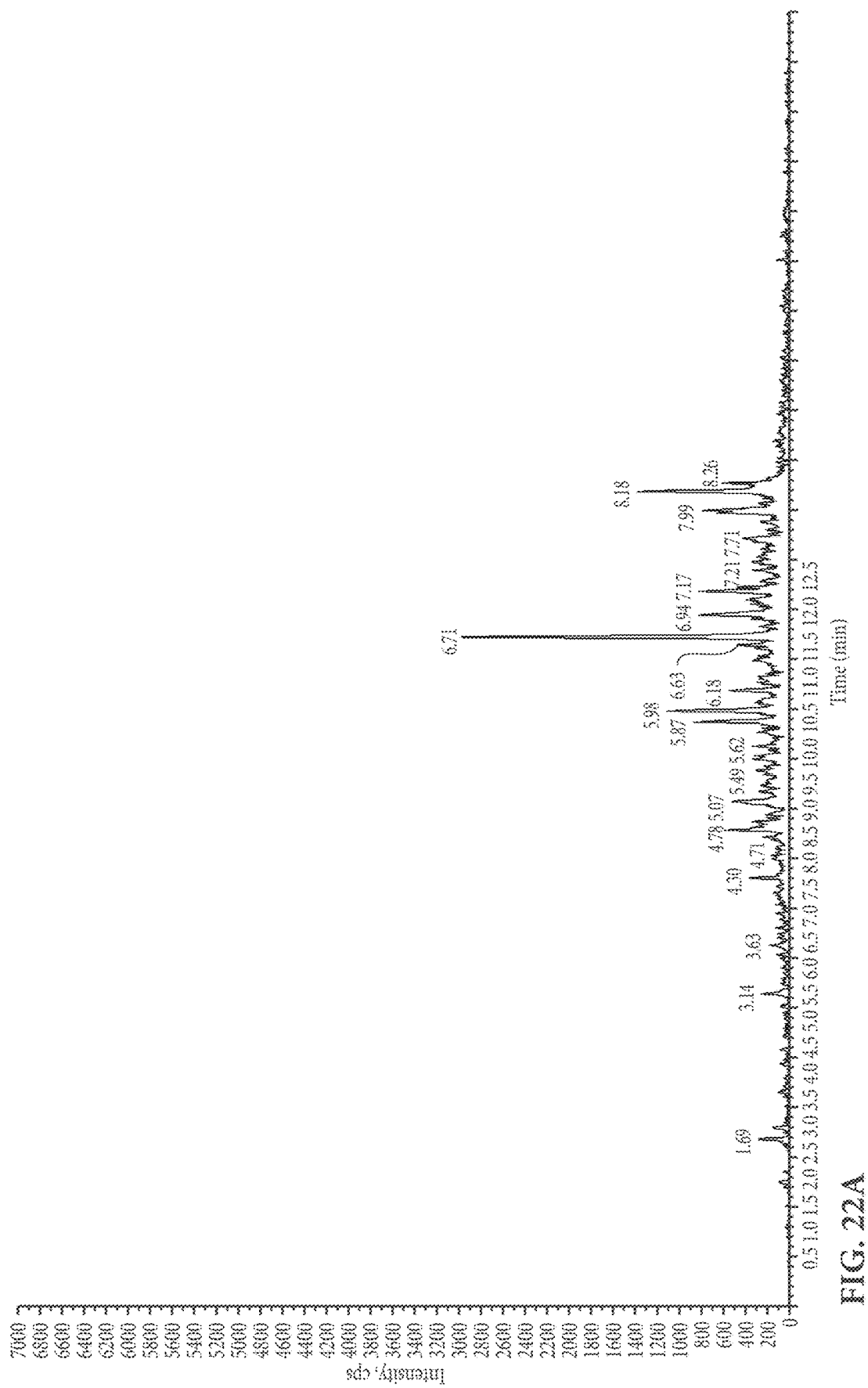
FIG. 22A shows the results of LC-MS/MS analysis of a blank rat serum sample.
Figure 22B:
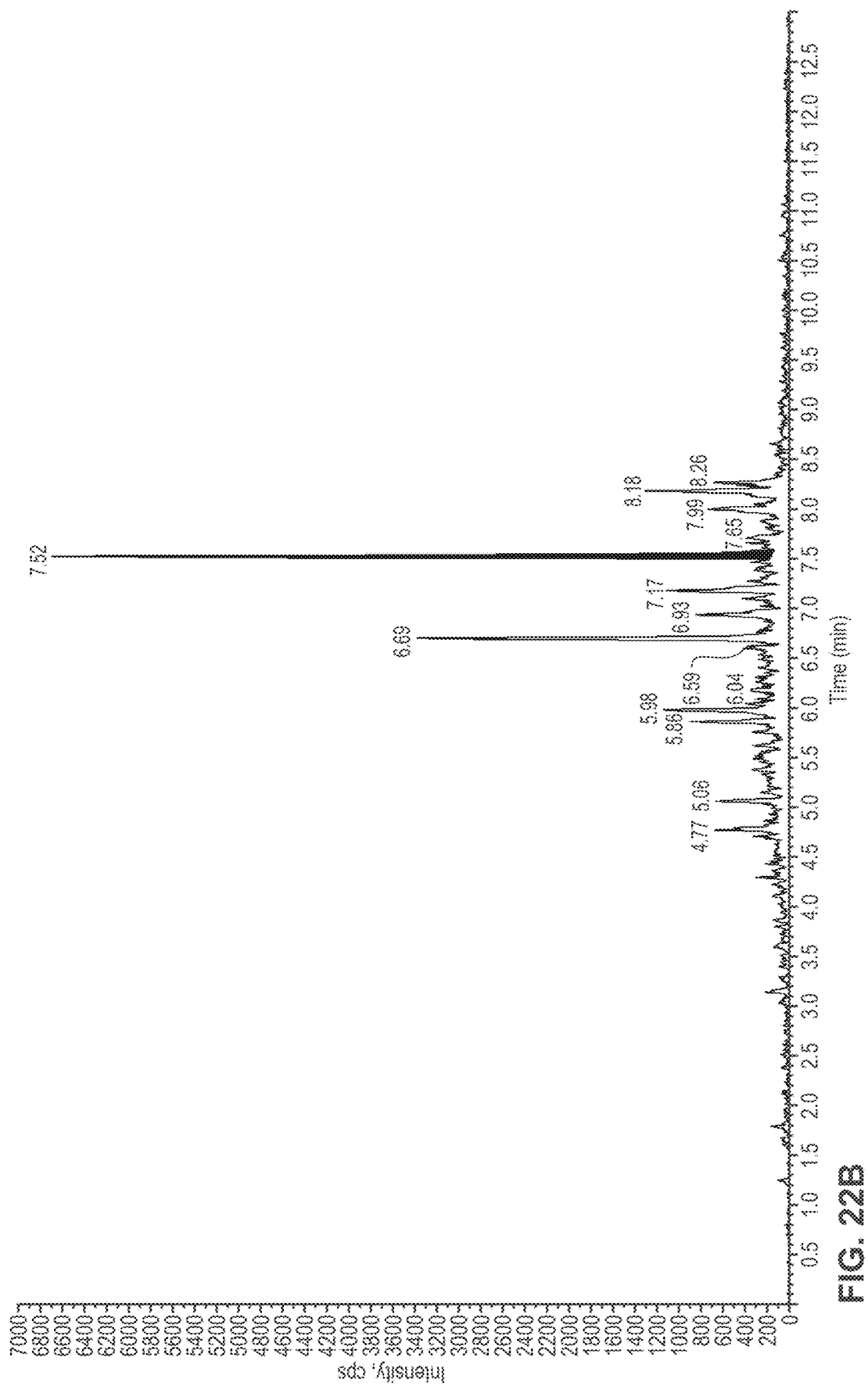
FIG. 22B shows the MS/MS spectrum of a rat serum sample spiked with 5 µg/ml trispecific antibody.
Figure 22C:
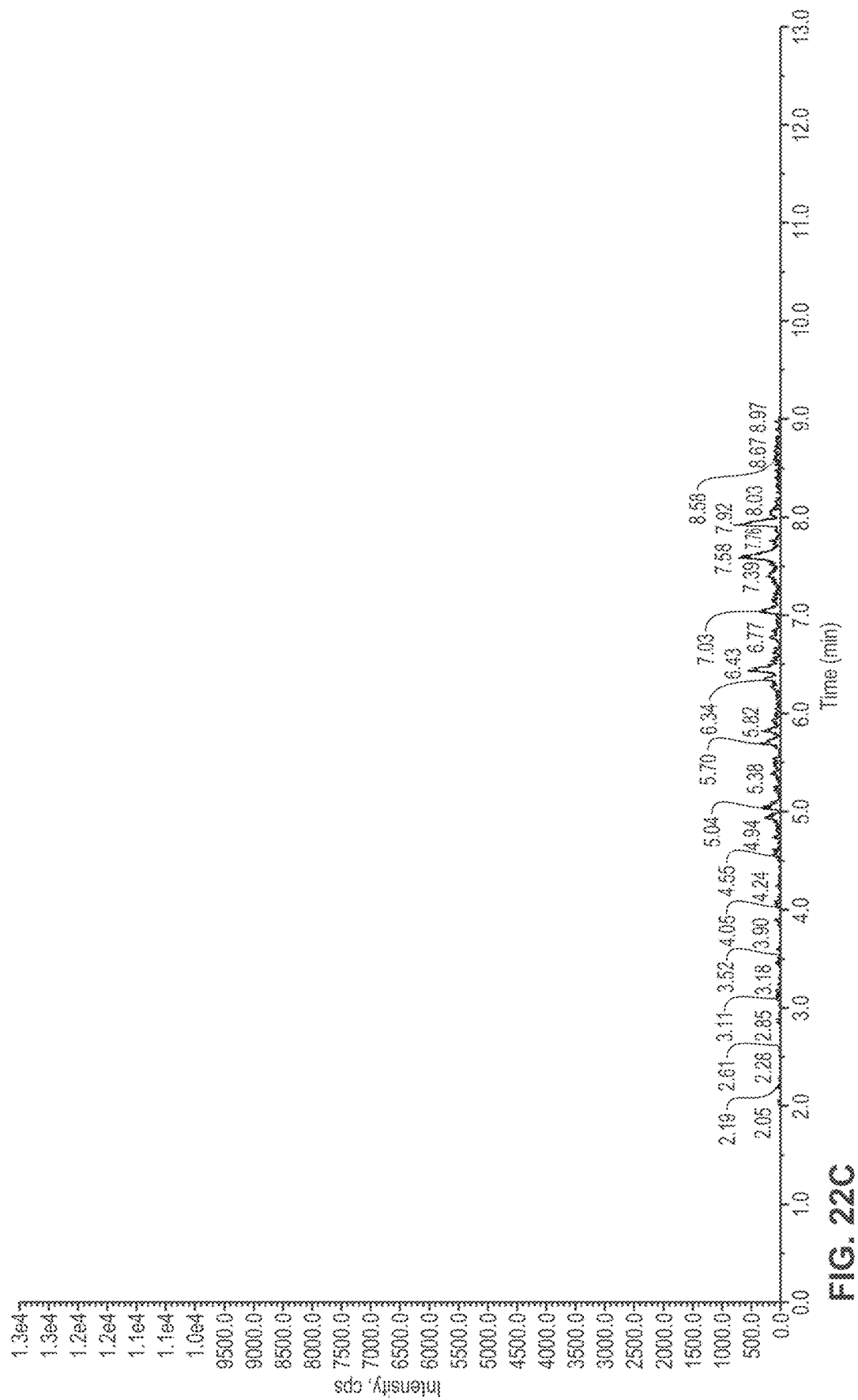
FIG. 22C shows the results of LC-MS/MS analysis of a blank monkey serum sample.
Figure 22D:
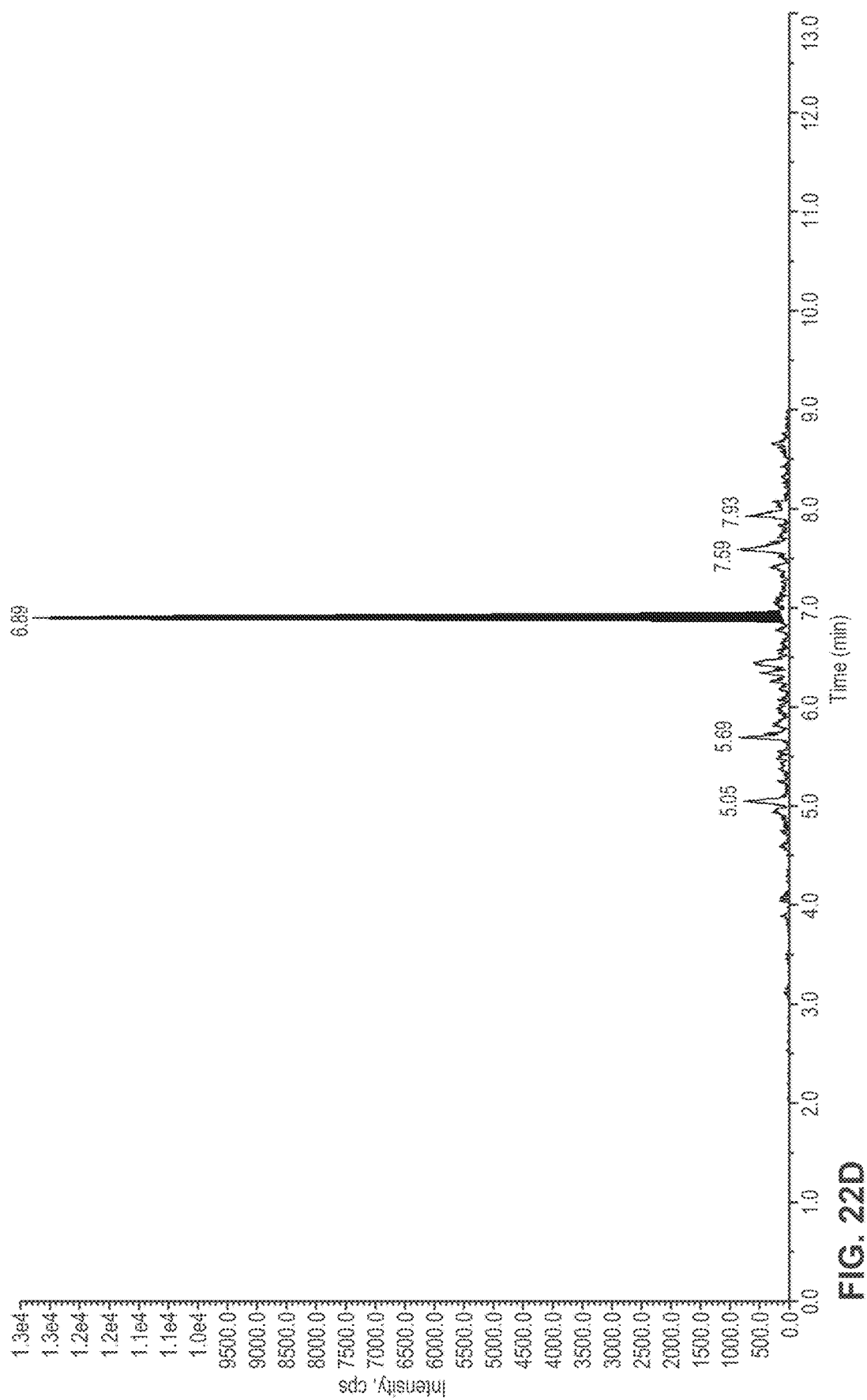
FIG. 22D shows the MS/MS spectrum of a monkey serum sample spiked with 5 µg/ml trispecific antibody.
Figure 22E:
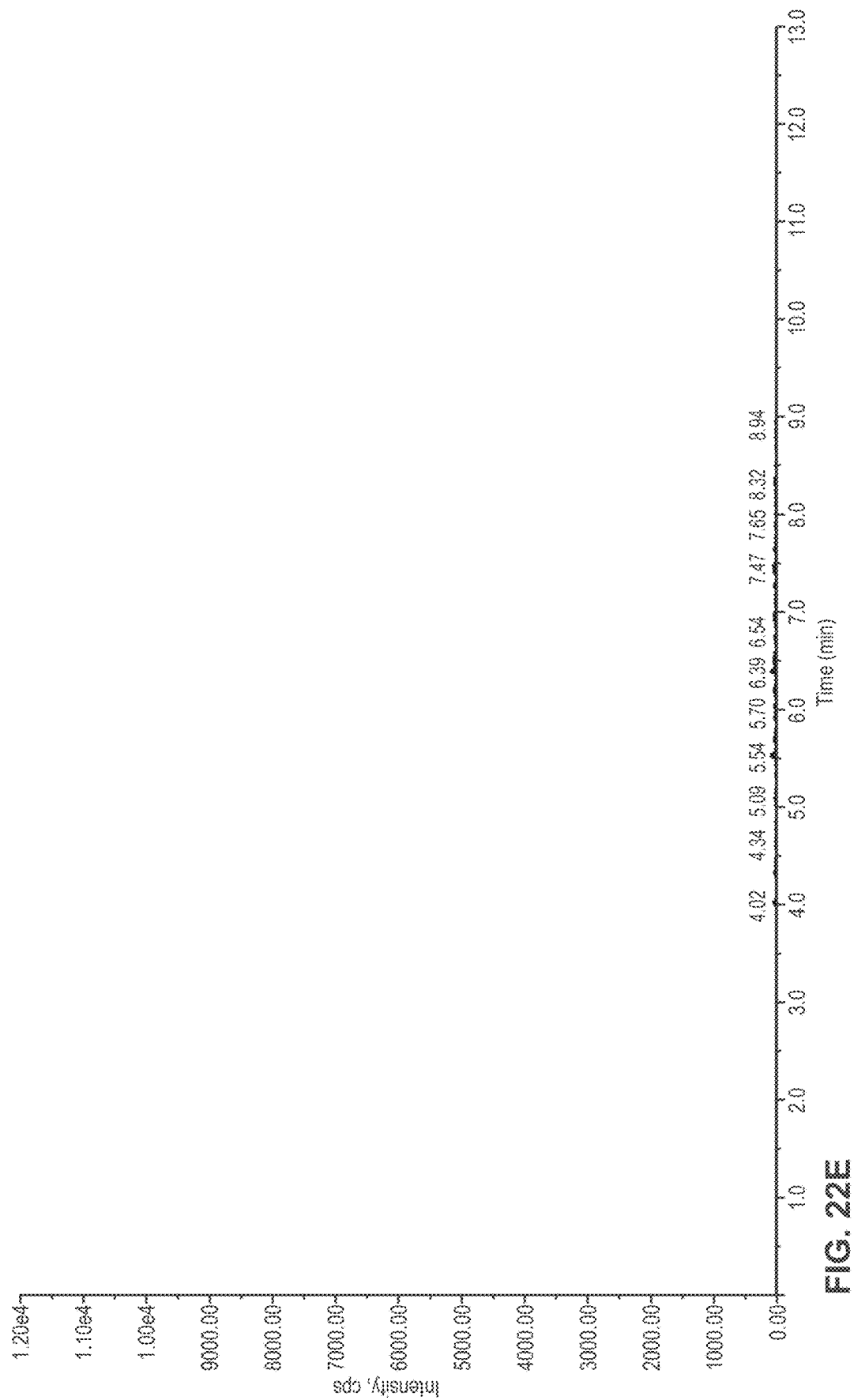
FIG. 22E shows the results of LC-MS/MS analysis of a blank monkey serum sample.
Figure 22F:
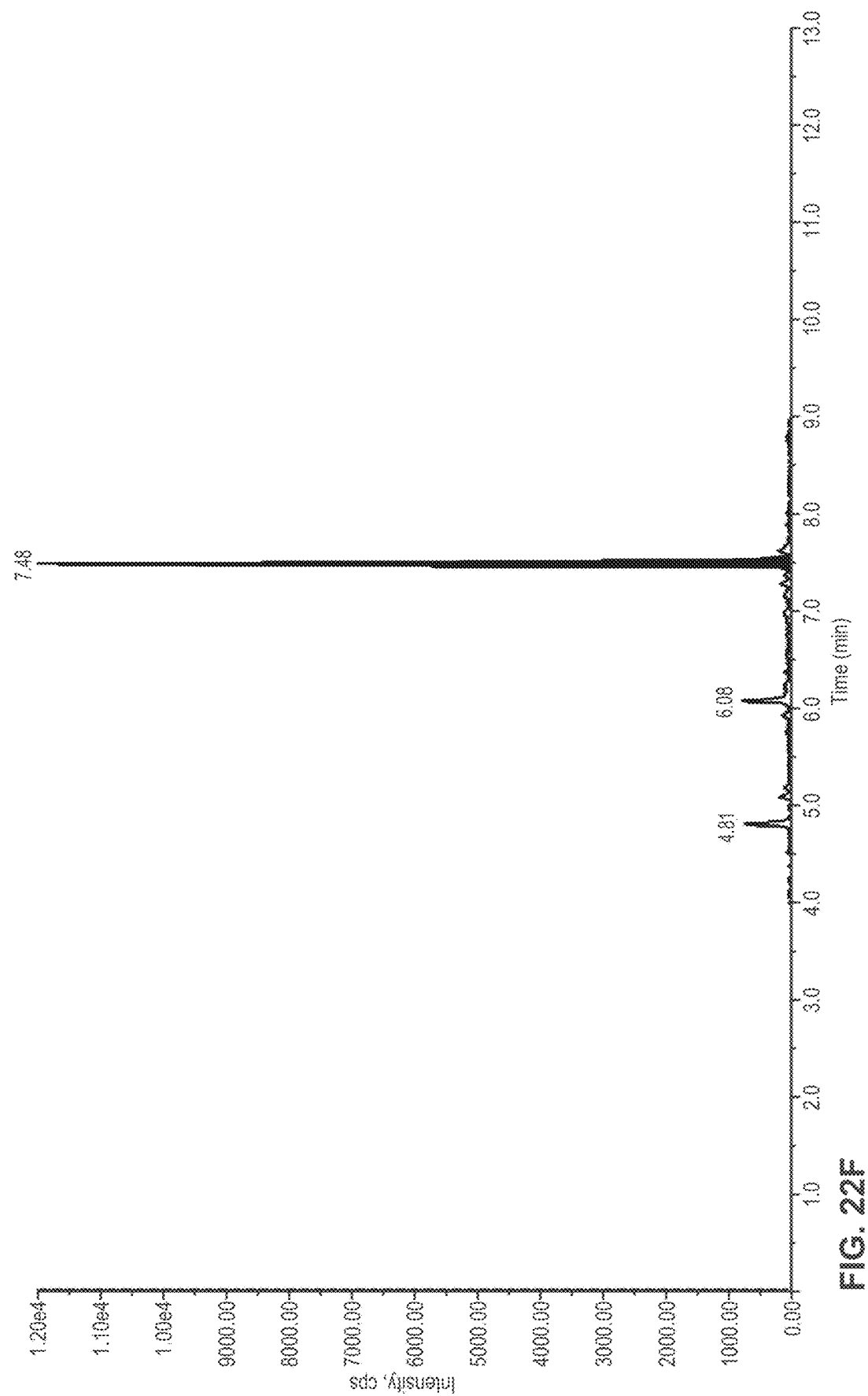
FIG. 22F shows the MS/MS spectrum of a human serum sample spiked with 5 µg/ml trispecific antibody.

Additional experiments were performed to determine whether 5 μg/ml of trispecific antibody could be detected using the surrogate TTPP peptide (SEQ ID NO: 7) when spiked into monkey plasma and human plasma. As shown in FIGS. 22A-22F, the TTPP peptide was detected in the spiked rat plasma (FIG. 22B), spiked monkey plasma (FIG. 22D), and spiked human plasma (FIG. 22F), but not in blank rat plasma (FIG. 22A), blank monkey plasma (FIG. 22C) or blank human plasma (FIG. 22E).

As discussed elsewhere herein, ligand-binding assays (LBAs) such as ELISAs have traditionally been used to detect and quantify therapeutic proteins (e.g., monoclonal antibodies) in biological samples. The quantification of a monoclonal antibody via LBA typically involves using the target antigen as a capture agent or a detection agent. However, LBAs may generate inaccurate results if used to detect trispecific antibody and a soluble target of the trispecific antibody. For a trispecific antibody, quantification via LBA would entail developing three different assays (i.e., one assay per target antigen), which would produce three different concentration datasets, which would not be manageable for preclinical species or human PK exposure assessment. Moreover, it would be difficult to distinguish the amount of free antibody vs. target-bound antibody vs. total antibody in a sample using an LBA. In this Example, a generic LC-MS assay, which can be used in both preclinical and clinical phase, was shown to be capable of measuring a trispecific antibody against a soluble target with high accuracy. The assay was shown to be specific, as demonstrated by the absence of interfering signals in blank plasma samples (see FIGS. 20A-20F). This assay was also shown to be reproducible, as shown in Table 5 with accuracy % difference estimate and inter-run and intra-run % precision within international regulatory acceptance criteria defined by FDA and EMA guidance on bioanalytical method validation (i.e., accuracy % not more than ±20% and precision % not more than ±20%).

Materials and Methods for Preclinical Species

Trispecific antibody was provided as a stock solution with a nominal concentration of 25 mg/mL in 10 mM Histidine, 8% Sucrose, 0.04% polysorbate 80, pH 6.0. Calibration standard and QCs were obtained by diluting the stock solution in rat plasma.

Pellet digestion of rat plasma containing trispecific antibody was optimized from the procedure previously described in Ouyang et al. (2012) *Bioanalysis*. 4(1), 17-28. Briefly, 10 μl of each rat plasma sample containing the trispecific antibody was placed into a 1.5 mL Lobind tubes and mixed with an equal volume of PBS buffer at pH 7.4.

Plasma proteins and the therapeutic antibody in each sample were precipitated by adding 30 µL of methanol to the tubes. After vortexing, the samples were centrifuged for 6 minutes at 2000 rcf (relative centrifugal force) at 5° C. The supernatants were discarded and the protein pellets were resuspended in 40 µl of 200 mM ammonium bicarbonate buffer (ABC). 5 µl of 1M Dithiothreitol (DTT) was added to each resuspended pellet and incubated at 56° C. for 30 min under gentle agitation. The samples were then cooled for 10 min at room temperature. Next, 10 µl of internal standard working solution (100 µg/mL) was added to each sample and mixed. The samples were further incubated with 10 µL of Iodoacetamide (IAA) (100 mM) in 100 mM ABC buffer for 30 min under gentle rotation at room temperature while being protected from light. 30 µg/mL of trypsin and 100 µL of ABC buffer were added to each sample, and the samples were then incubated for 2 hours under gentle rotation at room temperature.

The digestion reactions were stopped with 30 µL 10% formic acid (FA) and centrifuged for 10 min at 16000 rcf at 5° C. Supernatants were subjected to solid phase extraction (SPE) with OASIS MCX elution plates using a positive pressure processor manifold. Briefly, plates were equilibrated with 200 µL of methanol and then with 200 µL of 0.5% FA. 200 µL of each supernatant was applied onto the plates and washed with 200 µL 0.5% FA, 200 µL of 0.5% FA in 80% MeOH solution, and 200 µL of 0.5% FA in 20% MeOH solution. Samples were finally eluted with 2×25 µL of ammonium hydroxide buffer 5%/methanol (40:60, v/v). 10 µL of extracts were diluted within 200 µL of water/formic acid (100:0.5, v/v). 10 µL of each eluted sample was used for LC-MS/MS analysis.

LC-MS/MS analysis was performed with a SCIEX triple Quadrupole API 5500 mass spectrometer running ANALYST® software version 1.6.2. The system was connected to an AGILENT 1290 INFINITY liquid chromatograph system. Chromatography was performed using a X-Bridge Protein BEH C4 column; 300 Å (Waters 100×2.1 mm ID, 3.5 µm particle size) at 50° and a gradient of solvent A (0.1% FA) and B (0.1% FA in acetonitrile). After equilibration for 2.5 min with solvent A, the aqueous solution was brought at 55% after 5 min with a flow rate of 600 µL/min.

MS data were acquired in positive mode with an ion spray voltage of 5500 V, a source temperature of 600° C., and desolvation temperature of 60° C. CE energy was optimized for each peptide (see Table 4).

Materials and Methods for Human Samples

Affinity Purification using ASSAYMAP® BRAVO liquid handling platform from Agilent was performed as follows: In a 96-well plate, 90 µl PBST and 10 µl of human plasma sample were added successively. The plate was vortexed 5 minutes and was put in position 4 maintained at approximately 20° C. on the ASSAYMAP® BRAVO deck. The 96-well plate was filled with 20 µl of 1M Tris, and the reservoirs were filled with the following solutions in successive order: Prime and equilibrate buffer (Phosphate-buffered saline (PBST)), Cartridge Wash 1 (1 M NaCl in PBST), Cartridge Wash 2 (PBST) and elution and syringe wash buffer (1% formic acid). Next, the Affinity Purification protocol on the ASSAYMAP® BRAVO liquid handling platform was run.

Denaturation, reduction, alkylation and digestion steps are performed as follows: The 96-well plate in position 9 was centrifuged for 30 seconds. 50 µl of 0.2% RAPIGEST™ surfactant in 50 mM ammonium bicarbonate and 20 µL of 100 mM DL-Dithiothreitol in 100 mM ammonium bicarbonate were added successively. Next, the plate was centrifuged 30 seconds and incubated at approximately 56° C. for 30 minutes under gentle agitation. Samples were cooled down at room temperature. 20 µL of 250 mM Iodoacetamide in 50 mM ammonium bicarbonate and 50 µl of ISW in 200 mM ammonium bicarbonate @ 0.01% TWEEN® 20 were added. The plate was centrifuged for 30 seconds and then incubated under light-protected conditions at approximately 20° C. for 30 minutes under gentle agitation. 100 µL of 1 µg/µL fresh Trypsin in 50 mM ammonium bicarbonate were added and the samples were incubated at approximately 37° C. overnight. Then 20 µL of 10% formic acid in water (to stop the digestion) was added.

Solid Phase Extraction using an Oasis PRIME MCX µElution plate was performed as follows: 200 µL of each supernatant was applied onto the plates and washed with 200 µL 0.5% FA and 200 µL of 0.5% FA in 80% MeOH solution. Samples were finally eluted with 50 µL of ammonium hydroxide buffer 5%/methanol (40:60, v/v) and 150 µL of water at 0.5% of formic acid were added into the eluted samples. The plate was loaded into auto-sampler tray maintained at +10° C. and 10 µL of each sample was injected.

LC-MS/MS analysis was performed on the human plasma samples as described above for pre-clinical samples.

TABLE 7

| Amino Acid Sequences in Example 3 | |
|---|---|
| SEQ ID NO. | SEQUENCE |
| 7 | TTPPVLDSDG SFFLVSK |
| 12 | EVRLVESGGG LVKPGGSLRL SCSASGFDFD NAWMTWVRQP PGKGLEWVGR ITGPGEGWSV DYAESVKGRF TISRDNTKNT LYLEMNNVRT EDTGYYFCAR TGKYYDFWSG YPPGEEYFQD WGQGTLVIVS SDKTHTQVHL TQSGPEVRKP GTSVKVSCKA PGNTLKTYDL HWVRSVPGQG LQWMGWISHE GDKKVIVERF KAKVTIDWDR STNTAYLQLS GLTSGDTAVY YCAKGSKHRL RDYALYDDDG ALNWAVDVDY LSNLEFWGQG TAVTVSSDKT HTASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKKV EPKSCDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPCR DELTKNQVSL WCLVKGFYPS DIAVEWESNG QPENNYKTTP PVLDSDGSFF LYSKLTVDKS RWQQGNVFSC SVLHEALHSH YTQKSLSLSP G |
| 13 | DFVLTQSPHS LSVTPGESAS ISCKSSHSLI HGDRNNYLAW YVQKPGRSPQ LLIYLASSRA SGVPDRFSGS GSDKDFTLKI SRVETEDVGT YYCMQGRESP WTFGQGTKVD IKDKTHTASE LTQDPAVSVA LKQTVTITCR GDSLRSHYAS |

TABLE 7-continued

Amino Acid Sequences in Example 3

| SEQ ID NO. | SEQUENCE |
|---|---|
|  | WYQKKPGQAP VLLFYGKNNR PSGIPDRFSG SASGNRASLT ITGAQAEDEA DYYCSSRDKS GSRLSVFGGG TKLTVLDKTH TRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 14 | QVQLVQSGGQ MKKPGESMRI SCRASGYEFI DCTLNWIRLA PGKRPEWMGW LKPRGGAVNY ARPLQGRVTM TRDVYSDTAF LELRSLTVDD TAVYFCTRGK NCDYNWDFEH WGRGTPVIVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVCTLPPSRD ELTKNQVSLS CAVKGFYPSD IAVEWESNGQ PENNYKTTPP VLDSDGSFFL VSKLTVDKSR WQQGNVFSCS VLHEALHSHY TQKSLSLSPG |
| 15 | EIVLTQSPGT LSLSPGETAI ISCRTSQYGS LAWYQQRPGQ APRLVIYSGS TRAAGIPDRF SGSRWGPDYN LTISNLESGD FGVYYCQQYE FFGQGTKVQV DIKRTVAAPS VFIFPPSDEQ LKSGTASVVC LLNNFYPREA KVQWKVDNAL QSGNSQESVT EQDSKDSTYS LSSTLTLSKA DYEKHKVYAC EVTHQGLSSP VTKSFNRGEC |
| 16 | LVIYSGSTR |
| 17 | DSTYSLSSTL TLSK |
| 18 | DTLMISR |
| 19 | TTPPVLDSDG SFFLYSK |
| 20 | LTTPPVLDSD GSFFLVSK |

Example 4: Proof of Concept Studies for Using the TTPP Surrogate Peptide in a Generic Mass Spectrometry-Based Assay for Detecting and Quantifying an Exemplary Trispecific Antibody Following Administration to Mice Materials/Methods The materials used in this Example were: trispecific antibody, serum (mouse), Protein G resin tips (Agilent), C18 resin tips (Agilent), SILU™ MAB stable isotope-labeled universal monoclonal antibody internal standard (Sigma), Heavy labeled engineered peptide internal standard (Thermo), 50 mM ammonium bicarbonate, 8M urea with 550 mM Tris base pH 8, 1M sodium chloride in phosphate buffered saline, 125 mM dithiothreitol, 250 mM iodoacetamide, phosphate buffered saline (PBS), trypsin (Promega), LysC (Promega), water, acetic acid, trifluoroacetic acid (TFA), formic acid, acetonitrile Calibration Curve Preparation:

A calibration curve was prepared by serially diluting the trispecific antibody in mouse serum. The concentrations tested in this proof of concept study were 0.012, 0.024, 0.049, 0.098, 0.195, 0.391, 0.781, 1.563, 3.125, 6.25, 12.5, 25.0, 50.0, 100.0, 200.0, 400.0, and 800 µg/mL. Serum without trispecific antibody was used as the zero point.

Stable Isotope-Labeled Internal Standard Preparation:

On day of use, 500 µL 0.1% formic acid was added to a 100 µg vial of SILU™ MAB stable isotope-labeled universal monoclonal antibody (Sigma Aldrich) and allowed to sit at room temperature per manufacturer's instructions. Antibody concentration was 0.2 µg/µL.

Heavy Labeled Engineered Peptide Internal Standard Preparation:

2.5 mL 5% acetonitrile and with 0.1% formic acid was added to the lyophilized TTPP peptide (49 nmol) to achieve a concentration of 19.6 pmol/µL. On the day of use, the concentration of the TTPP peptide was diluted to 0.08 pmol/µL in 40% acetonitrile with 0.1% formic acid.

High Throughput Assay for Quantification of Trispecific Antibody in Serum Using an Automated Liquid Handling Platform (Agilent BRAVO™)

Affinity Purification

For each calibration curve sample or the serum sample to be tested, 10 µL of each sample was added to separate well in a 96-well microplate. Next, 10 µL of additional mouse serum and 30 µL of 0.2 µg/µL stable isotope-labeled universal monoclonal antibody internal standard was added to each well. The 96-well plate was placed on the deck of the automated liquid handling platform (Agilent BRAVO™), and an affinity purification protocol that included the steps below was run:
1. Initial syringe wash
2. Prime (100 µL PBS at 300 µL/min)
3. Equilibrate (50 µL PBS at 10 µL/min)
4. Load Sample (20 µL at 5 µL/min)
5. Cup Wash 1 (25 µL deionized water)
6. Internal Cartridge Wash 1 (50 µL 1M NaCl in PBS at 10 µL/min)
7. Cup Wash 2 (25 µL deionized water)
8. Internal Cartridge Wash 2 (50 µL PBS at 10 µL/min)
9. Stringent syringe wash (50 µL 5% acetic acid)
10. Elute (10 µL 5% acetic acid at 5 µL/min)

Digestion:

The 96-well plate containing the eluted samples was placed on the deck of the automated liquid handling platform (Agilent BRAVO™) and a digestion protocol was performed that included the steps below:

1. Transfer 40 µL 8M Urea with 550 mM Tris pH 8 to each well.
2. Transfer 4.3 µL 125 mM DTT to the wells and then incubate at 40° C. for 60 minutes.
3. Transfer 4.7 µL 250 mM IAM to the wells and then incubate at 25° C. for 60 minutes.
4. Transfer 111 µL of 50 mM ammonium bicarbonate to each well.
5. Transfer 20 µL of 0.5 µg/µL trypsin (1:10 enzyme:substrate) and 0.2 ug/µL rLysC (1:25 enzyme:substrate) to each well and incubate at 37° C. for 120 minutes.
6. Transfer 20 µL of 10% TFA to each well.
7. Transfer 30 µL of 0.08 pmol/µL heavy labeled engineered peptide (peptide internal standard) to each well.

C18 Cleanup

The plate containing the digested samples was placed on the deck of the Agilent Bravo system and the "Peptide Cleanup" protocol was run consisting of the following steps:
1. Initial syringe wash
2. Prime (60% acetonitrile with 0.1% TFA)
3. Equilibrate (50 µL 0.1% TFA at 25 µL/min)
4. Load Samples (190 µL at 5 µL/min)
5. Cup Wash (50 µL deionized water)
6. Internal Cartridge Wash (50 µL 0.1% TFA at 25 µL/min)
7. Stringent Syringe Wash (50 µL 60% acetonitrile with 0.1% TFA)
8. Elute (20 µL 60% acetonitrile with 0.1% TFA at 5 µL/min)

LC-MS/MS

Each eluted sample (20 µL in 60% acetonitrile with 0.1% TFA) was promptly diluted to 100 µL with a solution of 35% acetonitrile and 0.1% formic acid to achieve 40% acetonitrile and 0.1% formic acid. Each sample was transferred to an individual LC-MS vial and analyzed on an LC-MS/MS system. Retention time, parent mass, transitions, and optimized fragmentation conditions vary depending on the peptide sequence and instrument used for analysis. The TTPP peptide (TTPPVLDSDGSFFLVSK (SEQ ID NO: 7)) was analyzed on a WATERS® ACQUITY UPLC® I-Class liquid chromatography system coupled to a SCIEX QTRAP® 6500 LC-MS/MS system under the following conditions
Column: Waters Acquity UPLC Peptide BEH C18 (2.1× 150 mm, 1.7 µm)
Column temperature: 30° C.
Sample Injection Gradient: Begin gradient and hold at 5% B for 1 minute. Increase to 40% B in 17 minutes. Flow rate is 0.25 mL/min. Increase flow rate to 0.4 mL/min. and 90% B for blank injection.
Blank Injection Gradient: Begin gradient and hold at 90% B for 5 minutes. Flow rate is 0.4 mL/min. Decrease flow rate to 0.25 mL/min. and 5% B and hold for 3 minutes.
Mobile Phases: A is water with 0.1% formic acid; B is acetonitrile with 0.1% formic acid
Retention time: 12.9 minutes

TABLE 8

Mass Spectrometry Settings

| | Q1 Mass | Q3 Mass | Declustering Potential | Collision Energy | Entrance Potential | Collision Cell Exit Potential |
|---|---|---|---|---|---|---|
| Light Peptide | 905.5 | 804.4 | 64 | 39 | 10 | 16 |
| Heavy Peptide | 909.5 | 808.4 | 64 | 40 | 13 | 16 |

For this Example, the calibration curve samples and 6 serum samples were analyzed on 2 different days. The mice were dosed twice a week by intraperitoneal injection of trispecific antibody for a total of 7 doses. The study samples analyzed by LC-MS/MS were collected at sacrifice (approximately 30 hours after the last dose) and included a control animal dosed with saline (i.e., Mouse 6 in FIGS. 21A and 21B) and 5 mice dosed with 30 mg/kg of the trispecific antibody (i.e., Mice 1-5 in FIGS. 21A and 21B).

Figure 20B:
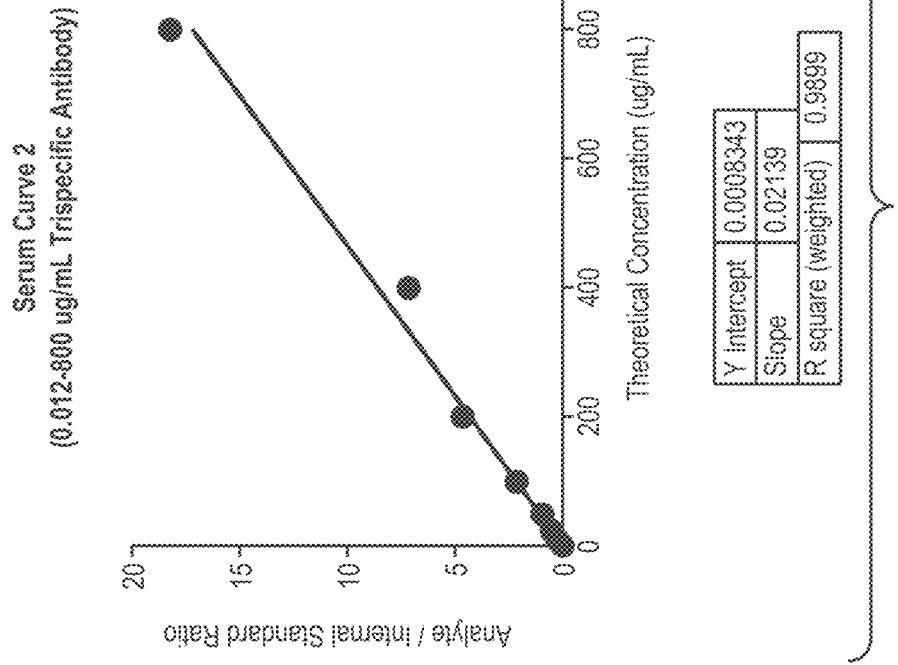
FIG. 20A shows a serum calibration curve analyzed using linear regression analysis with 1/x weighting. The FIG. 20B shows a second serum calibration curve analyzed using linear regression analysis with 1/x weighting. The samples used to construct the curves in FIGS. 20A and 20B were obtained from separate experiments described in Example 3.
Figure 20A:
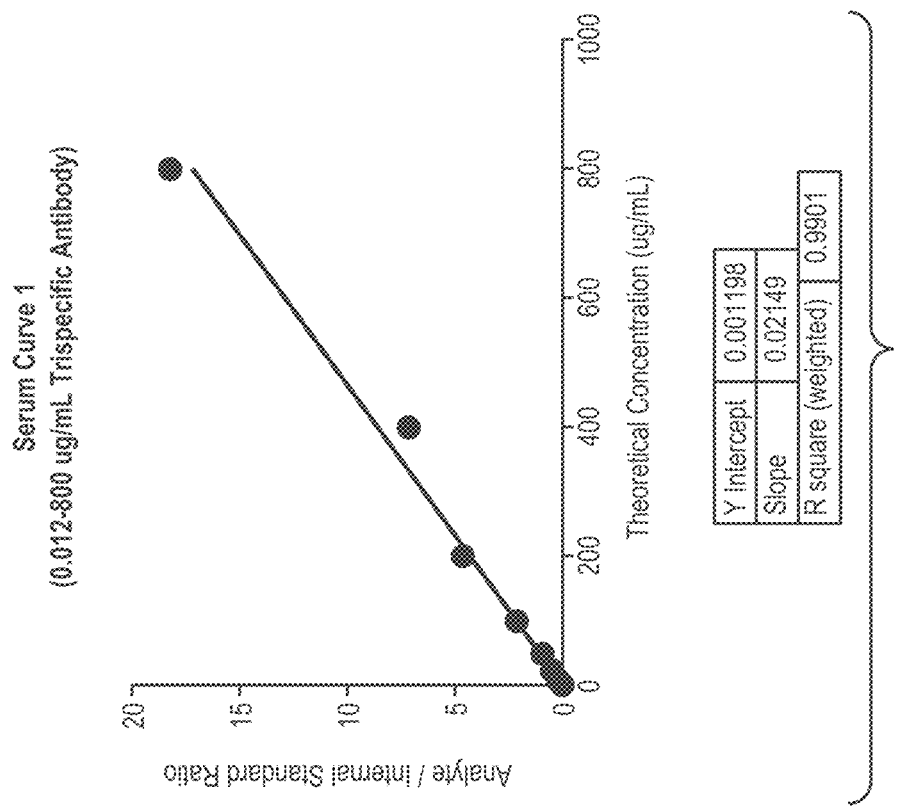

After LC-MS/MS, each serum calibration curve was analyzed by linear regression analysis with 1/x weighting by plotting the ratio of the TTPP peptide to its heavy labeled peptide internal standard versus the theoretical concentration. FIGS. 20A and 20B show the results from this analysis. Both serum curves demonstrated good linearity (with r-squared≥0.99) and bias (≤25%) for concentrations ranging from 0.012 µg/mL to 800 µg/mL.

Figure 21A:
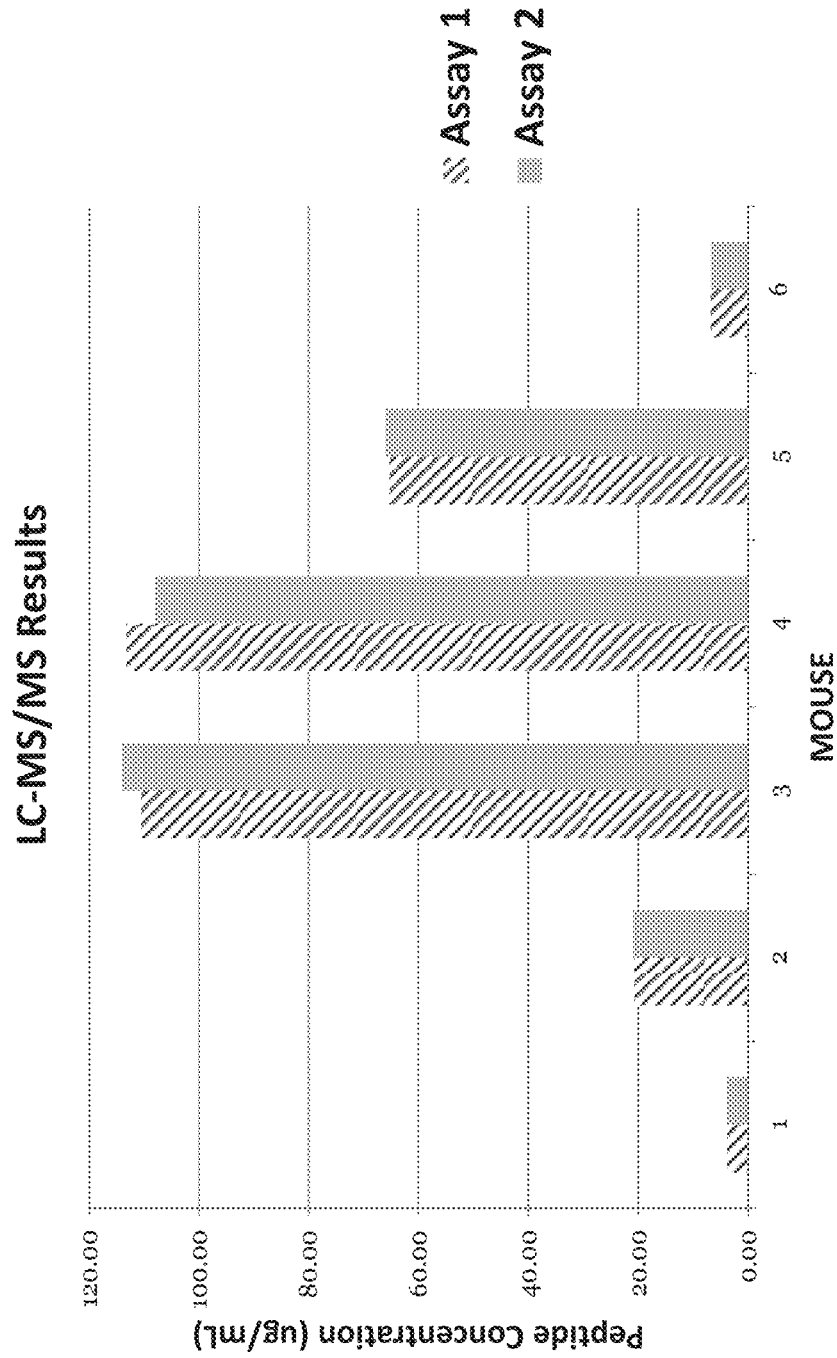
FIG. 21A shows a comparison of relative levels of trispecific antibody as detected by measuring levels of the TTPP peptide in serum obtained from mice to which trispecific antibody was administered via LC-MS/MS.
Figure 21B:
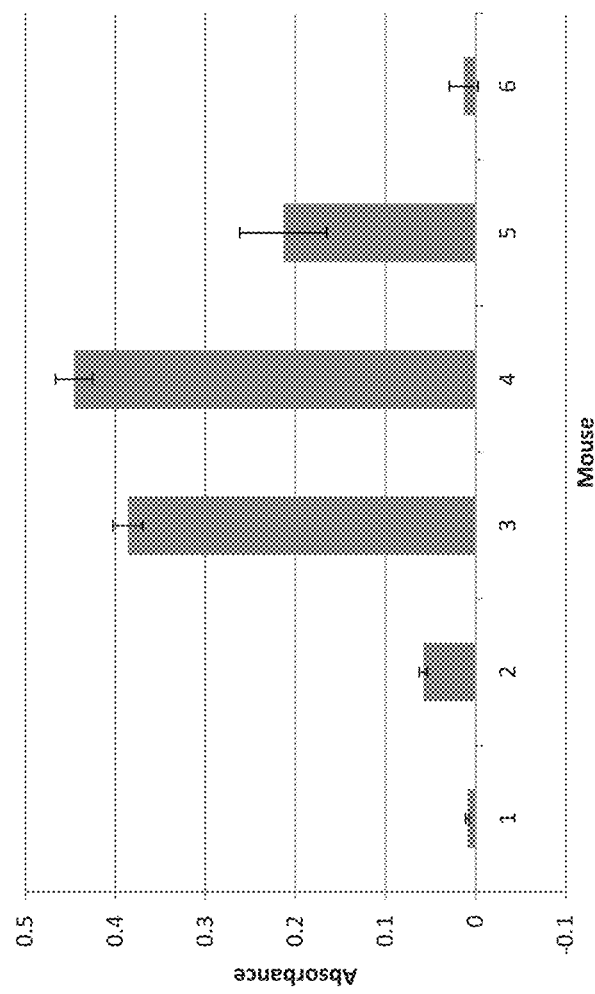
FIG. 21B shows a comparison of relative levels of trispecific antibody as detected via ELISA in serum obtained from mice to which trispecific antibody was administered.

As shown in FIG. 21A, the serum samples showed higher levels of the trispecific peptide in most of the mice dosed with the trispecific antibody (#1-5) and lower levels in the saline dosed mouse (#6). The peptide levels detected in the LC-MS/MS based assay were consistent between the 2 assays (FIG. 21A). These samples were also analyzed using ELISA (n=4 replicates), and the results of ELISA analysis are shown in FIG. 21B. The relative levels of trispecific antibody detected by LC-MS/MS or ELISA show a consistent trend for all samples.

While the disclosure includes various embodiments, it is understood that variations and modifications will occur to those skilled in the art. Therefore, it is intended that the appended claims cover all such equivalent variations that come within the scope of the disclosure. In addition, the section headings used herein are for organizational purposes only and are not to be construed as limiting the subject matter described.

All references cited in this application are expressly incorporated by reference herein.

The invention claimed is:

1. A method for quantitating an amount of a therapeutic polypeptide comprising a portion of an antibody heavy chain constant region in a sample comprising:
   (a) digesting the sample comprising the therapeutic polypeptide comprising the portion of the antibody heavy chain constant region, wherein the portion of the antibody heavy chain constant region comprises an engineered mutation, and wherein digestion produces a peptide fragment derived from the antibody heavy chain constant region that is between 5 and 26 amino acids long and comprises the engineered mutation,
   (b) analyzing the digested sample by mass spectrometry to determine quantity of the therapeutic peptide fragment, thereby determining the quantity of the therapeutic polypeptide comprising the portion of the antibody heavy chain constant region in the sample;
   wherein the therapeutic polypeptide binds to an antigen selected from the group consisting of: A2AR, APRIL, ATPDase, BAFF, BAFFR, BCMA, BlyS, BTK, BTLA, B7DC, B7H1, B7H4/VTCN1, B7H5, B7H6, B7H7, B7RP1, B7-4, C3, C5, CCL2/MCP-1, CCL3/MIP-1a, CCL4/MIP-1b, CCL5/RANTES, CCL7/MCP-3, CCL8/mcp-2, CCL11/eotaxin, CCL15/MIP-1d, CCL17/TARC, CCL19/MIP-3b, CCL20/MIP-3a, CCL21/MIP-2, CCL24/MPIF-2/eotaxin-2, CCL25/TECK, CCL26/eotaxin-3, CCR3, CCR4, CD3, CD19, CD20, CD23/FCER2, CD24, CD27, CD28, CD38, CD39, CD40, CD70, CD80/B7-1, CD86/B7-2, CD122, CD137/41BB, CD137L, CD152/CTLA4, CD154/CD40L, CD160, CD272, CD273/PDL2, CD274/PDL1, CD275/B7H2, CD276/B7H3, CD278/ICOS, CD279/PD-1, CDH1/E-cadherin, chitinase, CLEC9, CLEC91, CRTH2, CSF-1/M-CSF, CSF-2/GM-CSF, CSF-3/GCSF, CX3CL1/SCYD1, CXCL12/SDF1, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb/IL25, IL18, IL22, IL23, IL25, IL27, IL33, IL35, ITGB4/b4 integrin, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2/receptor for IL33, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP/IL7Ra, TSLPR, TWEAK, VEGF, VISTA, Vstm3, WUCAM, or XCR/GPR5/CCXCR1.

2. The method of claim 1, wherein the peptide fragment does not comprise a methionine (M), a cysteine (C), or an asparagine (N) followed by a glycine (G) or serine (S).

3. The method of claim 1, wherein the sample is a whole blood sample, a serum sample, a plasma sample, or a tissue sample.

4. The method of claim 1, wherein the sample is from a mouse, a non-human primate, or a human.

5. The method of claim 4, wherein the non-human primate is a cynomolgus monkey or a rhesus monkey.

6. The method of claim 1, wherein the sample is digested with at least one enzyme, wherein the at least one enzyme is trypsin, chymotrypsin, glutamyl endopeptidase, lysyl endopeptidase, Asp-N, Arg-C, Glu-C, cyanogen bromide (CnBr), or combinations thereof.

7. The method of claim 1, wherein the mass spectrometry is liquid chromatography-tandem mass spectrometry analysis (LC-MS/MS).

8. The method of claim 1, wherein:
(a) the therapeutic polypeptide comprises a CH1 domain, and wherein the CH1 domain comprises the engineered mutation;
(b) the therapeutic polypeptide comprises a CH2 domain, and wherein the CH2 domain comprises the engineered mutation; or
(c) the therapeutic polypeptide comprises a CH3 domain, and wherein the CH3 domain comprises the engineered mutation.

9. The method of claim 8, wherein the therapeutic polypeptide comprises a CH3 domain, wherein the CH3 domain comprises the engineered mutation, and wherein the engineered mutation in the CH3 domain of the antibody heavy chain constant region is T366Y, T366W, T366S, L368A, T394W, T394S, F405A, F405W, Y407T, Y407V, or Y407A.

10. The method of claim 9, wherein the engineered mutation in the CH3 domain of the antibody heavy chain constant region is Y407V, and wherein the CH3 domain comprises an amino acid sequence set forth in SEQ ID NO: 6 (DGSFFLVS) and wherein the digestion produces a peptide fragment comprising the amino acid sequence

```
                                    (SEQ ID NO: 7)
      TTPPVLDSDGSFFLVSK, (SEQ ID NO: 8)
      DGSFFLVSKLTV,
   or
                                    (SEQ ID NO: 9)
      GSFFLVSKLTVD.
```

11. The method of claim 9, wherein the antibody heavy chain constant region comprises the amino acid sequence set forth in SEQ ID NO: 3 or SEQ ID NO: 4.

12. The method of claim 8, wherein the engineered mutation in the CH3 domain of the antibody heavy chain constant region is N434S, wherein the sample is digested with Glu-C and trypsin, and wherein the digestion produces a peptide fragment consisting of the amino acid sequence

```
                                   (SEQ ID NO: 11)
      ALHSHYTQK.
```

13. The method of claim 12, wherein the therapeutic polypeptide comprises the amino acid sequence set forth in SEQ ID NO: 2 or SEQ ID NO: 3.

14. The method of claim 1, wherein the therapeutic polypeptide comprising the portion of the antibody heavy chain constant region is an antibody, an Fc-fusion protein, or an immunoadhesin.

15. The method of claim 14, wherein the polypeptide comprising the portion of the antibody heavy chain constant region is an antibody, and wherein the antibody is a chimeric antibody, a humanized antibody, human antibody, a monospecific antibody, a bispecific antibody, a trispecific antibody, or a multispecific antibody.

16. The method of claim 15, wherein the antibody is a trispecific antibody comprising four polypeptide chains that form three antigen binding sites that specifically bind one or more antigen targets or target proteins, wherein a first polypeptide comprises a structure represented by the formula: $V_{L2}$-$L_1$-$V_{L1}$-$L_2$-CL; the second polypeptide chain comprises a structure represented by the formula: $V_{H1}$-$L_3$-$V_{H2}$-$L_4$-$C_{H1}$-hinge-$C_{H2}$-$C_{H3}$; the third polypeptide chain comprises a structure represented by the formula: $V_{H3}$-$C_{H1}$-hinge-$C_{H2}$-$C_{H3}$; the fourth polypeptide chain comprises a structure represented by the formula: $V_{L3}$-CL, wherein $V_{L1}$ is a first immunoglobulin light chain variable domain; $V_{L2}$ is a second immunoglobulin light chain variable domain; $V_{L3}$ is a third immunoglobulin light chain variable domain; $V_{H1}$ is a first immunoglobulin heavy chain variable domain; $V_{H2}$ is a second immunoglobulin heavy chain variable domain; $V_{H3}$ is a third immunoglobulin heavy chain variable domain; $C_L$ is an immunoglobulin light chain constant domain; $C_{H1}$ is an immunoglobulin $C_{H1}$ heavy chain constant domain; and $L_1$, $L_2$, $L_3$ and $L_4$ are amino acid linkers; wherein the first and second polypeptides form a cross-over light chain-heavy chain pair; and wherein the second polypeptide chain or the third polypeptide chain comprises the amino acid sequence

TTPPVLDSDGSFFLVSK, (SEQ ID NO: 7)

DGSFFLVSKLTV, (SEQ ID NO: 8)
or

GSFFLVSKLTVD. (SEQ ID NO: 9)

17. The method of 16, wherein the first polypeptide comprises the amino acid sequence set forth in SEQ ID NO: 12; the second polypeptide comprises the amino acid sequence set forth in SEQ ID NO: 13; the third polypeptide comprises the amino acid sequence set forth in SEQ ID NO: 14, and the fourth polypeptide comprises the amino acid sequence set forth in SEQ ID NO: 15.

18. The method of claim 15, wherein the antibody is conjugated to a drug or a label.

19. The method of claim 18, wherein the drug is selected from a chemotherapeutic agent, a cytotoxic agent, or a growth-inhibitory agent.

20. The method of claim 15, wherein the antibody is a human IgG1 or a human IgG4 antibody.

21. The method of claim 1, wherein the method is for use in pharmacokinetic study of the polypeptide comprising an antibody heavy chain constant region in a mouse, a non-human primate, and a human.

* * * * *

UNITED STATES PATENT AND TRADEMARK OFFICE
CERTIFICATE OF CORRECTION

| | |
|---|---|
| PATENT NO. | : 11,754,573 B2 |
| APPLICATION NO. | : 17/349840 |
| DATED | : September 12, 2023 |
| INVENTOR(S) | : Christopher Morgan et al. |

It is certified that error appears in the above-identified patent and that said Letters Patent is hereby corrected as shown below:

In the Claims

In Claim 15, Column 66, Line 40: please replace:
"wherein the antibody is a chimeric antibody, a humanized antibody, human antibody"
With:
--wherein the antibody is a chimeric antibody, a humanized antibody, a human antibody--.

Signed and Sealed this
Thirtieth Day of April, 2024

Katherine Kelly Vidal
*Director of the United States Patent and Trademark Office*